(12) United States Patent
Lavoie et al.

(10) Patent No.: US 9,321,781 B2
(45) Date of Patent: Apr. 26, 2016

(54) TOPOISOMERASE INHIBITORS

(75) Inventors: Edmond J. Lavoie, New Brunswick, NJ (US); Ajit K. Parhi, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 48 days.

(21) Appl. No.: 13/318,455

(22) PCT Filed: Nov. 4, 2010

(86) PCT No.: PCT/US2010/033439
§ 371 (c)(1),
(2), (4) Date: May 24, 2012

(87) PCT Pub. No.: WO2010/127363
PCT Pub. Date: Nov. 4, 2010

(65) Prior Publication Data
US 2012/0237531 A1  Sep. 20, 2012

Related U.S. Application Data

(60) Provisional application No. 61/174,951, filed on May 1, 2009.

(51) Int. Cl.
| | |
|---|---|
| A61K 31/5377 | (2006.01) |
| A61K 31/4741 | (2006.01) |
| A61K 31/473 | (2006.01) |
| C07D 491/04 | (2006.01) |
| C07D 221/18 | (2006.01) |
| C07D 491/14 | (2006.01) |
| C07D 491/02 | (2006.01) |
| C07D 221/04 | (2006.01) |
| A61K 31/4738 | (2006.01) |

(52) U.S. Cl.
CPC ............ *C07D 491/14* (2013.01); *A61K 31/473* (2013.01); *A61K 31/4738* (2013.01); *A61K 31/4741* (2013.01); *A61K 31/5377* (2013.01); *C07D 221/04* (2013.01); *C07D 221/18* (2013.01); *C07D 491/02* (2013.01); *C07D 491/04* (2013.01)

(58) Field of Classification Search
None
See application file for complete search history.

(56) References Cited

U.S. PATENT DOCUMENTS

| | | |
|---|---|---|
| 2,915,523 A | 12/1959 | Moore et al. |
| 2,981,731 A | 4/1961 | Moore et al. |
| 2,985,661 A | 5/1961 | Hien et al. |
| 3,267,107 A | 8/1966 | Salley |
| 3,272,707 A | 9/1966 | Tedeschi |
| 3,449,330 A | 6/1969 | Guglielmetti et al. |
| 3,538,097 A | 11/1970 | Lowe et al. |
| 3,542,782 A | 11/1970 | Houlihan et al. |
| 3,849,561 A | 11/1974 | Junzo et al. |
| 3,884,911 A | 5/1975 | Shimada et al. |
| 3,912,740 A | 10/1975 | Zee-Cheng et al. |
| 4,749,708 A | 6/1988 | Maroko |
| 4,761,417 A | 8/1988 | Maroko |
| 4,761,477 A | 8/1988 | Ikekawa et al. |
| 4,925,943 A | 5/1990 | Kanmacher et al. |
| 4,980,344 A | 12/1990 | Maroko |
| 5,106,863 A | 4/1992 | Hajos et al. |
| 5,126,351 A | 6/1992 | Luzzio et al. |
| 5,153,178 A | 10/1992 | Maroko |
| 5,190,753 A | 3/1993 | Behrens et al. |
| 5,244,903 A | 9/1993 | Wall et al. |
| 5,318,976 A | 6/1994 | Luzzi et al. |
| 5,639,759 A | 6/1997 | Magolda et al. |
| 5,646,283 A | 7/1997 | Suzuki et al. |

(Continued)

FOREIGN PATENT DOCUMENTS

| | | |
|---|---|---|
| EP | 0108147 B1 | 5/1984 |
| EP | 0496634 A1 | 7/1992 |

(Continued)

OTHER PUBLICATIONS

Clark et al., Bioorganic & Medicinal Chemistry (2007) 15, 4741-4752.*

(Continued)

*Primary Examiner* — Marcela M Cordero Garcia
*Assistant Examiner* — Catherine Mader
(74) *Attorney, Agent, or Firm* — Viksnins Harris & Padys PLLP

(57) ABSTRACT

The invention provides compounds of formula I: (I) wherein A, B, W, Y, Z, $R_1$, $R_3$ and $R_4$ have any of the meanings defined in the specification and their salts as well as additional compounds and their salts. The invention also provides pharmaceutical compositions comprising a compound of the invention, processes for preparing compounds of the invention, intermediates useful for preparing compounds of the invention, and therapeutic methods for treating cancer, a bacterial infection or a fungal infection using compounds of the invention.

18 Claims, No Drawings

(56) References Cited

U.S. PATENT DOCUMENTS

| | | | |
|---|---|---|---|
| 5,767,142 | A | 6/1998 | LaVoie et al. |
| 5,770,617 | A | 6/1998 | LaVoie et al. |
| 5,807,874 | A | 9/1998 | LaVoie et al. |
| 5,981,541 | A | 11/1999 | LaVoie et al. |
| 6,140,328 | A | 10/2000 | LaVoie et al. |
| 6,486,167 | B1 | 11/2002 | La Voie et al. |
| 6,509,344 | B1 | 1/2003 | Cushman et al. |
| 6,740,650 | B2 | 5/2004 | LaVoie et al. |
| 6,964,964 | B2 | 11/2005 | LaVoie et al. |
| 6,987,109 | B2 | 1/2006 | LaVoie et al. |
| 6,989,387 | B2 | 1/2006 | LaVoie et al. |
| 6,992,089 | B2 | 1/2006 | LaVoie et al. |
| 7,049,315 | B2 | 5/2006 | LaVoie et al. |
| 7,208,492 | B2 | 4/2007 | LaVoie et al. |
| 7,319,105 | B2 * | 1/2008 | LaVoie ............... C07D 491/14 514/248 |
| 7,468,366 | B2 | 12/2008 | LaVoie et al. |
| 7,517,867 | B2 | 4/2009 | LaVoie et al. |
| 7,517,883 | B2 | 4/2009 | LaVoie et al. |
| 7,781,587 | B2 | 8/2010 | LaVoie et al. |
| 7,858,627 | B2 | 12/2010 | LaVoie et al. |
| 8,389,721 | B2 | 3/2013 | Lavoie et al. |
| 2004/0102443 | A1 | 5/2004 | LaVoie et al. |
| 2004/0110760 | A1 | 6/2004 | LaVoie et al. |
| 2004/0110782 | A1 | 6/2004 | LaVoie et al. |
| 2005/0009824 | A1 | 1/2005 | LaVoie et al. |
| 2005/0009825 | A1 | 1/2005 | LaVoie et al. |
| 2005/0009826 | A1 | 1/2005 | LaVoie et al. |
| 2005/0010046 | A1 | 1/2005 | LaVoie et al. |

FOREIGN PATENT DOCUMENTS

| | | |
|---|---|---|
| GB | 2108955 A | 5/1983 |
| SU | 1530628 | 12/1989 |
| WO | WO 92/21661 A1 | 12/1992 |
| WO | WO 96/36612 A1 | 11/1996 |
| WO | WO 97/29106 A1 | 8/1997 |
| WO | WO 98/12181 A1 | 3/1998 |
| WO | WO 98/31673 A1 | 7/1998 |
| WO | WO 99/31067 A1 | 6/1999 |
| WO | WO 00/21537 A1 | 4/2000 |
| WO | WO 01/32631 A2 | 5/2001 |
| WO | WO 03/041653 A2 | 5/2003 |
| WO | WO 03/041660 A2 | 5/2003 |
| WO | WO 03/047505 A2 | 6/2003 |
| WO | WO 2004/014918 A1 | 2/2004 |

OTHER PUBLICATIONS

Aguirre, J. M. et al., "Reaction of 1,2-diarylethylamides with ethyl polyphosphate(EPP): correlation of the von Braun, Ritter and Bischler-Napieralski reactions." Chemical Abstracts, 111(13), Abstract No. 115004, 656 (1989).
Akiyama et al., "Isolation and Genetic Characterization of Human KB Cell Lines Resistant to Multiple Drugs", *Somatic Cell and Molecular Genetics*, vol. 11, No. 2, 117-126 (1985).
Andoh et al., "Characterization of a mammalian mutant with a camptothecin-resistant DNA topoisomerase I", *Proc. Natl. Acad. Sci.*, vol. 84, 5565-5569 (1987).
Andoh et al., "Drug Resistance Mechanisms of Topoisomerase / Drugs", *Advances in Pharmacology*, vol. 29B, *DNA Topoisomerases: Topoisomerase-Targeting Drugs*, 93-103 (1994).
Arumugam et al., "Synthesis of 7, 8-Benzophenanthridines" *Indian Journal of Chemistry*, vol. 12, 664-667 (1974).
Badia et al., "Silicon-mediated isoquinoline synthesis: preparation and stereochemical characterization of 4-hydroxy-3-phenylisoquinolines", Chemical Abstracts, vol. 117 (13), Abstract No. 131034, 730 (1992).
Baezner, Conversion of o-nitrobenzyl chloride and o,p-dinitrobenzyl chloride into acridine derivatives, 3077-3083 (1904) [with English Abstract].
Baezner et al., Conversion of o-nitro and o,p-dinitrobenzylchlroide into acridinic derivatives, 2438-2447 (1906) [with English Abstract].

Bhakuni, D.S. et al., "Protoberberine Alkaloids", *The Alkaloids*, vol. 28, Chapter 2, Academic Press, Inc., 95-181 (1986).
Bjornsit, M-A. et al., "Expression of human DNA topoisomerase I in yeast cells lacking yeast DNA topoisomerase I: restoration of sensitivity of the cells to the antitumor drug camptothecin", *Cancer Research*, 49, 6318-6323 (1989).
Bradsher, C.K. et al., "Alpha-Acyl-o-tolunitriles as intermediates in the preparation of 3-substituted isoquinolines and 1-amino-2-benzopyrylium derivatives", Chemical Abstracts, 89(21), Abstract No. 89: 179810b, 590 (1978).
Brossi, A., "Benzo[c]phenanthridine Alkaloids", *The Alkaloids, Chemistry and Pharmacology*, vol. XXV, *Academic Press, Inc.*, 178-199 (1985).
Buu-Hoi, N.G., "The chemistry of carcinogenic nitrogen compounds. Part V. Angular hydroxybenzacridines and hydroxdibenzacridines", *Journal of the Chemical Society*, Letchworth GB, (1950), 2096-2099 (1950).
Buu-Hoi, N.G. et al., "The Chemistry of Carcinogenic Nitrogen Compounds. Part X. The Pfitzinger Reaction in the Synthesis of 1:2-Benzacridines", *Journal of the Chemical Society*, Letchworth, GB, 279-281 (1952).
Buu-Hoi, N.P. et al., "Carcinogenic Nitrogen Compounds. XV. Polysubstituted Angular Benacridines and Benzophenarsazines", *Chemical Abstracts*, 49(1), Abstract, col. 330, 10-*Organic Chemistry*, 329-330 (1955).
Carmichael, J., "Evaluation of a tetrazolium-based semiautomated colorimetric assay: assessment of chemosensitivity testing", *Cancer Research*, 47, 936-42 (1987).
Cecil Textbook of Medicine, edited by Bennet, J.C. and Plum F., 20th Edition, vol. 1, 1004-1010 (1996).
Chen, A.Y., "A new mammalian DNA topoisomerase I poison Hoechst 33342: cytotoxicity and drug resistance in human cell cultures", *Cancer Research*, 53(6), 1332-1337 (1993).
Chen, et al., "DNA Minor Groove-Binding Ligands: A Different Class of Mammalian DNA Topoisomerase I Inhibitors", *Proceedings of the National Academy of Sciences*, 90, 8131-8135 (1993).
Chen, et al., "DNA Topoisomerases: Essential Enzymes and Lethal Targets", *Annu. Rev. Pharmacol. Toxicol.*, 34, 191-218 (1994).
Cherif, A. et al., "N-(5,5-Diacetoxypent-1-yl)doxorubicin: a new intensely potent doxorubicin analogue", *Journal of Medicinal Chemistry*, 35, 3208-3214 (1992).
Croisy-Delcey, M. et al., "Synthesis and Carcinogenic Activity of Oxidized Benzacridines: Potential Metabolites of the Strong Carcinogen 7-methylbenz[c]acridine and of the Inactive Isomer 12-methylbenz[a]acridine", *Chemical Abstracts*, 98, Abstract No. 43798, 27-29 (1983).
Croisy-Delcey, M. et al., "Synthesis and carcinogenic activity of oxidized benzacridines: potential metabolites of the strong carcinogenic 7-methylbenz[c]acridine and of the inactive isomer 12-methylbenz[a]acridine." *Journal of Medicinal Chemistry*, 26, 303-306 (Abstract) (1983).
Cushman, M. et al., "Synthesis and antitumor activity of structural analogues of the anticancer benzophenanthridine alkaloid fagaronine chloride", *Journal of Medicinal Chemistry*, 28, 1031-1036 (1985).
Cushman, et al., "Synthesis of New Indeno[1,2-c]isoquinolines: Cytotoxic Non-Camptothecin Topoisomerase I Inhibitors", *Journal of Medicinal Chemistry*, 43(20), 3688-3698 (2000).
D'Arpa, et al., "Topoisomerase-targeting antitumor drugs", *Biochimica et Biophysica Acta*, 989, 163-177 (1989).
Denizot, F. et al., "Rapid colorimetric assay for cell growth and survival. Modifications to the tetrazolium dye procedure giving improved sensitivity and reliability", *Journal of Immunological Methods*, 89, 271-277 (1986).
Denny, "Emerging DNA topoisomerase inhibitors as anticancer drugs", *Expert Opin. Emerg. Drugs*, vol. 9(1), 105-133 (2004).
Dominguez, E. et al., "Dehydrogenation reactions of 1-substituted-3-aryltetrahydro-isoquinoline derivatives", *Chemical Abstracts*, 101(11), Abstract No. 090742z,(1984).
Dorofeenko, G. N. et al., "Synthesis of 3-aryl derivatives of 2-benzopyrylium salts with free alpha-positions", *Chemical Abstracts*, 74 (15), Abstract No. 076295, 432 (1971).
Feng et al., "Synthesis of N-substitued 5-[2[(N-alkylamino)ethyl]dibenzo[c,h][1,6]-naphthyridines as novel

(56) References Cited

OTHER PUBLICATIONS topoisomerase I-targeting antitumor agents", *Bioorganic & Medicinal Chemistry* 16, 9295-9301 (2008).
Fitzgerald, J. J. et al., "Reaction of benzocyclobutene oxides with nitriles: synthesis of hypecumine and other 3-substituted isoquinolines", *Chemical Abstracts*, 122(7), Abstract No. 081704, 1128 (1995).
Fox, G.J. et al., "Para-Bromination of Aromatic Amines: 4-Bromo-N,N-Dimethyl-3-(Trifluoromethyl)Aniline", *Organic Syntheses*, vol. 55, 20-23 (1976).
Fuji, N. et al., "Induction of Mammalian DNA Topoisomerase I-mediated DNA Cleavabe and DNA Winding by Bulgarein", *Journal of Biological Chemistry*, 268(18), 13160-13165 (1993).
Gallo, R.C. et al., "Studies on the Antitumor Activity, Mechanism of Action, and Cell Cycle Effects of Camptothecin", *Journal of the National Cancer Institute*, vol. 46, No. 4, 789-795 (1971).
Garcia, A. et al., "A simple approach to 1-substituted 3-arylisoquinolines from deoxybenzoins and nitriles", *Chemical Abstracts*, 110(25), Abstract No. 23107u, 622 (1989).
Gatto, B., "Identification of Topoisomerase I as the Cyctotoxic Target of the Protoberberine Alkaloid Coralyne", *Cancer Research*, 56(12), 2795-2800 (1996).
Giovanella, B.C. et al., "Complete growth inhibition of human cancer xenografts in nude mice by treatment with 20-(S)-camptothecin", *Cancer Research*, 51(11), 3052-3055 (1991).
Godowski, K.C. et al., "Free amine benzophenanthridine alkaloid compositions", USPATFULL Database, No. 95:20510, RN No. 218-38-2 (Benzo[c]phenanthradine), from U.S. Pat. No. 5,395,615, (1995), 3 pages.
Goldman, G.H. et al., "Differential poisoning of human and Aspergillus nidulans DNA topoisomerase I by bi- and terbenzimidazoles", *Biochemistry*, 36(21), (1997).
Gopinath, K.W. et al., "Synthesis of Some 1:2- and 7:8-Benzophenanthridine", *Journal of the Chemistry Society*, 78(2), 504-509 (1958).
Hahn, F.E. et al., "Berberine", *Antibiotics, Mechanism of Action of Antimicrobial and Antitumor Agents*, vol. III, J.W. Corcoran et al., (eds.), Springer-Verlag, 577-584 (1975).
Halligan, B.D. et al., "Purification and Characterization of a Type II DNA Topoisomerase from Bovine Calf Thymus", *The Journal of Biological Chemistry*, 260(4), 2475-2482 (1985).
Hoan, N. et al., "Syntheses from o-halogenated anisoles and phenetoles", *Chemical Abstracts*, 41(20), *American Chemical Society*, Abstract No. 6571bg, 2 pages. (1947).
Hsiang, Y-H et al., "Identification of Mammalian DNA Topoisomerase I as an Intracellular Target of the Anticancer Drug Camptothecin", *Cancer Research*, 48(7), 1722-1726 (1988).
Iwao, M. et al., "A Regiospecific Synthesis of Carbazoles via Consecutive Palladium-Catalyzed Cross-coupling and Aryne-Mediated Cyclization", *Heterocycles*, 36, 1483-1488 (1993).
Izmail'skii, V. A. et al., "Absorption Spectra of Molecular Complexes of Derivatives of Benzacridine and Dibenzacridine", *Chemical Abstracts*, 54(8), Abstract, col. 7335b, 3 pages (1960).
Jacob, J. et al., "Monooxygenase Induction by Various Xenobiotics and its Influence on Rat Liver Microsomal Metabolism by Chrysene in Comparison to Benz[a]anthracene", *Chemical Abstracts*, 107, Abstract No. 34760, 2 pages (1987).
Janin, Y.L. et al., "Synthesis and Evaluation of New 6-Amino-Substituted Benzo[c]phenanthridine Derivatives", *Journal of Medicinal Chemistry*, 36(23), 3686-3692 (1993).
Jayaraman, M. et al., "Synthesis of New Dihydroindeno [1,2-c] isoquinoline and Indenoisoquinolinium Chloride Topoisomerase Inhibitors Having High in Vivo Anticancer Activity in the Hollow Fiber Animal Model", *Journal of Medicinal Chemistry*, 45(1), 242-249 (2002).
Kametani, Tetsuji et al., "Studies on the synthesis of heterocyclic compounds. DCXXVII. The formation of 2,3,9,10-tetramethoxybenz[c]acridine by treatment of 6,7-dimethoxy-1-(4,5-dimethoxy-2-nitrophenethyl)-2-methylisoquinoline with triethyl phosphite", *Chemical and Pharmaceutical Bulletin*, 23(9), 2025-2028 (1975).
Kametani, T. et al., "Synthesis of Heterocyclic Compounds. DCXXVII. Formation of 2,3,9,10-tetramethoxybenz[c]acridine by treatment of 6,7-dimethoxy-1-(4,5-dimethoxy-2-nitrophenethyl)-2-methylisoquinoline with Triethyl Phosphite", *Chemical Abstracts*, 84, Abstract No. 43798, 1 page (1976).
Kanmacher, I. et al., "Synthesis of Isoquino[1,2-b]quinazolines by Cycloaddition Reaction", *Chemical Abstracts*, 114, Abstract No. 207191, 4 pages (1990).
Kar, G.K. et al., "Regioselective Thermal Cyclization of 3-substituted Arylenaminoimine hydrochlorides. A convenient method for the synthesis of Functionalized Polycyclic Quinoline Derivatives", *Chemical Abstracts*, 123, Abstract No. 11828, 1 page (1995).
Kerrigan, J.E. et al., "5H-8,9-Dimethoxy-5-(2-N,N-dimethylaminoethyl)dibenzo[c,h][1,6]naphthyridin-6-ones and Related Compounds as TOP1-Targeting Agents: Influence of Structure on the Ternary Cleavable Complex Formation", *Bioorganic and Medicinal Chemistry Letters*, 13, 3395-3399 (2003).
Kessar, SV. et al., "Azasteroids. Part VII. Synthesis of 7-hydroxy-2-methoxy-7,8,9,10-tetrahydrobenzo[i]phenanthridine", *J. Chem. Soc.*, 259-261 (1971).
Kessar, S.V. et al., "New Routes to Condensed Polynuclear Compounds: Part X-Synthesis of Some Benzo[i]phenanthridine through Benzyne Cyclization", *Indian Journal of Chemistry*, 11, 624-627 (1973).
Kim, J.S. et al., "Influence of steric factors on topoisomerase I inhibition and cytotoxicity of bisbenzimidazoles related to Hoechst 33342", *Proceedings of the 86th Annual Meeting of the American Association for Cancer Research*, 36, Abstract No. 2689, Toronto, Ontario, Canada, 451 (Mar. 1995).
Kim, J.S. et al., "Influence of steric factors on topoisomerase I inhibition and cytotoxicity of bisbenzimidazoles related to Hoechst 33342", *Abstract 7—Proceedings of the 3rd Annual Scientific Retreat of the Cancer Institute of New Jersey*, Princeton Marriott Forrestal Village, 28 (1995).
Kim, J.S. et al., "Steric factors associated with the topoisomerase I inhibition and cytotoxicity of substituted bisbenzimidazoles", *Abstract 10—Proceedings of the American Association of Pharmaceutical Scientists Eastern Regional Meeting*, 27 (1995).
Kim, J.S. et al., "Structure-activity Relationships of Benzimidazoles and Related Heterocycles as Topoisomerase I Poisons", *Bioorganic & Med. Chem.*, 4, 621-630 (1996).
Kim, J.S., "Substituted 2,5'-Bi-1H-benzimidazoles: Topoisomerase I Inhibition and Cytotoxicity", *Journal of Medicinal Chemistry*, 39(4), 992-998 (1996).
Kim, J. S. et al., "Terbenzimidazoles: influence of 2"-, 4-, and 5-subtituents on cytotoxicity and relative potency as topoisomerase I poisons", *Journal of Medicinal Chemistry*, 40(18), 2818-2824 (1997).
Kim, J.S. et al., "Quantitative structure-activity relationships on 5-substituted terbenzimidazoles as topoisomerase I poisons and antitumor agents", *Bioorganic & Medicinal Chemistry*, 6(2), 4 pages [Abstract] (1998).
Kitamura, T. et al., "Isoquinoline derivatives from the Ritter-type reaction of vinyl cations", *Chemical Abstracts*, 102(1), Abstract No. 6157c, (1985).
Klopman, G. et al., "Testing by Artificial Intelligence: Computational Alternatives to the Determination of Mutagenicity", *Chemical Abstracts*, 118, Abstract No. 17489, 1 page (1993).
Knab, A.M. et al., "Mechanisms of Camptothecin Resistance in Yeast DNA Topoisomerase I Mutants", *Journal of Biological Chemistry*, 268(30), 22322-22330 (1993).
Lavoie, E.J. et al., "Structure-activity studies related to minor groove-binding ligands which inhibit mammalian DNA topoisomerase I", Abstract 1—Proceedings of the 85th Annual Meeting of American Association for Cancer Research, San Francisco, CA, 2699 (Apr. 1994).
Lee, J. S. et al., "Coralyne binds tightly to both T A T- and C G C+-containing DNA triplexes", *Biochemistry*, 32(21), 5591-5597 (1993).

(56) References Cited

OTHER PUBLICATIONS

Liu, L.F. et al., "Cleavage of DNA by Mammalian DNA Topoisomerase II", *Journal of Biological Chemistry*, vol. 258, No. 24, 15365-15370 (1983).

Makhey, D., "Protoberberine Alkaloids and Related Compounds as Dual Inhibitors of Mammalian Topoisomerase I and II", *Medicinal Chemistry Research*, 5(1), 1-12 (1994).

Makhey, D., "Coralyne and Related Compounds as Mammalian Topoisomerase I and Topoisomerase II Poisons", *Bioorganic & Medicinal Chemistry*, 4(6), 781-791 (1996).

Meegalla, S.K. et al., "Synthesis and Pharmacological Evaluation of Isoindolo[1,2-b]quinazolinone and Isoindolo[2,1-a]benzimidazole Derivatives Related to the Antitumor Agent Batracylin", *J. Med. Chem.*, 37, 3434-3439 (1994).

Memetzidis, G. et al., "Structure-affinity relationships of berbines or 5,6,13,13a-tetrahydro-8H-dibenzo[a,g]quinolizines at alpha-adrenoceptors", *European Journal of Medicinal Chemistry*, 26, 605-611 (1991).

Messmer, F.M. et al., "Fagaronine, a New Tumor Inhibitor Isolated from Fagara zanthoxyloides Lam. (Rutaceae)", (1972). *Journal of Pharmaceutical Sciences*, 1858-1859 (1972).

Mohanty, N. et al., "New Therapeutic agents of the quinoline series. I. Fused quinolyl compounds", *Chemical Abstracts*, XP 002049521, 1792 (1968).

Mosmann, "Rapid Colorimetric Assay for Cellular Growth and Survival: Application to Proliferation and Cytotoxicity Assays", *Journal of Immunological Methods*, 65(1-2), 55-63 (1983).

Nelson, J.T. et al., "Proton and carbon-13 NMR spectra of fifteen substituted isoquinolines", *Chemical Abstract*, 115(5), Abstract No. 048721, 753 (1991).

Patent Cooperation Treaty, International Searching Authority, Search Report and Written Opinion for PCT/US2010/033439, 15 pages, Jul. 2, 2010.

Peters, D. et al., "Synthesis of Various 5-Substituted Uracils", *Journal of Heterocyclic Chemistry*, 27, 2165-2173 (1990).

Pilch, D. S. et al., "Biophysical Characterization of a Cytotoxic, Topoisomerase I Poison", *Abstract 8—Proceedings of the 3rd Annual Scientific Retreat of the Cancer Institute of New Jersey*, Princeton Marriott Forrestal Village, Princeton, NJ, 2 pages. (Jun. 1, 1995).

Pilch, D.S. et al., "Characterizing the DNA binding modes of a topoisomerase I-poisoning terbenzimidazole: evidence for both intercalative and minor groove binding properties", *Drug Design and Discovery*, 13, 115-133 (1996).

Pilch, D.S. et al., "A terbenzimidazole that preferentially binds and conformationally alters structurally distinct DNA duplex domains: a potential mechanism for topoisomerase I poisoning", *Proc. Nat'l. Acad. Sci. USA*, 94(25), 13565-13570 (1997).

Piper, J.R. et al., "Synthesis and Antifolate Activity of 5-Methyl-5,10-dideaza Analogues of Aminopterin and Folic Acid and an Alternative Synthesis of 5, 10-Dideazatetrahydrofolic Acid, a Potent Inhibitor of Glycinamide Ribonucleotide Formyltransferase", *J. Med. Chem.*, 31, 2164-2169 (1988).

Porai-Koshits, B.A. et al., "Imidazole derivatives. IV. Synthesis of some polybenzimidazoles", J. Gen. Chem. USSR, 23, As related in Chemical Abstracts, 48(10) (1954), col. 12740, (1953), pp. 873-879 (1953).

Quast, U. et al., "Heterocyclic alpha-carbinolamines with the isoquinuclidines skeleton. 3. Benzoisoquinuclidines", *Chemical Abstracts*, 97 (21), Abstract No. 182180s, 806 (1982).

Ramesh, D. et al., "Studies on Polycyclic Azaarenes. 2. Sythesis of Trans-3,4-dihydroxy-3,-dihydrobenz[c]acridine and trans-8,9-dihydroxy-8,9-dihydrobenz[c]acridine", *Chemical Abstracts*, 108, Abstract No. 37626, 2 pages (1988).

Ray, J.K. et al., "A Facile and Convenient Method for the Synthesis of 8-methoxy 10,11-dihydronaphtho[1,2-b]quinolones", *Chemical Abstracts*, 92, Abstract No. 76254, 30-31 (1980).

Ruchelman et al., "Diaza- and Triazachrysenes: Potent Topiisomerase—Targeting Agents with Exceptional Antitumor Activity Against the Human Tumor Xenograft, MDA-MB-435", *Bioorganic & Medicinal Chemistry Letters* 12, 3333-3336 (2002).

Ruchelman et al., "11H-Isoquino[4,3-c]cinnolin-12-ones; Noveml Anticancer Agents with Potent Topiisomerase I-Targeting Activity and Cytotoxicity", *Bioorganic & Medicinal Chemistry*, 12, 795-806 (2004).

Ruchelman et al., "5-(2-Aminoethyl)dibenzo[c,h][1,6]naphthyridin-6-ones: Variation of N-Alkyl Substituents Modulates Sensitivity to Efflux Transporters Associated with Multidrug Resistance", *J. Med. Chem.*, 48, 792-804 (2005).

Safaryan, G.P. et al. "2-Benzopyrylium salts. 25, Reaction of 2-benzopyrylium salts with some nucleophiles", *Chemical Abstracts*, 96(17), Abstract No. 142656z, 739 (1982).

Schiess, P. et al., "Thermolytic ring opening of acyloxybenzocyclobutenes: an efficient route to 3-substituted isoquinolines", *Chemical Abstracts*, 104(19), Abstract No. 168332z, 639 (1986).

Sethi, M.L., "Enzyme Inhibition VI: Inhibition of Reverse Transcriptase Activity by Protoberberine Alkaloids and Structure-Activity Relationships", *Journal of Pharmaceutical Sciences*, 72(5), 538-541 (1983).

Shcherbakova, I.V. et al., "2-Benzopyrilium salts. 35. Synthesis of the natural alkaloid dehydronocoralydine and other substituted salts of dibenzo[a,g] quinolizine", *Chemical Abstracts*, 112 (19), Abstract No. 179554, 823 (1990).

Shelanski, H.A., "Acute and Chronic Toxicity Tests on Electrolytic Iron Poweder", *Bulletin of the National Formulary Committee, XVIII* (5-6), 81-87 (1950).

Singh, M.P. et al., "Synthesis and Sequence-Specific DNA Binding of a Topoisomerase Inhibitory Analog of Hoechst 33258 Designed for Altered Base and Sequence Recognition", *Chem. Res. Toxicol.*, 5, 597-607 (1992).

Singh, S.K. et al., "Nitro and Amino Substitution in the D-Ring of 5-(2-Dimethylaminoethyl)-2,3-methlenedioxy-5H-dibenzo [c,h] [1,6] naphthyridin-6-ones: Efect on Topoisomerase-I Targeting Activity and Cytotoxicity", *Journal of Medicinal Chemistry*,46(11), 2254-2257 (2003).

Sotomayor, N. et al., "Oxidation reactions of 2'-functionalized 3-aryltetrahydro- and 3,4-dihydroisoquinolines", *Chemical Abstracts*, 124 (11), Abstract No. 145854, 1227 (1996).

Southard, G.L. et al., "Drug Delivery Devices", USPATFULL Database, No. 91:36238, RN No. 218-38-2 (Benzo[c]phenanthradine), from U.S. Pat. No. 5,013,553, 2 pages (1991).

Stermitz, F.R., "Synthesis and Biological Activity of Some Antitumor Benzophenanthridinum Salts", *Journal of Medicinal Chemistry*, 18(7), 708-713 (1975).

Studier, F.W. et al., "Use of T7 RNA polymerase to direct expression of cloned genes", *Methods in Enzymology*, 185, 60-89 (1990).

Sun, Q. et al., "Structure-activity studies related to minor groove-binding ligands which inhibit mammalian DNA topoisomerase I", *Cancer Institute of New Jersey's First Annual Scientific Retreat*, Abstract 2, Princeton Marriott Forrestal Village, Princeton, NJ, p. 66 (Jun. 7, 1994).

Sun, Q. et al., "Structure activity of Topoisomerase I Poisons Related to Hoechst 33342", *Bioorganic & Medicinal Chemistry Letters*4 (24), 2871-2876 (1994).

Sun, Q. et al., "Structure activity of novel topoisomerase I inhibitors related to Hoechst 33342", *Abstract 6—Proceedings of the American Association of Pharmaceutical Scientists Eastern Regional Meeting, Hyatt Regencey Hotel*, New Brunswick, NJ, p. 25 (Jun. 5-6, 1995).

Sun, Q. et al., "Synthesis and evaluation of terbenzimidazoles as topoisomerase I inhibitors", *Journal of Medicinal Chemistry*, 38(18), 3638-3644 (1995).

Sun, Q. et al., "Synthesis and Evaluation of Terbenzimidazoles as Topoisomerase I Inhibitors", *Chemical Abstracts*, vol. 123, No. 15, Abstract No. 198740r, 1241 (1995).

Sun, Q. et al., "Synthesis and Pharmacological Evaluation of a Series of Novel DNA Topoisomerase I Inhibitors as Antitumor Agents", *Scientific Proceedings of 86th Annual Meeting of the American Association for Cancer Research*, Abstract 3, vol. 36, Toronto, Canada, 2688 (Mar. 1995).

Sun, Q. et al., "Synthesis and pharmacological evaluation of a series of novel DNA topoisomerase I inhibitors as antitumor agents",

(56) References Cited

OTHER PUBLICATIONS

*Abstract 5—Proceedings of the 3rd Annual Scientific Retreat of the Cancer Institute of New Jersey*, Princeton Marriott Forrestal Village, Princeton, NJ, p. 27 (1995).
Sun, Q. et al., "Synthesis of Benzimidazo[2,1-a]isoquinolines", *Syn. Lett.*, submitted, Paper No. 7, 6 pages (1995).
Tamura, H. et al., "Molecular cloning of a cDNA of a camptothecin-resistant human DNA topoisomerase I and identification of mutation sites", *Nucleic Acids Research*, 19 (1), 69-75 (1991).
Tewey, KM. et al., "Adriamycin-induced DNA damage mediated by mammalian DNA topoisomerase II", *Science*, 226(4673), 466-8 (1984).
Vinogradov, A.E. et al., "Some properties of new DNA specific bisbenzimidazole fluorochromes without a piperazine ring", *Biotechnic & Histochemistry*, 68 (5), 265-270 (1993).
Walterova, D. et al., "Isolation, Chemistry and Biology of Alkaloids from plants of Papaveraceae. Part XCV. Practical application of isotachophoresis in analysis of isoquinoline alkaloids", *Chemical Abstract*, vol. 104, No. 12, No. 95573, (1986).
Wang, L.k. et al., "Inhibition of Topoisomerase I Function by Nitidine and Fagaronine", *Chem. Res. Toxicol.*, 6, 813-818 (1993).
Wang, L-K et al., "Inhibition of Topoisomerase I Function by Coralyne and 5,6-Dihydrocoralyne", *Chem. Res. Toxicol.*, 9, 75-83 (1996).
Wang, H. et al., "Stimulation of topoisomerase II-mediated DNA damage via a mechanism involving protein thiolation", *Biochemistry*, 40(11), 3316-3323 (2001).
Waters, W.A. et al., "Reactions of Free Benzyl Radicals with Benz[a]- and Benz[c]acridine", *Chemical Abstracts*, 54 (1), Abstract, col. 3424b, (1960).
Wilson, W.D. et al., "Coralyne. Intercalation with DNA as a Possible Mechanism of Antileukemic Action", *Journal of Medicinal Chemistry*, 19(10), *Communications to the Editor*, 1261-1263 (1976).
Yadagiri, B. et al., "Convenient Routes to Substituted Benzimidazoles and Imidazolo[4,5-b]pyridines Using Nitrobenzene as Oxidant", *Synthetic Communications*, 20 (7), 955-963 (1990).
Yamamoto, Y et al., "Reaction of 6H-1,3-oxazin-6-one with benzyne giving isoquinoline derivatives", *Chemical Abstracts*, 118(7), Abstract No. 059563u, 831.
Yamashita, Y. et al., "Induction of Mammalian DNA Topoisomerase I and II Mediated DNA Cleavage by Saintopin, a New Antitumor Agent from Fungus", *Biochemistry*, 30(24), 5838-5845 (1991).
Yamashita, Y., "Induction of Mammalian DNA Topoisomerase I Mediated DNA Cleavage by Antitumor Indolocarbazole Derivatives", *Biochemistry*, 31(48), 12069-12075 (1992).
Zee-Cheng, K.Y. et al., "Practical Preparation of Coralyne Chloride", *Journal of Pharmaceutical Sciences*, 61 (6), 969-971 (1972).
Zee-Cheng, K. et al., "Experimental Antileukemic Agents. Coralyne, Analogs, and Related Compounds", *Journal of Medicinal Chemistry*, 17(3), 347-351 (1974).
Zee-Cheng, R.K. et al., "Tetramethoxydibenzoquinolizinium Salts. Preparation and Antileukemic Activity of Some Positional and Structural Isomers of Coralyne", *Journal of Medicinal Chemistry*, 19(7), 882-886 (1976).

\* cited by examiner

TOPOISOMERASE INHIBITORS

PRIORITY OF INVENTION

This application claims priority from U.S. Provisional Application No. 61/174,951 filed 1 May 2009, which application is incorporated by reference.

BACKGROUND OF THE INVENTION

International Patent Application Number PCT/US02/36901, filed Nov. 14, 2002 and published in English on May 22, 2003 as WO 03/041660 A2 discloses toposiomerase poisons of formula XX:

XX that are reported to have inhibitory activity against topoisomerase I and/or topoisomerase II and to displayed anticancer activity. In spite of this disclosure, there is currently a need for agents that have an increased therapeutic window, fewer side effects, increased activity, and/or better pharmacokinetic properties, such as bioavailability or enhanced cell or tissue targeting.

SUMMARY OF THE INVENTION

Applicant has discovered compounds that are inhibitors of topoisomerase I and/or topoisomerase II, or that function as prodrugs for the corresponding compounds of formula XX wherein at least one of Y and Z is hydroxy. Accordingly, the invention provides a compound of the invention which is a compound of formula I:

I wherein:

A and B are independently N or CH;

W is N or CH;

$R_3$ and $R_4$ are each independently H, $(C_1-C_6)$alkyl, or substituted $(C_1-C_6)$alkyl, or $R_3$ and $R_4$ together are =O, =S, =NH or =N—$R_2$;

at least one of Y and Z is aryl$(C_1-C_6)$alkanoyl, heteroaryl$(C_1-C_6)$alkanoyl, $(C_1-C_6)$alkoxycarbonyl, a self-immolative moiety, a cascading prodrug moiety or a linker substituted with one or more (e.g. 1, 2 or 3) targeting moieties and the other is hydrogen, $(C_1-C_6)$alkyl, substituted $(C_1-C_6)$alkyl, $(C_1-C_6)$alkanoyl, substituted $(C_1-C_6)$alkanoyl, —C(=O)NR$_c$R$_d$, aryl$(C_1-C_6)$alkanoyl or heteroaryl$(C_1-C_6)$alkanoyl, wherein any aryl$(C_1-C_6)$alkanoyl or heteroaryl$(C_1-C_6)$alkanoyl may be optionally substituted with one or more (e.g. 1, 2, 3 or 4) groups independently selected from halo, cyano, $(C_1-C_6)$alkyl, carboxy, NO$_2$, hydroxy, $(C_1-C_6)$alkoxy and —NR$_e$R$_f$;

$R_1$ is a —$(C_1-C_6)$alkyl optionally substituted with one or more solubilizing groups;

$R_2$ is $(C_1-C_6)$alkyl, substituted $(C_1-C_6)$alkyl, aryl or heteroaryl;

$R_c$ and $R_d$ are each independently H, $(C_1-C_6)$alkyl or substituted $(C_1-C_6)$alkyl; or $R_c$ and $R_d$ together with the nitrogen to which they are attached form a piperazino, pyrrolidino, or piperidino ring, which ring can optionally be substituted with one or more aryl, heteroaryl, or heterocycle; and $R_e$ and $R_f$ are each independently H, $(C_1-C_6)$alkyl or substituted $(C_1-C_6)$alkyl; or $R_e$ and $R_f$ together with the nitrogen to which they are attached form a piperazino, pyrrolidino, or piperidino ring, which ring can optionally be substituted with one or more aryl, heteroaryl, or heterocycle;

or a salt thereof.

The invention also provides a compound of the invention that is:

5-(2-(dimethylamino)ethyl)-9-methoxy-2,3-methylenedioxy-6-oxo-5,6-dihydrodibenzo[c,h][1,6]naphthyridin-8-yl acetate, 5-(2-(dimethylamino)ethyl)-9-methoxy-2,3-methylenedioxy-6-oxo-5,6-dihydrodibenzo[c,h][1,6]naphthyridin-8-yl pivalate, 5-(2-(dimethylamino)ethyl)-9-methoxy-2,3-methylenedioxy-6-oxo-5,6-dihydrodibenzo[c,h][1,6]naphthyridin-8-yl (3-cyclopentyl)propionate, 5-(2-(dimethylamino)ethyl)-9-methoxy-2,3-methylenedioxy-6-oxo-5,6-dihydrodibenzo[c,h][1,6]naphthyridin-8-yl ethylcarbamate, 5-(2-(dimethylamino)ethyl)-9-methoxy-2,3-methylenedioxy-6-oxo-5,6-dihydrodibenzo[c,h][1,6]naphthyridin-8-yl dimethylcarbamate; or 5-(2-(dimethylamino)ethyl)-9-methoxy-2,3-methylenedioxy-6-oxo-5,6-dihydrodibenzo[c,h][1,6]naphthyridin-8-yl 1,4'-bipiperidine-1'-carboxylate;

or a salt thereof.

The invention also provides a pharmaceutical composition comprising a compound of the invention or a pharmaceutically acceptable salt thereof, and a pharmaceutically acceptable diluent or carrier.

The invention also provides a method for modulating topoisomerase activity in a mammal (e.g. a human) comprising administering to the mammal, an amount of a compound of the invention or a pharmaceutically acceptable salt thereof, effective to provide a topoisomerase modulating effect.

The invention also provides a method of inhibiting cancer cell growth, comprising administering to a mammal (e.g. a human) afflicted with cancer, an amount of a compound of the invention or a pharmaceutically acceptable salt thereof, effective to inhibit the growth of said cancer cells.

The invention also provides a compound of the invention for use in medical therapy (e.g. for use in treating cancer including solid tumors) as well as the use of a compound of the invention or a pharmaceutically acceptable salt thereof, for the manufacture of a medicament useful for the treatment of cancer (e.g. solid tumors) in a mammal (e.g. a human).

The invention also provides the use of a compound of the invention or a pharmaceutically acceptable salt thereof, for the manufacture of a medicament useful for the treatment of a fungal infection in a mammal (e.g. a human).

The invention also provides a compound of the invention or a pharmaceutically acceptable salt thereof, for use in the prophylactic or therapeutic treatment of cancer (e.g. solid tumor) or a fungal infection.

The invention also provides processes and novel intermediates disclosed herein which are useful for preparing compounds of the invention. Some of the compounds of the invention are useful to prepare other compounds of the invention.

DETAILED DESCRIPTION

The following definitions are used, unless otherwise described.

"$(C_1-C_6)$alkyl" denotes both straight and branched carbon chains with one or more, for example, 1, 2, 3, 4, 5, or 6, carbon atoms, but reference to an individual radical such as "propyl" embraces only the straight chain radical, a branched chain isomer such as "isopropyl" being specifically referred to.

"Substituted $(C_1-C_6)$alkyl" is an alkyl group of the formula $(C_1-C_6)$alkyl as defined above wherein one or more (e.g. 1 or 2) carbon atoms in the alkyl chain have been replaced with a heteroatom independently selected from —O—, —S— and NR— (where R is hydrogen or $C_1-C_6$alkyl) and/or wherein the alkyl group is substituted with from 1 to 5 substituents independently selected from cycloalkyl, substituted cycloalkyl, $(C_1-C_6)$alkoxycarbonyl (e.g. —CO$_2$Me), cyano, halo, hydroxy, oxo (=O), carboxy (COOH), aryloxy, heteroaryloxy, heterocyclooxy, nitro, and —NR$^a$R$^b$, wherein R$^a$ and R$^b$ may be the same or different and are chosen from hydrogen, alkyl, arylalkyl, heteroarylalkyl, heterocycloalkyl, cycloalkyl, substituted cycloalkyl, aryl, heteroaryl and heterocyclic. Substituted $(C_1-C_6)$alkyl groups are exemplified by groups such as hydroxymethyl, hydroxyethyl, hydroxypropyl, 2-aminoethyl, 3-aminopropyl, 2-methylaminoethyl, 3-dimethylaminopropyl, 2-carboxyethyl, hydroxylated alkyl amines, such as 2-hydroxy-1-amino-ethyl, and like groups. Substituted $(C_1-C_6)$alkyl groups also include $(C_1-C_6)$alkyl groups substituted with one or more substituents of the formula —NR$_a$R$_b$ where R$_a$ and R$_b$ together with the nitrogen to which they are attached form a nitrogen containing heterocyclic ring. Specific examples of such heterocyclic rings include piperazino, pyrrolidino, piperidino, morpholino, or thiomorpholino. Other substituted $(C_1-C_6)$alkyl groups are $(C_1-C_6)$alkyl groups substituted with one or more carbon-linked oxygen containing heterocyclic rings. Specific examples of such oxygenated heterocyclic rings are, for example, tetrahydrofuranyl, tetrahydropyranyl, 1,4-dioxanyl, and like groups.

In one embodiment of the invention "substituted $(C_1-C_6)$alkyl" is an alkyl group of the formula $(C_1-C_6)$alkyl as defined above wherein the alkyl group is substituted with from 1 to 5 substituents independently selected from cycloalkyl, substituted cycloalkyl, $(C_1-C_6)$alkoxycarbonyl (e.g. —CO$_2$Me), cyano, halo, hydroxy, carboxy (COOH), aryloxy, heteroaryloxy, heterocyclooxy, nitro, and —NR$^a$R$^b$, wherein R$^a$ and R$^b$ may be the same or different and are chosen from hydrogen, alkyl, arylalkyl, heteroarylalkyl, heterocycloalkyl, cycloalkyl, substituted cycloalkyl, aryl, heteroaryl and heterocyclic. Substituted $(C_1-C_6)$alkyl groups are exemplified by groups such as hydroxymethyl, hydroxyethyl, hydroxypropyl, 2-aminoethyl, 3-aminopropyl, 2-methylaminoethyl, 3-dimethylaminopropyl, 2-carboxyethyl, hydroxylated alkyl amines, such as 2-hydroxyaminoethyl, and like groups. Substituted $(C_1-C_6)$alkyl groups also include $(C_1-C_6)$alkyl groups substituted with one or more substituents of the formula —NR$_a$R$_b$ where R$_a$ and R$_b$ together with the nitrogen to which they are attached form a nitrogen containing heterocyclic ring. Specific examples of such heterocyclic rings include piperazino, pyrrolidino, piperidino, morpholino, or thiomorpholino. Other substituted $(C_1-C_6)$alkyl groups are $(C_1-C_6)$ alkyl groups substituted with one or more carbon-linked oxygen containing heterocyclic rings. Specific examples of such oxygenated heterocyclic rings are, for example, tetrahydrofuranyl, tetrahydropyranyl, 1,4-dioxanyl, and like groups.

"$(C_1-C_6)$alkoxy" refers to groups of the formula $(C_1-C_6)$alkyl-O—, where $(C_1-C_6)$alkyl is as defined herein. Preferred alkoxy groups include, by way of example, methoxy, ethoxy, propoxy, iso-propoxy, n-butoxy, tert-butoxy, sec-butoxy, n-pentoxy, n-hexoxy, 1,2-dimethylbutoxy, and like groups.

"Substituted $(C_1-C_6)$alkoxy" refers to a substituted $(C_1-C_6)$alkyl-O— group wherein substituted $(C_1-C_6)$alkyl is as defined above. Substituted $(C_1-C_6)$alkoxy is exemplified by groups such as —OCH$_2$CH$_2$NR$_a$R$_b$, —OCH$_2$CH$_2$CHR$_a$R$_b$, or —OCH$_2$CHOHCH$_2$OH, and like groups. Preferred substituted $(C_1-C_6)$alkoxy groups are $(C_1-C_6)$alkyl substituted with one or more substituents of the formula —NR$_a$R$_b$ where R$_a$ and R$_b$ together with the nitrogen to which they are attached form of a heterocyclic ring. Specific examples of such heterocyclic rings include piperazino, pyrrolidino, piperidino, morpholino, or thiomorpholino. Other preferred substituted $(C_1-C_6)$alkoxy groups are $(C_1-C_6)$alkoxy groups substituted with one or more carbon-linked oxygen containing heterocyclic rings. Specific examples of preferred oxygenated heterocyclic ring substituents are, for example, tetrahydrofuranyl, tetrahydropyranyl, 1,4-dioxanyl, and like groups. Specific examples of such oxygenated heterocyclic rings are, for example, tetrahydrofuranyl, tetrahydropyranyl, 1,4-dioxanyl, and like groups.

"$(C_1-C_6)$alkanoyloxy" includes, by way of example, formyloxy, acetoxy, propanoyloxy, iso-propanoyloxy, n-butanoyloxy, tert-butanoyloxy, sec-butanoyloxy, n-pentanoyloxy, n-hexanoyloxy, 1,2-dimethylbutanoyloxy, and like groups.

Aryl denotes a phenyl radical or an ortho-fused bicyclic carbocyclic radical having about nine to ten ring atoms in which at least one ring is aromatic. Examples of aryl include phenyl, indenyl, and naphthyl.

Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) and quinolyl (or its N-oxide).

The term "heterocycle" or "heterocyclic" refers to a monovalent saturated or partially unsaturated cyclic non-aromatic group which contains at least one heteroatom, preferably 1 to 4 heteroatoms, selected from nitrogen ($NR_x$, wherein $R_x$ is hydrogen, alkyl, or a direct bond at the point of attachment of the heterocycle group), sulfur, phosphorus, and oxygen within at least one cyclic ring and which may be monocyclic or multi-cyclic. Such heterocycle groups preferably contain from 3 to 10 atoms. The point of attachment of the heterocycle group may be a carbon or nitrogen atom. This term also includes heterocycle groups fused to an aryl or heteroaryl group, provided the point of attachment is on a non-aromatic heteroatom-containing ring. Representative heterocycle groups include, by way of example, pyrrolidinyl, piperidinyl, piperazinyl, imidazolidinyl, morpholinyl, indolin-3-yl, 2-imidazolinyl, 1,2,3,4-tetrahydroisoquinolin-2-yl, quinuclidinyl and the like.

"Aryloxy" refers to a group of the formula aryl-O—, where aryl is as defined herein. Examples of aryloxy groups include, phenoxy and 1-naphthyloxy.

"Heteroaryloxy" refers to a group of the formula heteroaryl-O—, where heteroaryl is as defined herein. Examples of heteroaryloxy groups include, 3-pyridinyloxy, 3-furyloxy, and 4-imidazoyloxy.

"Heterocylooxy" refers to a group of the formula heterocycle-O—, where heterocycle is as defined herein. Examples of heterocylooxy groups include, 3-morpholinooxy and 3-tetrahydrofuranyloxy.

"Arylalkyl" refers to a group of the formula aryl-($C_1$-$C_6$) alkyl-, where aryl and ($C_1$-$C_6$)alkyl are as defined herein.

"Heteroarylalkyl" refers to a group of the formula heteroaryl-($C_1$-$C_6$)alkyl-, where heteroaryl and ($C_1$-$C_6$)alkyl are as defined herein.

"Heterocycloalkyl" refers to a group of the formula heterocycle-($C_1$-$C_6$)alkyl-, where heterocycle and ($C_1$-$C_6$)alkyl are as defined herein.

"Solubilizing group(s)" is a substituent that increases the water solubility of the compound of formula I compared to the corresponding compound lacking the R substituent. Examples of solubilizing groups include substituents independently selected from substituted ($C_1$-$C_6$)alkyl, ($C_1$-$C_6$) alkoxycarbonyl (e.g. —$CO_2Me$), cyano, halo, hydroxy, oxo (═O), carboxy (COOH), aryloxy, heteroaryloxy, heterocylooxy, nitro, and —$NR_aR_b$, wherein $R_a$ and $R_b$ may be the same or different and are chosen from hydrogen, alkyl, arylalkyl, heteroarylalkyl, heterocycloalkyl, cycloalkyl, substituted cycloalkyl, aryl, heteroaryl and heterocyclic.

"Aryl($C_1$-$C_6$)alkanoyl group" refers to a group of the formula aryl-($C_1$-$C_6$)alkanoyl-, where aryl and ($C_1$-$C_6$)alkanoyl are defined herein. "Heteroaryl($C_1$-$C_6$)alkanoyl group" refers to a group of the formula heteroaryl-($C_1$-$C_6$)alkanoyl-, where heteroaryl and ($C_1$-$C_6$)alkanoyl are defined herein.

"($C_1$-$C_6$)alkanoyl" includes by way of example, formyl, acetyl, propanoyl, butanoyl, pentanoyl, hexanoyl, and like groups.

"($C_1$-$C_6$)alkoxycarbonyl" refers to group of the formula ($C_1$-$C_6$)alkoxy-C(═O)— where ($C_1$-$C_6$)alkoxy is as defined herein and includes by way of example, methoxycarbonyl, ethoxycarbonyl, propoxycarbonyl, isopropoxycarbonyl, butoxycarbonyl, pentoxycarbonyl, hexyloxycarbonyl and like groups.

As used herein the term "peptide" is a sequence of 2 to 100 amino acids.

Specific and preferred values listed below for radicals, substituents, and ranges, are for illustration only; they do not exclude other defined values or other values within defined ranges for the radicals and substituents.

Specifically, ($C_1$-$C_6$)alkyl can be methyl, ethyl, propyl, isopropyl, butyl, iso-butyl, sec-butyl, pentyl, 3-pentyl, or hexyl and ($C_1$-$C_6$)alkoxy can be methoxy, ethoxy, propoxy, isopropoxy, butoxy, iso-butoxy, sec-butoxy, pentoxy, 3-pentoxy, or hexoxy.

A specific value for A is CH.

Another specific value for A is N.

A specific value for B is N.

Another specific value for B is CH.

A specific value for W is N.

Another specific value for W is CH.

A specific value for Y is H.

Another specific value for Y is ($C_1$-$C_6$)alkyl.

Another specific value for Y is —$CH_3$.

Another specific value for Y is substituted ($C_1$-$C_6$)alkyl.

Another specific value for Y is —$CH_2CH_2OH$.

Another specific value for Y is —$CH_2CH_2OCH_2CH_3$.

Another specific value for Y is —$CH_2CHOHCH_2OH$.

Another specific value for Y is —$CH_2CH_2NR_aR_b$ wherein $R_a$ and $R_b$ are hydrogen or ($C_1$-$C_6$)alkyl.

Another specific value for Y is —$CH_2CH_2NR_aR_b$ wherein $R_a$ and $R_b$ together with the nitrogen to which they are attached form a piperazino, pyrrolidino, piperidino, morpholino, or thiomorpholino ring.

Another specific value for Y is —C(═O)$CH_2NR_aR_b$.

Another specific value for Y is —C(═O)—CHOHCH$_2$OH.

Another specific value for Y is ($C_1$-$C_6$)alkyl substituted with one or more tetrahydrofuranyl, tetrahydropyranyl, or 1,4-dioxanyl rings.

Another specific value for Y is aryl($C_1$-$C_6$)alkanoyl.

Another specific value for Y is heteroaryl($C_1$-$C_6$)alkanoyl.

Another specific value for Y is a cascading prodrug moiety.

Another specific value for Y is the cascading prodrug moiety:

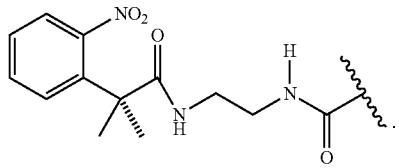

Another specific value for Y is the cascading prodrug moiety:

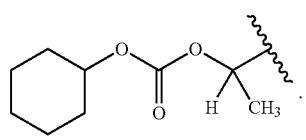 [SMILES: *C(C)OC(=O)OC1CCCCC1]

Another specific value for Y is the cascading prodrug moiety:

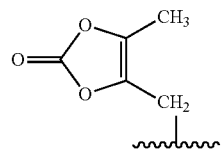

Another specific value for Y is a self-immolative moiety.
Another specific value for Y is the self-immolative moiety:

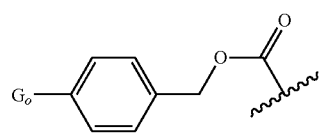

wherein $G_o$ is $NH_2$, NHOH or OH.

Another specific value for Y is the self-immolative moiety:

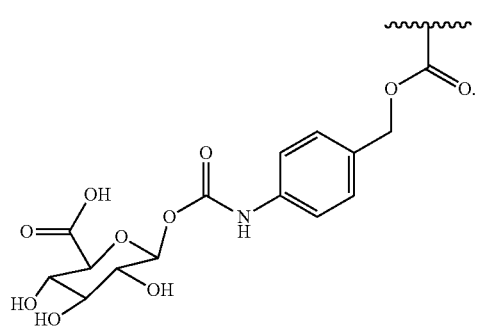 [SMILES: *C(=O)OCc1ccc(NC(=O)OC2OC(C(=O)O)C(O)C(O)C2O)cc1]

Another specific value for Y is the self-immolative moiety:

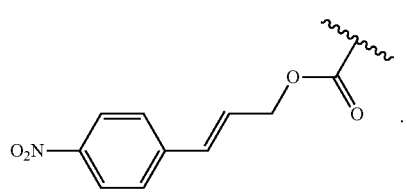 [SMILES: *C(=O)OC/C=C/c1ccc([N+](=O)[O-])cc1]

Another specific value for Y is the self-immolative moiety:

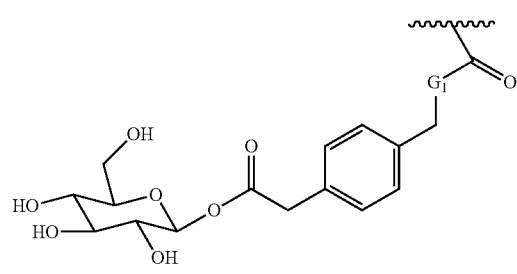

wherein $G_1$ is NH or O.

Another specific value for Y is the self-immolative moiety:

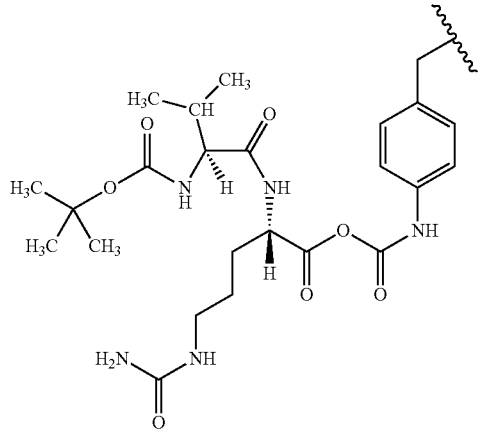

Another specific value for Y is the self-immolative moiety:

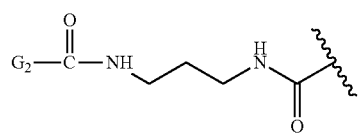

wherein $G_2$ is a peptide that is cleaved by prostate-specific antigen.

Another specific value for Y is the self-immolative moiety:

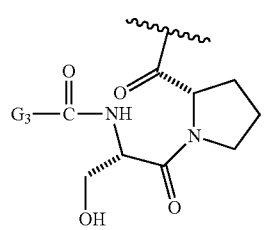

wherein $G_3$ is a peptide that is cleaved by prostate-specific antigen.

Another specific value for Y is the self-immolative moiety:

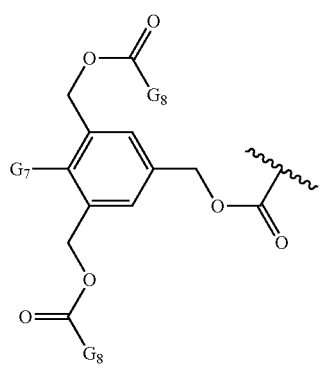

wherein $G_7$ is $NH_2$ or OH and each $G_8$ is independently another compound of the invention wherein the point of attachment is Y or Z.

Another specific value for Y is the self-immolative moiety:

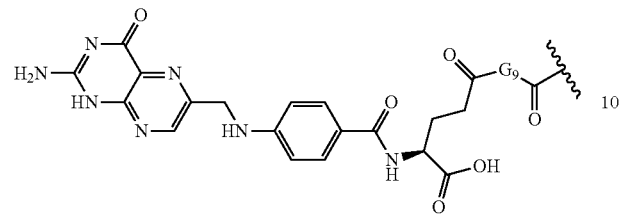

wherein $G_9$ is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—) or (—NH—) and wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, cyano, nitro, halo, hydroxy, oxo (=O), carboxy, aryl, aryloxy, heteroaryl, and heteroaryloxy.

Another specific value for Y is the self-immolative moiety:

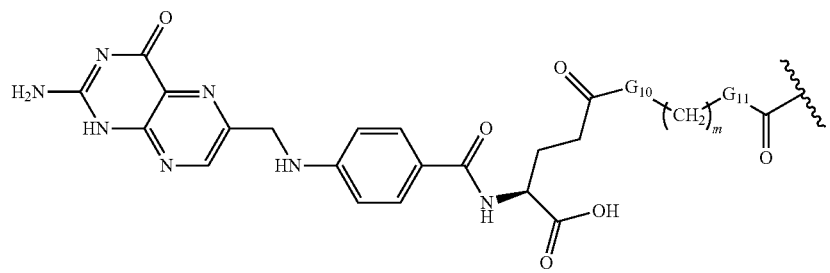

wherein $G_{10}$ and $G_{11}$ are each independently NH and O and m is 2 or 3.

Another specific value for Y is the cascading prodrug moiety:

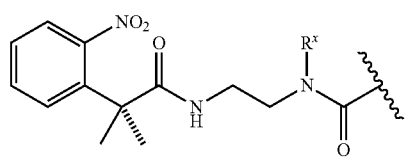

wherein $R^x$ is H or $(C_1-C_6)$alkyl.

Another specific value for Y is the self-immolative moiety:

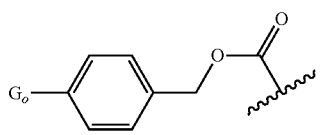

wherein $G_o$ is nitro, $N(R^{xa})R^{xb}$, $NR^{xb}OR^{xc}$, $OR^{xc}$, $NH_2$, NHOH or OH; wherein $R^{xa}$ is $(C_1-C_6)$alkanoyl, $(C_1-C_6)$alkoxycarbonyl, or $R^{xd}R^{xe}NC(=O)$—; $R^{xb}$ is H or $(C_1-C_6)$alkyl; $R^{xc}$ is H, $(C_1-C_6)$alkanoyl, $(C_1-C_6)$alkoxycarbonyl, or $R^{xd}R^{xe}NC(=O)$—; and $R^{xd}$ and $R^{xe}$ are each independently H or $(C_1-C_6)$alkyl.

Another specific value for Y is the self-immolative moiety:

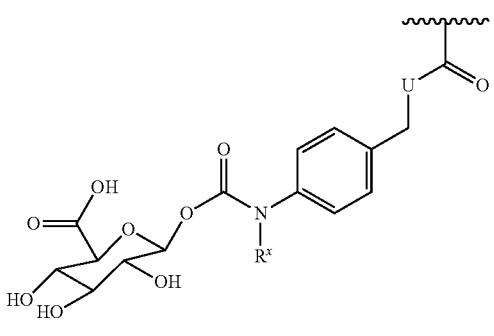

wherein U is O or $NR^x$; and each $R^x$ is independently H or $(C_1-C_6)$alkyl.

Another specific value for Y is the self-immolative moiety:

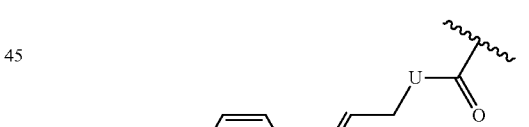

wherein U is O or $NR^x$; and $R^x$ is H or $(C_1-C_6)$alkyl.

Another specific value for Y is the self-immolative moiety:

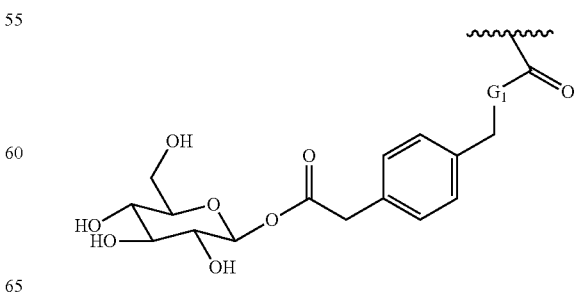

wherein $G_1$ is O or $NR^x$; and $R^x$ is H or $(C_1-C_6)$alkyl.

Another specific value for Y is the self-immolative moiety:

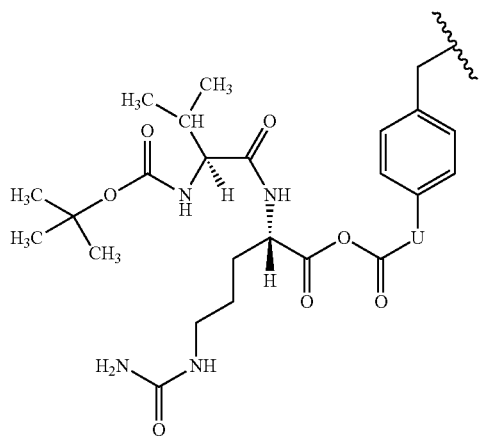

wherein U is O or NR$^x$; and R$^x$ is H or (C$_1$-C$_6$)alkyl.

Another specific value for Y is the self-immolative moiety:

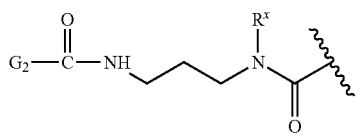

wherein R$^x$ is H or (C$_1$-C$_6$)alkyl; and G$_2$ is a peptide that is cleaved by a dipeptidase or a protease, such as prostate-specific antigen, capthepsin B, plasmin, or a matrix metalloprotease.

Another specific value for Y is the self-immolative moiety:

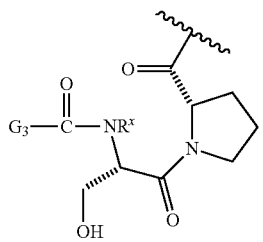

wherein R$^x$ is H or (C$_1$-C$_6$)alkyl; and G$_3$ is a peptide that is cleaved by a dipeptidase or a protease, such as prostate-specific antigen, capthepsin B, plasmin, or a matrix metalloprotease.

Another specific value for Y is the self-immolative moiety:

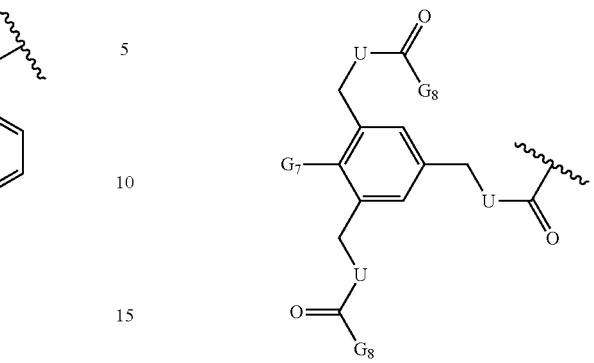

wherein G$_7$ is nitro, N(R$^{xa}$)R$^{xb}$, NR$^{xb}$OR$^{xc}$, OR$^{xc}$, NH$_2$, NHOH or OH; wherein R$^{xa}$ is (C$_1$-C$_6$)alkanoyl, (C$_1$-C$_6$)alkoxycarbonyl, or R$^{xd}$R$^{xe}$NC(=O)—; R$^{xb}$ is H or (C$_1$-C$_6$)alkyl; R$^{xc}$ is H, (C$_1$-C$_6$)alkanoyl, (C$_1$-C$_6$)alkoxycarbonyl, or R$^{xd}$R$^{xe}$NC(=O)—; and R$^{xd}$ and R$^{xe}$ are each independently H or (C$_1$-C$_6$)alkyl; each U is independently O or NR$^x$; each R$^x$ is independently H or (C$_1$-C$_6$)alkyl; and each G$_8$ is independently another compound of formula I attached through Y or Z.

Another specific value for Y is the self-immolative moiety:

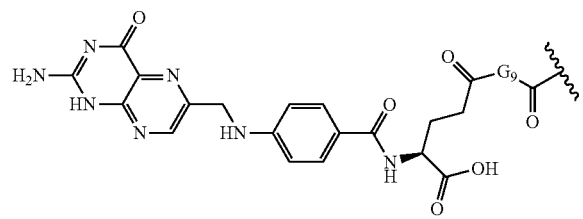

wherein G$_9$ is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—) or (—NR$^x$—) and wherein the chain is optionally substituted on carbon with one or more (e.g. 1, 2, 3, or 4) substituents selected from (C$_1$-C$_6$)alkoxy, (C$_3$-C$_6$)cycloalkyl, (C$_1$-C$_6$)alkanoyl, (C$_1$-C$_6$)alkanoyloxy, (C$_1$-C$_6$)alkoxycarbonyl, (C$_1$-C$_6$)alkylthio, cyano, nitro, halo, hydroxy, oxo (=O), carboxy, aryl, aryloxy, heteroaryl, and heteroaryloxy; and wherein R$^x$ is H or (C$_1$-C$_6$)alkyl.

Another specific value for Y is the self-immolative moiety:

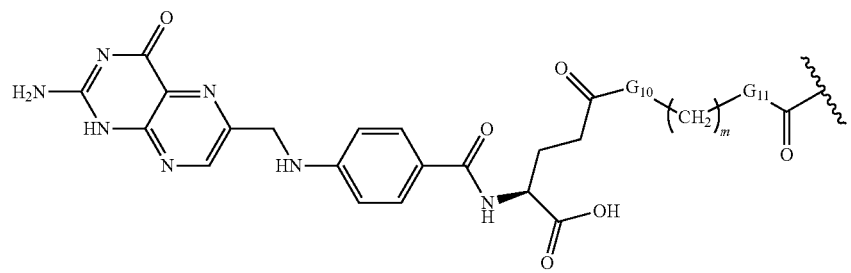

wherein $G_{10}$ and $G_{11}$ are each independently $NR^x$ or O; m is 2 or 3; and $R^x$ is H or $(C_1-C_6)$alkyl.

A specific value for Z is H.
Another specific value for Z is $(C_1-C_6)$alkyl.
Another specific value for Z is $CH_3$.
Another specific value for Z is substituted $(C_1-C_6)$alkyl.
Another specific value for Z is —$CH_2CH_2OH$.
Another specific value for Z is —$CH_2CH_2OCH_2CH_3$.
Another specific value for Z is —$CH_2CHOHCH_2OH$.
Another specific value for Z is —$CH_2CH_2NR_aR_b$ wherein $R_a$ and $R_b$ are hydrogen or $(C_1-C_6)$alkyl.
Another specific value for Z is —$CH_2CH_2NR_aR_b$ wherein $R_a$ and $R_b$ together with the nitrogen to which they are attached form a piperazino, pyrrolidino, piperidino, morpholino, or thiomorpholino ring.
Another specific value for Z is —$C(=O)CHOHCH_2OH$.
Another specific value for Z is —$(C_1-C_6)$alkyl substituted with one or more tetrahydrofuranyl, tetrahydropyranyl, or 1,4-dioxanyl rings.
Another specific value for Z is —$C(=O)CH_2NR_aR_b$.
Another specific value for Z is aryl$(C_1-C_6)$alkanoyl.
Another specific value for Z is heteroaryl$(C_1-C_6)$alkanoyl.
Another specific value for Z is a cascading prodrug moiety.
Another specific value for Z is the cascading prodrug moiety:

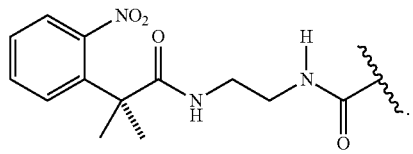

Another specific value for Z is the cascading prodrug moiety:

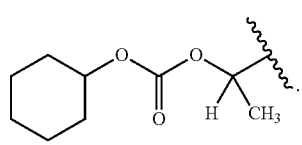 [SMILES: *C(C)OC(=O)OC1CCCCC1]

Another specific value for Z is the cascading prodrug moiety:

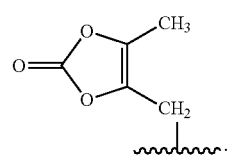

Another specific value for Z is a self-immolative moiety.
Another specific value for Z is the self-immolative moiety:

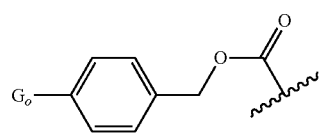

wherein $G_o$ is $NH_2$, NHOH or OH.

Another specific value for Z is the self-immolative moiety:

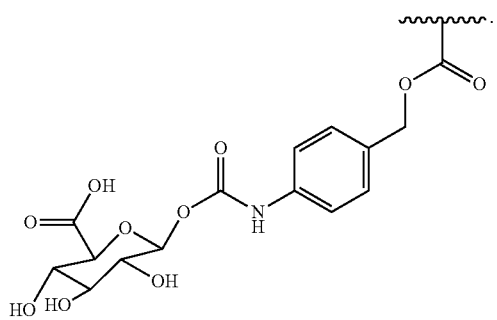 [SMILES: *C(=O)OCc1ccc(NC(=O)OC2OC(C(=O)O)C(O)C(O)C2O)cc1]

Another specific value for Z is the self-immolative moiety:

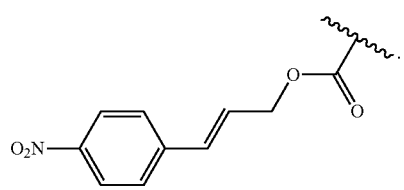 [SMILES: *C(=O)OC/C=C/c1ccc([N+](=O)[O-])cc1]

Another specific value for Z is the self-immolative moiety:

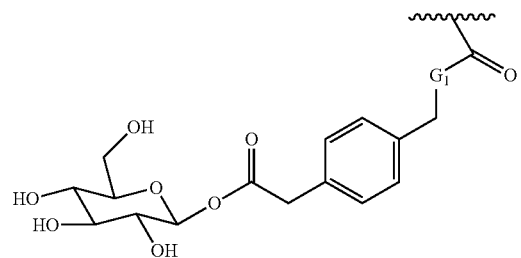

wherein $G_1$ is NH or O.
Another specific value for Z is the self-immolative moiety:

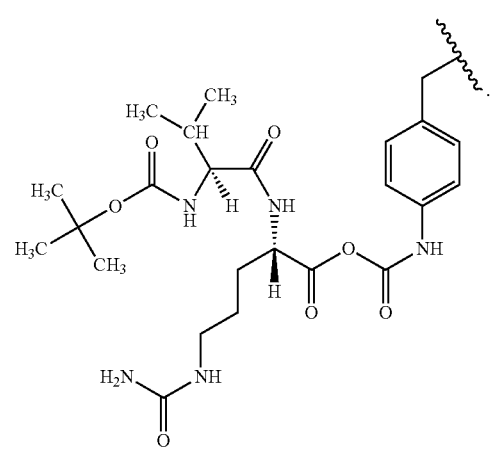

Another specific value for Z is the self-immolative moiety:

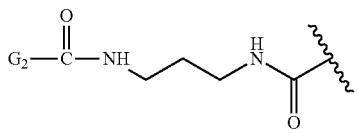

wherein G₂ is a peptide that is cleaved by prostate-specific antigen.

Another specific value for Z is the self-immolative moiety:

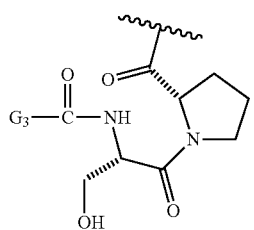

wherein G₃ is a peptide that is cleaved by prostate-specific antigen.

Another specific value for Z is the self-immolative moiety:

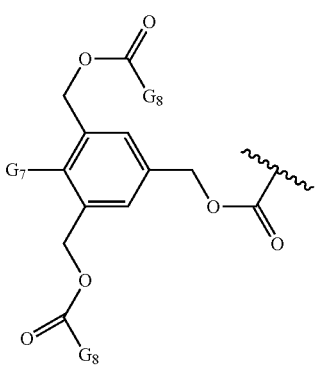

wherein G₇ is NH₂ or OH and each G₈ is independently another compound of the invention wherein the point of attachment is Y or Z.

Another specific value for Z is the self-immolative moiety:

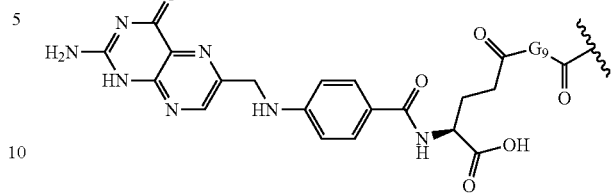

wherein $G_9$ is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—) or (—NH—) and wherein the chain is optionally substituted on carbon with one or more (e.g. 1, 2, 3, or 4) substituents selected from ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, cyano, nitro, halo, hydroxy, oxo (=O), carboxy, aryl, aryloxy, heteroaryl, and heteroaryloxy.

Another specific value for Z is the self-immolative moiety:

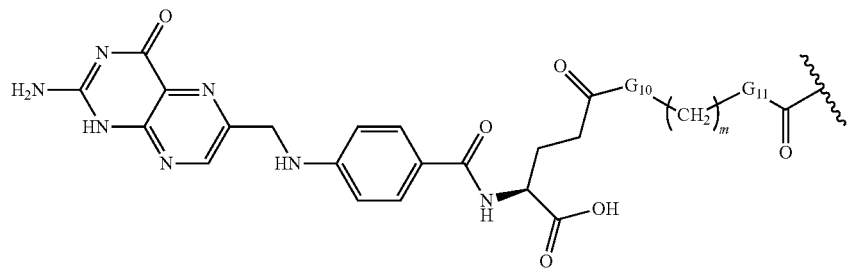

wherein $G_{10}$ and $G_{11}$ are each independently NH and O and m is 2 or 3.

Another specific value for Z is the cascading prodrug moiety:

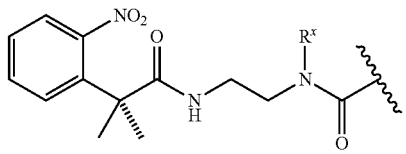

wherein $R^x$ is H or ($C_1$-$C_6$)alkyl.

Another specific value for Z is a self-immolative moiety.

Another specific value for Z is the self-immolative moiety:

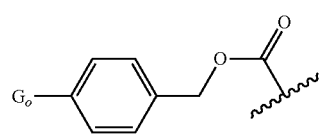

wherein $G_o$ is nitro, $N(R^{xa})R^{xb}$, $NR^{xb}OR^{xc}$, $OR^{xc}$, $NH_2$, NHOH or OH; wherein $R^{xa}$ is $(C_1-C_6)$alkanoyl, $(C_1-C_6)$alkoxycarbonyl, or $R^{xd}R^{xe}NC(=O)-$; $R^{xb}$ is H or $(C_1-C_6)$alkyl; $R^{xc}$ is H, $(C_1-C_6)$alkanoyl, $(C_1-C_6)$alkoxycarbonyl, or $R^{xd}R^{xe}NC(=O)-$; and $R^{xd}$ and $R^{xe}$ are each independently H or $(C_1-C_6)$alkyl.

Another specific value for Z is the self-immolative moiety:

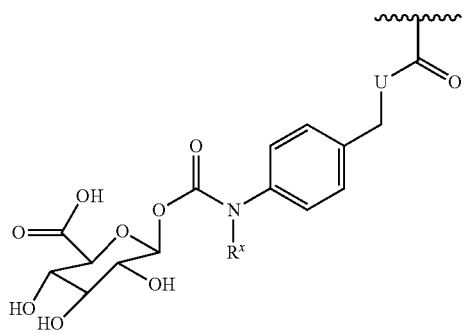

wherein U is O or $NR^x$; and each $R^x$ is independently H or $(C_1-C_6)$alkyl.

Another specific value for Z is the self-immolative moiety:

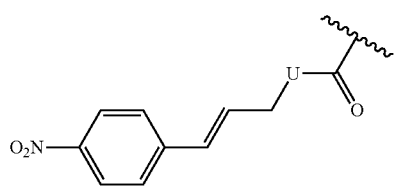

wherein U is O or $NR^X$; and $R^x$ is H or $(C_1-C_6)$alkyl.

Another specific value for Z is the self-immolative moiety:

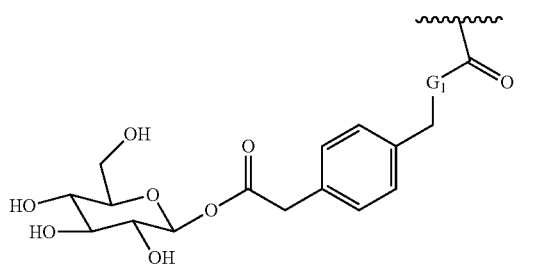

wherein $G_1$ is O or $NR^x$; and $R^x$ is H or $(C_1-C_6)$alkyl.

Another specific value for Z is the self-immolative moiety:

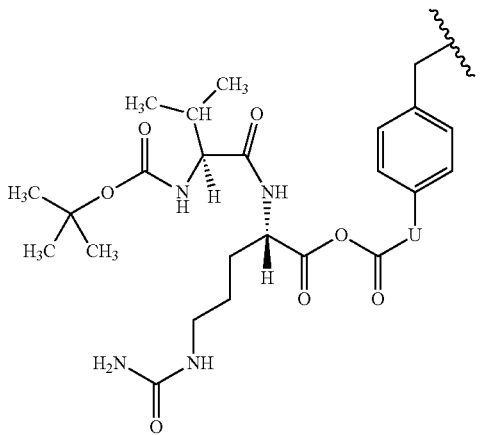

wherein U is O or $NR^x$; and $R^x$ is H or $(C_1-C_6)$alkyl.

Another specific value for Z is the self-immolative moiety:

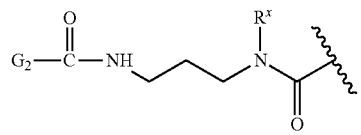

wherein $R^x$ is H or $(C_1-C_6)$alkyl; and $G_2$ is a peptide that is cleaved by a dipeptidase or a protease, such as prostate-specific antigen, capthepsin B, plasmin, or a matrix metalloprotease.

Another specific value for Z is the self-immolative moiety:

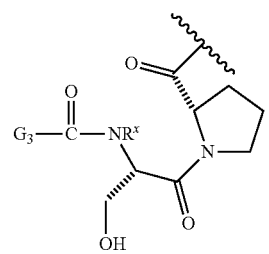

wherein $R^x$ is H or $(C_1-C_6)$alkyl; and $G_3$ is a peptide that is cleaved by a dipeptidase or a protease, such as prostate-specific antigen, capthepsin B, plasmin, or a matrix metalloprotease.

Another specific value for Z is the self-immolative moiety:

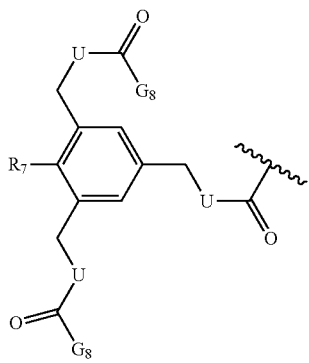

wherein $G_7$ is nitro, $N(R^{xa})R^{xb}$, $NR^{xb}OR^{xc}$, $OR^{xc}$, $NH_2$, NHOH or OH; wherein $R^{xa}$ is $(C_1-C_6)$alkanoyl, $(C_1-C_6)$alkoxycarbonyl, or $R^{xd}R^{xe}NC(=O)-$; $R^{xb}$ is H or $(C_1-C_6)$alkyl; $R^{xc}$ is H, $(C_1-C_6)$alkanoyl, $(C_1-C_6)$alkoxycarbonyl, or $R^{xd}R^{xe}NC(=O)-$; and $R^{xd}$ and $R^{xe}$ are each independently H or $(C_1-C_6)$alkyl; each U is independently O or $NR^x$; each $R^x$ is independently H or $(C_1-C_6)$alkyl; and each $G_8$ is independently another compound of formula I attached through Y or Z.

Another specific value for Z is the self-immolative moiety:

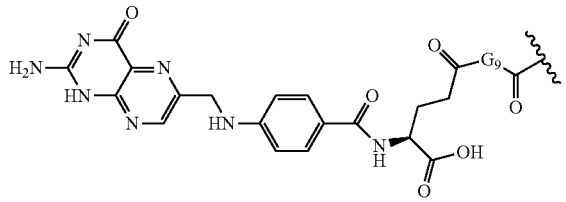

wherein $G_9$ is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—) or (—$NR^x$—) and wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, cyano, nitro, halo, hydroxy, oxo (=O), carboxy, aryl, aryloxy, heteroaryl, and heteroaryloxy; and wherein $R^x$ is H or $(C_1-C_6)$alkyl.

Another specific value for Z is the self-immolative moiety:

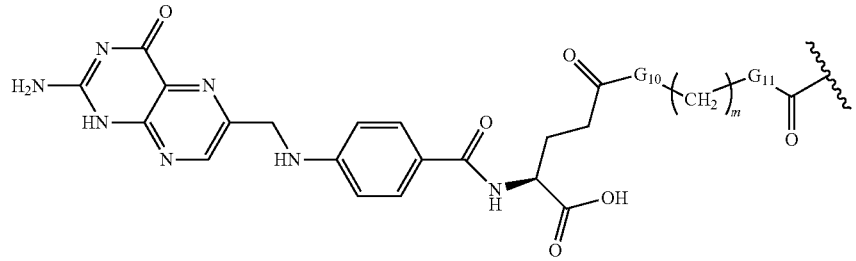

wherein $G_{10}$ and $G_{11}$ are each independently $NR^x$ or O; m is 2 or 3; and $R^x$ is H or $(C_1-C_6)$alkyl.

A specific value for $R_3$ is H.
A specific value for $R_4$ is H.
A specific group of compounds of formula I are compounds wherein $R_3$ and $R_4$ are each H.
Another specific value for $R_3$ and $R_4$ together is =O.
Another specific value for $R_3$ and $R_4$ together is =S.
Another specific value for $R_3$ and $R_4$ together is =NH.
Another specific value for $R_3$ and $R_4$ together is =N—$R_2$.
Another specific value for $R_3$ and $R_4$ together is =N—$R_2$ where $R_2$ is $(C_1-C_6)$alkyl.
Another specific value for $R_3$ and $R_4$ together is =N—$R_2$ where $R_2$ is substituted $(C_1-C_6)$alkyl.
Another specific value for $R_3$ is $(C_1-C_6)$alkyl.
Another specific value for $R_3$ is substituted $(C_1-C_6)$alkyl.
Another specific value for $R_4$ is $(C_1-C_6)$alkyl.
Another specific value for $R_4$ is substituted $(C_1-C_6)$alkyl.
Another specific group of compounds of formula I are compounds wherein $R_3$ is H and $R_4$ is $(C_1-C_6)$alkyl.
Another specific group of compounds of formula I are compounds wherein $R_3$ is H and $R_4$ is substituted $(C_1-C_6)$alkyl.
Another specific group of compounds of formula I are compounds wherein $R_3$ is $(C_1-C_6)$alkyl and $R_4$ is $(C_1-C_6)$alkyl.
Another specific group of compounds of formula I are compounds wherein $R_3$ is substituted $(C_1-C_6)$alkyl and $R_4$ is substituted $(C_1-C_6)$alkyl.
Another specific group of compounds of formula I are compounds wherein $R_3$ is $(C_1-C_6)$alkyl and $R_4$ is substituted $(C_1-C_6)$alkyl.
A specific value for $R_1$ is a $(C_1-C_6)$alkyl substituted with one or more hydroxy groups.
Another specific value for $R_1$ is $(C_1-C_6)$alkyl substituted with one or two hydroxy groups.
Another specific value for $R_1$ is $(C_1-C_6)$alkyl substituted with one hydroxy group.
Another specific value for $R_1$ is hydroxymethyl, 2-hydroxyethyl, 3-hydroxypropyl or 2-hydroxypropyl.
Another specific value for $R_1$ is $(C_1-C_6)$alkyl substituted with one or more mercapto groups.
Another specific value for $R_1$ is $(C_1-C_6)$alkyl substituted with one or more carboxy groups.
Another specific value for $R_1$ is $(C_1-C_6)$alkyl substituted with one or two carboxy groups.
Another specific value for $R_1$ is $(C_1-C_6)$alkyl substituted with one carboxy group.
Another specific value for $R_1$ is $(C_1-C_6)$alkyl substituted with one or more $NR_aR_b$ groups.
Another specific value for $R_1$ is $(C_1-C_6)$alkyl substituted with one or two $NR_aR_b$ groups.
Another specific value for $R_1$ is $(C_1-C_6)$alkyl substituted with one $NR_aR_b$ group.

A specific value for $NR_aR_b$ is —$NH_2$, —$NHCH_3$ or —$N(CH_3)_2$.

Another specific value for $R_1$ is a 2-aminoethyl, 2-(N-methylamino)ethyl or 2-(N,N-dimethylamino)ethyl.

A specific value for $R_1$ is 2-hydroxyethyl.

Another specific value for $R_1$ is 2-aminoethyl.

Another specific value for $R_1$ is 2-(N,N-dimethylamino)ethyl.

Another specific value for $R_1$ is 2-(N,N-diethylamino)ethyl.

Another specific value for $R_1$ is 2-(N,N-diethanolamino)ethyl.

Another specific value for $R_1$ is a $(C_1-C_6)$alkyl substituted with one or more hydroxy, mercapto, carboxy, amino, dimethylamino, methylamino, piperazinyl, pyrrolidinyl, piperidinyl, morpholinyl, thiomorpholinyl, tetrahydrofuranyl, tetrahydropyranyl or 1,4-dioxanyl groups.

A specific value for $R_2$ is $(C_1-C_6)$alkyl substituted with one or more hydroxy, mercapto, carboxy, amino, dimethylamino, methylamino, piperazinyl, pyrrolidinyl, piperidinyl, morpholinyl, thiomorpholinyl, tetrahydrofuranyl, tetrahydropyranyl, or 1,4-dioxanyl groups.

Another specific value for $R_1$ is $(C_2-C_4)$alkyl substituted with one or two groups selected from hydroxy, mercapto, carboxy, amino, dimethylamino, methylamino, piperazinyl, pyrrolidinyl, piperidinyl, morpholinyl, thiomorpholinyl, tetrahydrofuranyl, tetrahydropyranyl and 1,4-dioxanyl.

Another specific value for $R_2$ is $(C_2-C_4)$alkyl substituted with one to two groups selected from hydroxy, mercapto, carboxy, amino, dimethylamino, methylamino, piperazinyl, pyrrolidinyl, piperidinyl, morpholinyl, thiomorpholinyl, tetrahydrofuranyl, tetrahydropyranyl and 1,4-dioxanyl.

Another specific value for $R_1$ or $R_2$ is —$CH_2CH_2NR_aR_b$ wherein $R_a$ and $R_b$ are hydrogen or $(C_1-C_6)$alkyl.

Another specific value for $R_1$ or $R_2$ is —$CH_2CH_2NR_aR_b$ wherein $R_a$ and $R_b$ together with the nitrogen to which they are attached form a piperazino, pyrrolidino, piperidino, morpholino, or thiomorpholino ring.

Another specific value for $R_1$ is hydroxymethyl, hydroxyethyl, hydroxypropyl, 2-aminoethyl, 3-aminopropyl, 2-methylaminoethyl, 3-dimethylaminopropyl, 2-carboxyethyl, or 2-hydroxyaminoethyl.

Another specific value for $R_1$ is $(C_1-C_6)$alkyl substituted with one or more substituents of the formula —$NR_aR_b$ where $R_a$ and $R_b$ together with the nitrogen to which they are attached form a nitrogen containing heterocyclic ring, or a $(C_1-C_6)$alkyl group substituted with one or more oxygen containing heterocyclic rings. Specific examples of such heterocyclic rings include piperazino, pyrrolidino, piperidino, morpholino, or thiomorpholino.

Another specific value for $R_1$ is $(C_1-C_6)$alkyl substituted with one or more carbon-linked oxygen containing heterocyclic rings. Specific examples of such oxygenated heterocyclic rings are, for example, tetrahydrofuranyl, tetrahydropyranyl, 1,4-dioxanyl, and like groups.

Another specific value for Y is a linker substituted with one or more (e.g. 1, 2 or 3) targeting moieties.

Another specific group of compounds of formula I are compounds wherein at least one of Y and Z is a linker substituted with one or more (e.g. 1, 2 or 3) targeting moieties and the other is hydrogen, $(C_1-C_6)$alkyl, substituted $(C_1-C_6)$alkyl, $(C_1-C_6)$alkanoyl, substituted $(C_1-C_6)$alkanoyl, —$C(=O)NR_cR_d$, aryl$(C_1-C_6)$alkanoyl or heteroaryl$(C_1-C_6)$alkanoyl wherein any aryl$(C_1-C_6)$alkanoyl or heteroaryl$(C_1-C_6)$alkanoyl may be optionally substituted with one or more groups independently selected from halo, cyano, $(C_1-C_6)$alkyl, carboxy, $NO_2$, hydroxy, $(C_1-C_6)$alkoxy and —$NR_eR_f$;

A specific formula for "linker" is the formula $W^1$—$W^2$—$W^3$—$W^4$—$W^5$ wherein: $W^1$ is —C(=O)—, —C(=O)N(R)—, —C(=O)O—, —S(O)—, —S(O)_2$— or a direct bond; $W^2$ is $(C_1-C_6)$alkyl, $(C_2-C_6)$alkenyl, $(C_2-C_6)$alkynyl, $(C_3-C_8)$cycloalkyl or $(C_6-C_{10})$aryl or a combination thereof; $W^3$ is —N(R)C(=O)—, —C(=O)N(R)—, —OC(=O)—, —C(=O)O—, —O—, —S—, —S(O)—, —S(O)_2$—, —C(=O)—, —N(R)—, or is absent; $W^4$ is $(C_1-C_6)$alkyl, $(C_2-C_6)$alkenyl, $(C_2-C_6)$alkynyl, $(C_3-C_8)$cycloalkyl or $(C_6-C_{10})$aryl or a combination thereof or is absent; and $W^5$ is —N(R)C(=O)—, —C(=O)N(R)—, —OC(=O)—, —C(=O)O—, —O—, —S—, —S(O)—, —S(O)_2$—, —C(=O)—, —N(R)—, succinimidyl or absent, provided that when $W^4$ is absent $W^5$ is absent; and wherein each R of $W^1$, $W^3$ or $W^5$ is independently H or $(C_1-C_6)$alkyl.

A specific value for $W^1$ is —C(=O)N(R)— or —C(=O)—.

Another specific value for $W^1$ is —C(=O)NMe- or —C(=O)—.

A specific value for $W^2$ is $(C_1-C_6)$alkyl or $(C_6-C_{10})$aryl.

Another specific value for $W^2$ is ethyl or phenyl.

A specific value for $W^3$ is —N(R)C(=O)—, —OC(=O)— or —S—.

Another specific value for $W^3$ is —NHC(=O)—, —OC(=O)— or —S—.

A specific value for $W^4$ is $(C_1-C_6)$alkyl or $W^4$ is absent.

Another specific value for $W^4$ is ethyl or propyl.

In one embodiment of the invention $W^4$ and $W^5$ are absent.

A specific value for $W^5$ is —C(=O)—, succinimidyl or $W^5$ is absent.

In one embodiment of the invention $W^5$ is absent.

A specific linker is:

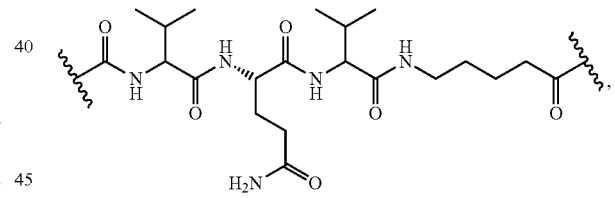

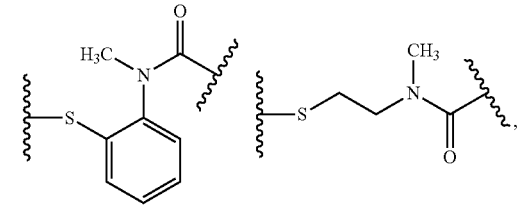

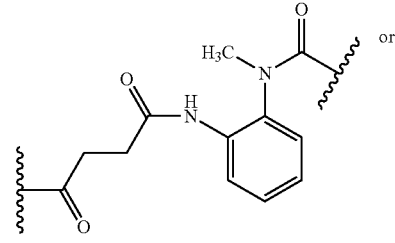

-continued

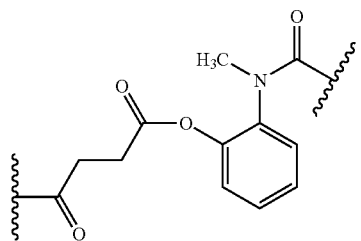

wherein the wavy line on the left depicts the point of attachment to the targeting moiety and wherein the wavy line on the right is the point of attachment to the oxygen of formula I.

Another specific linker is:

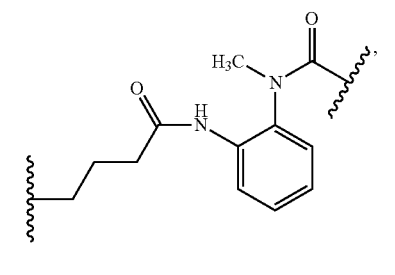

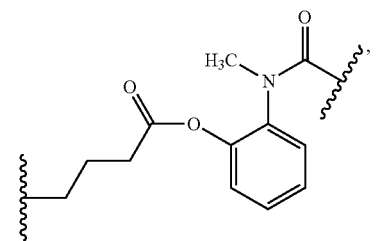

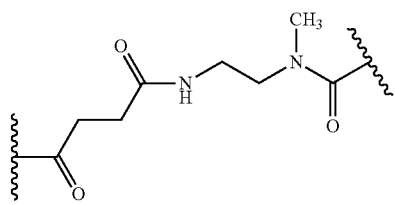

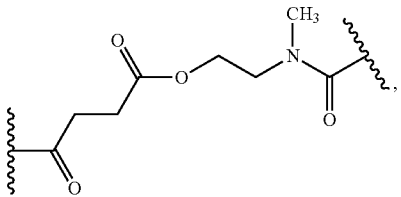

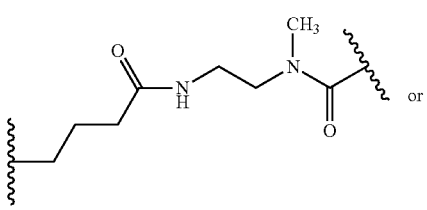 or

-continued

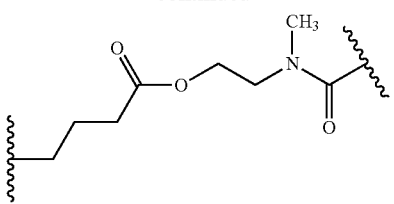

wherein the wavy line on the left depicts the point of attachment to the targeting moiety and wherein the wavy line on the right is the point of attachment to the oxygen of formula I.

Another specific linker is:

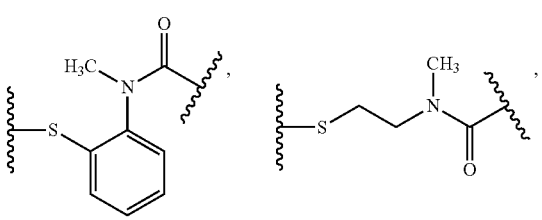

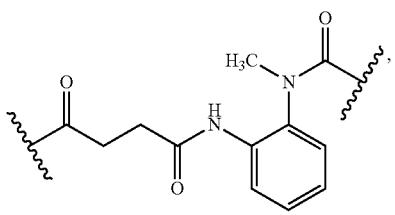

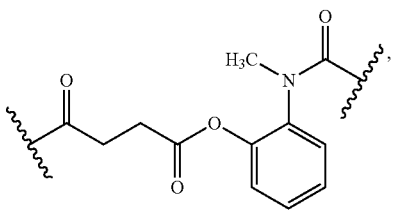

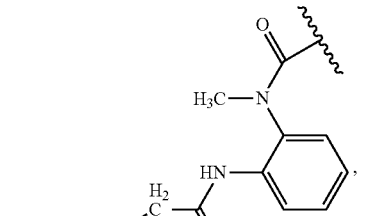

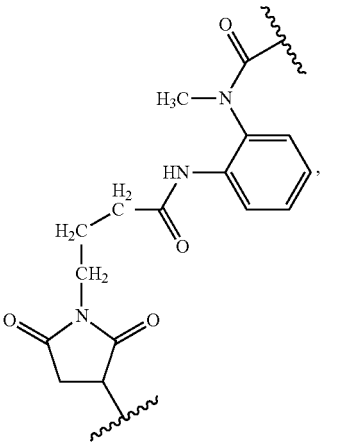

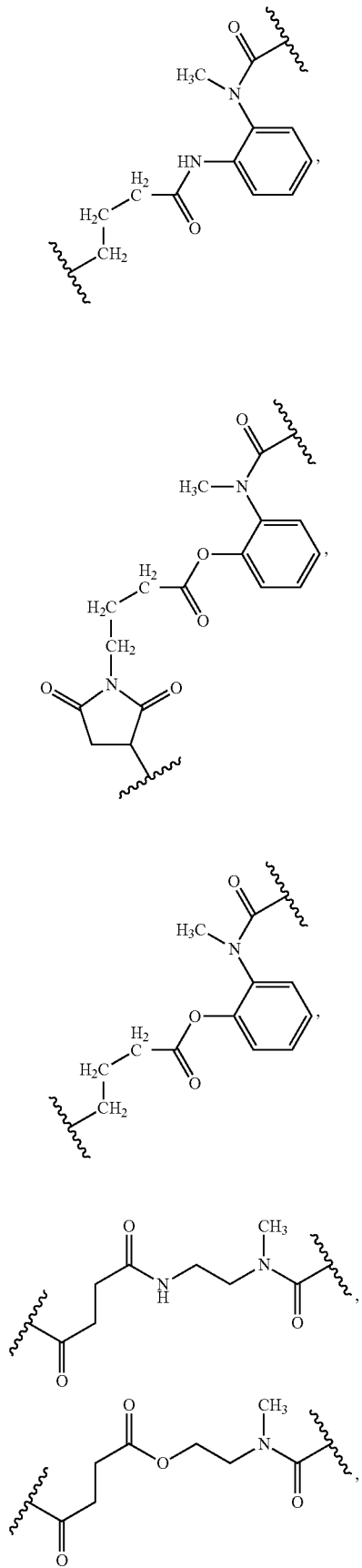
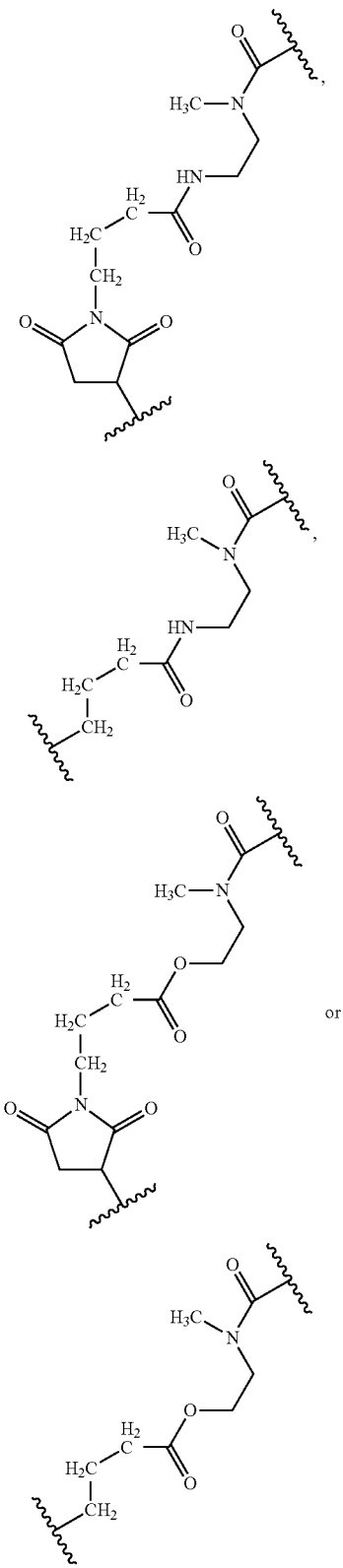
wherein the wavy line on the left depicts the point of attachment to the targeting moiety and wherein the wavy line on the right is the point of attachment to the oxygen of formula I.

Another specific value for Y is:
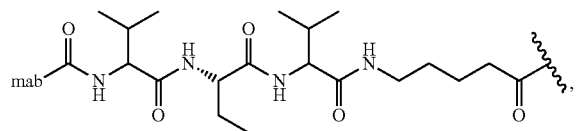
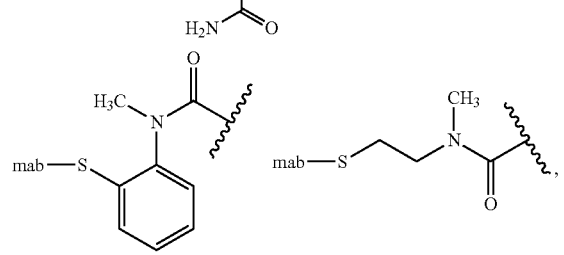
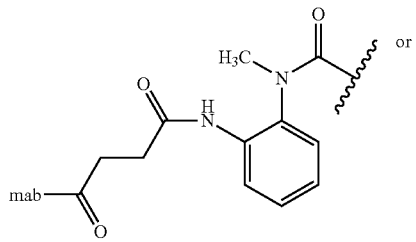
wherein mab is a monoclonal antibody.
Another specific value for Y is:
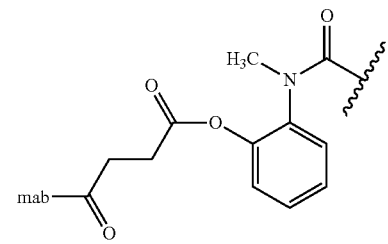
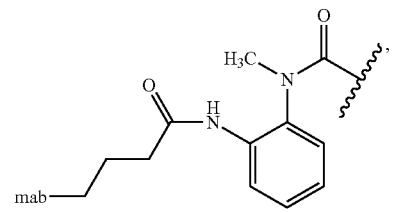
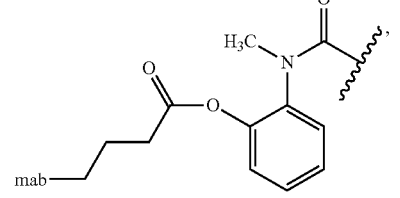
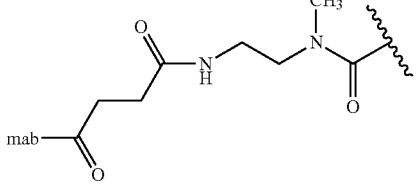
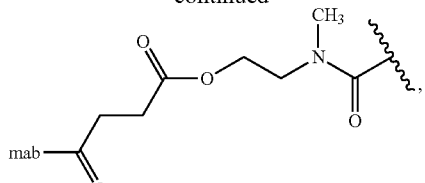
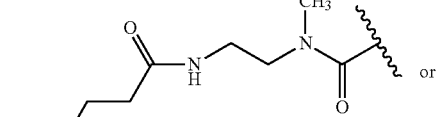
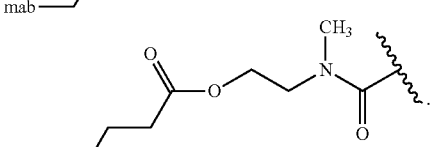
wherein mab is a monoclonal antibody.
Another specific value for Y is:
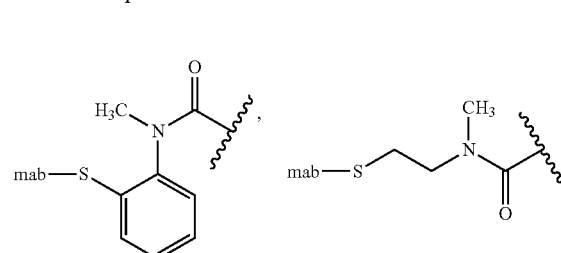
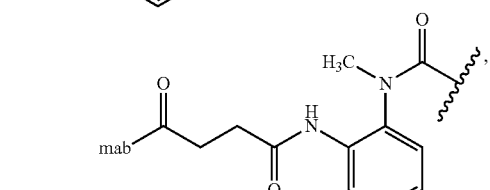
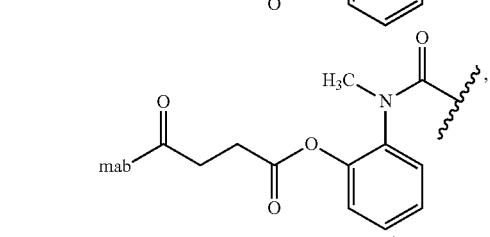
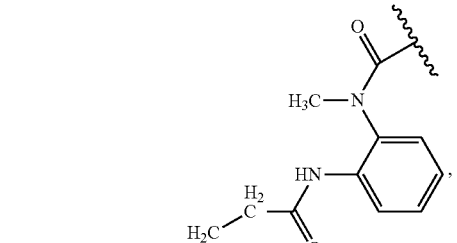
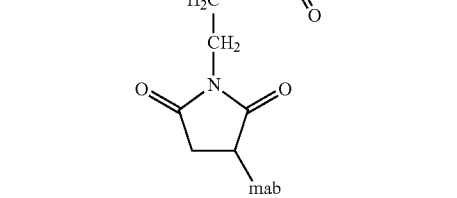

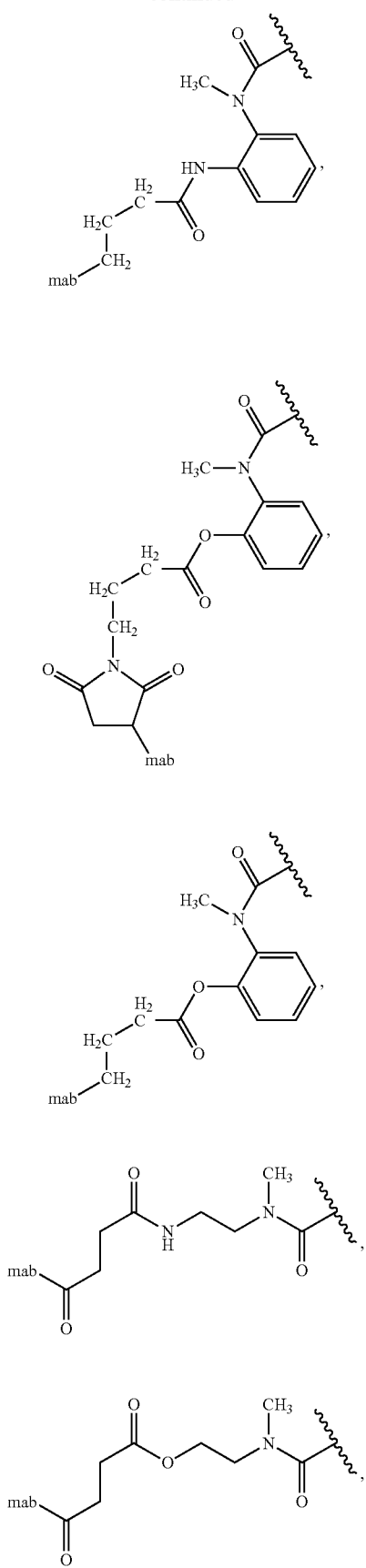
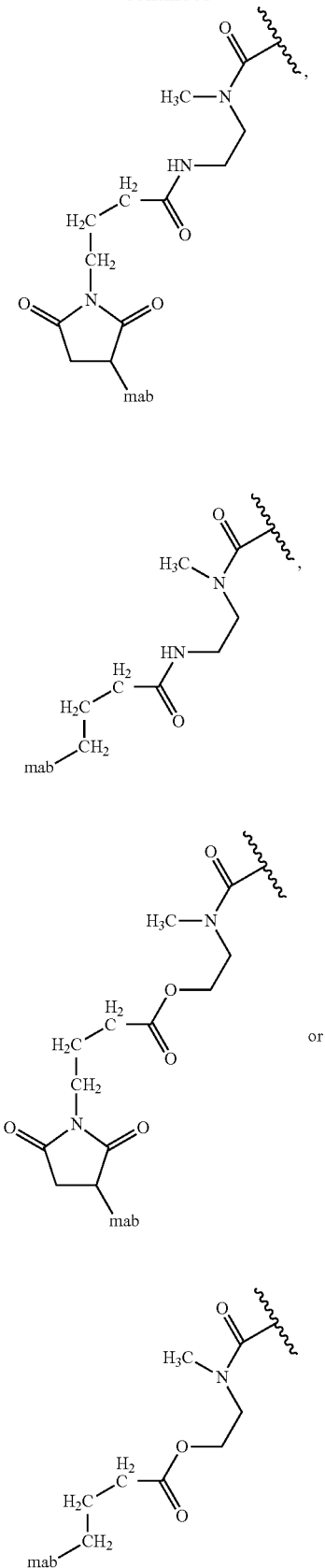
wherein mab is a monoclonal antibody.

Another specific value for Z is:
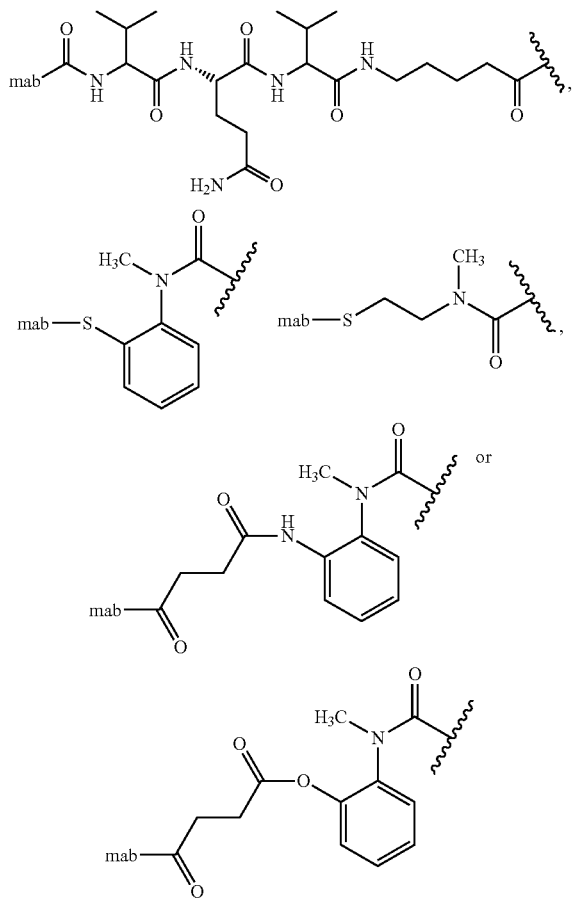
wherein mab is a monoclonal antibody.
Another specific value for Z is:
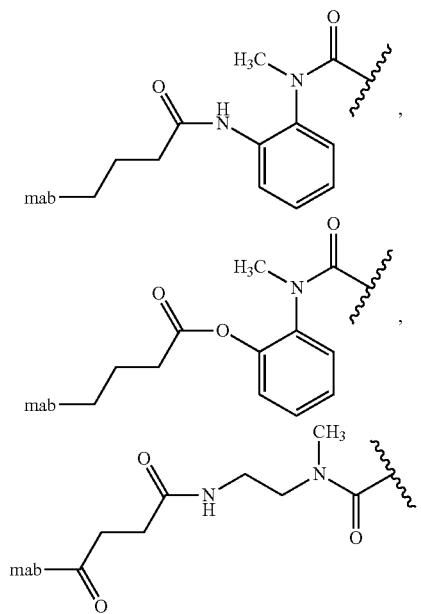
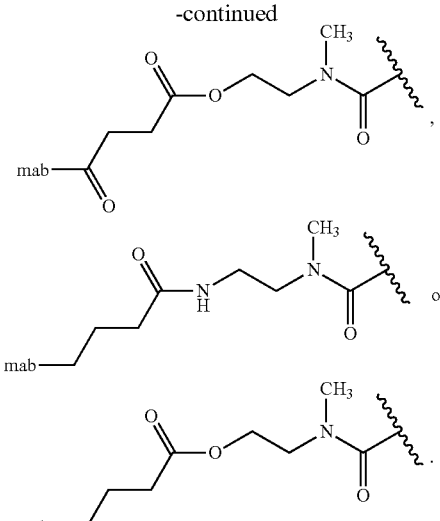
wherein mab is a monoclonal antibody.
Another specific value for Z is:
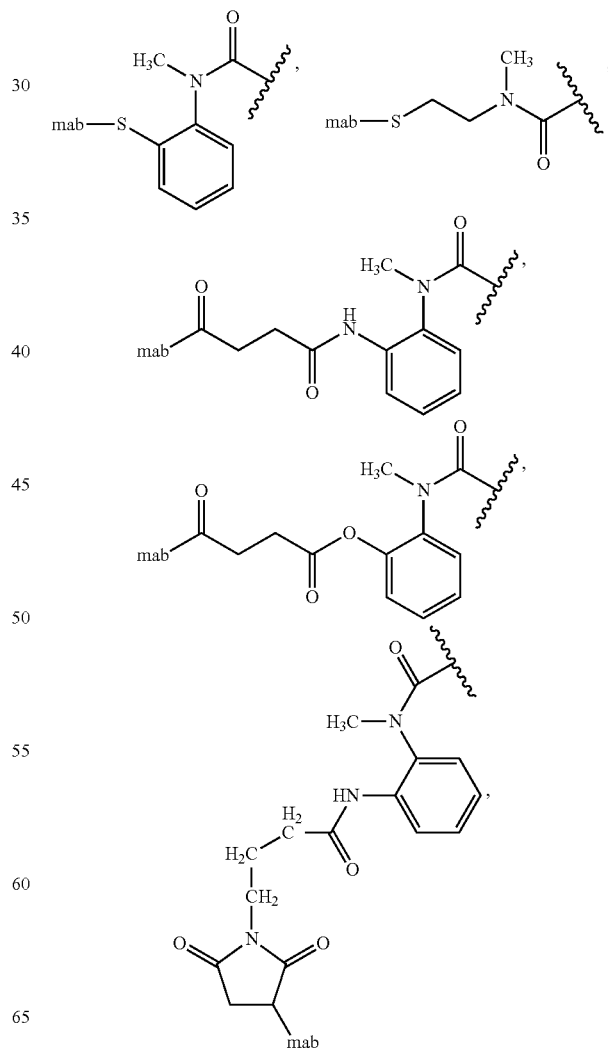

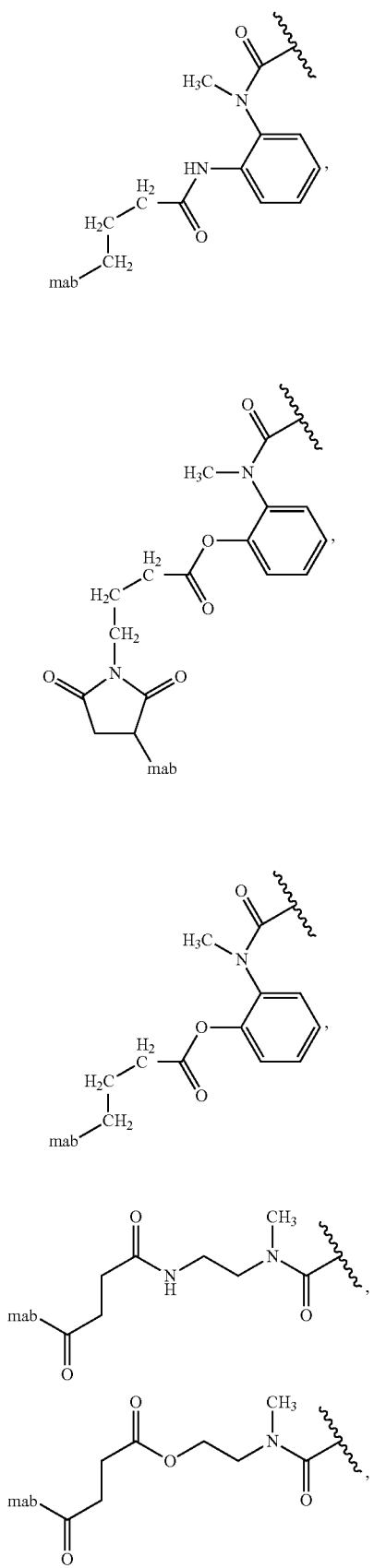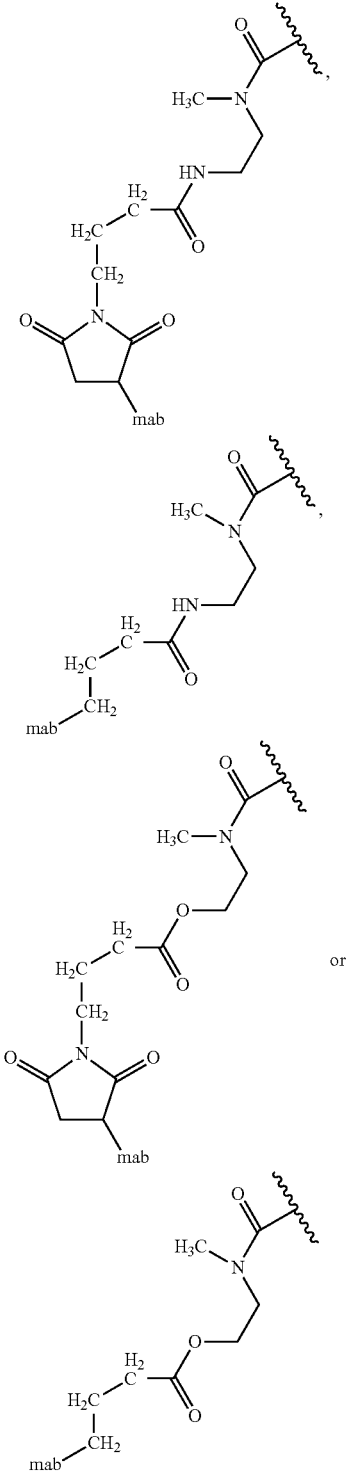

wherein mab is a monoclonal antibody.

The invention also provides for compounds of formula I wherein a single targeting moiety (e.g. mab) may be linked to one or more (e.g. 1, 2, 3, 4, 5, 6, 7, 8, 9 or 10) compounds of formula I. In general targeting moieties (e.g. mab) have a plurality of functional groups amenable to forming bonds with a plurality of reactive functional groups. Accordingly, the invention provides for compounds of formula I wherein a single targeting moiety (e.g. mab) may be linked to one or more (e.g. 1, 2, 3, 4, 5, 6, 7, 8, 9 or 10) compounds of formula I Another specific value for Y is:

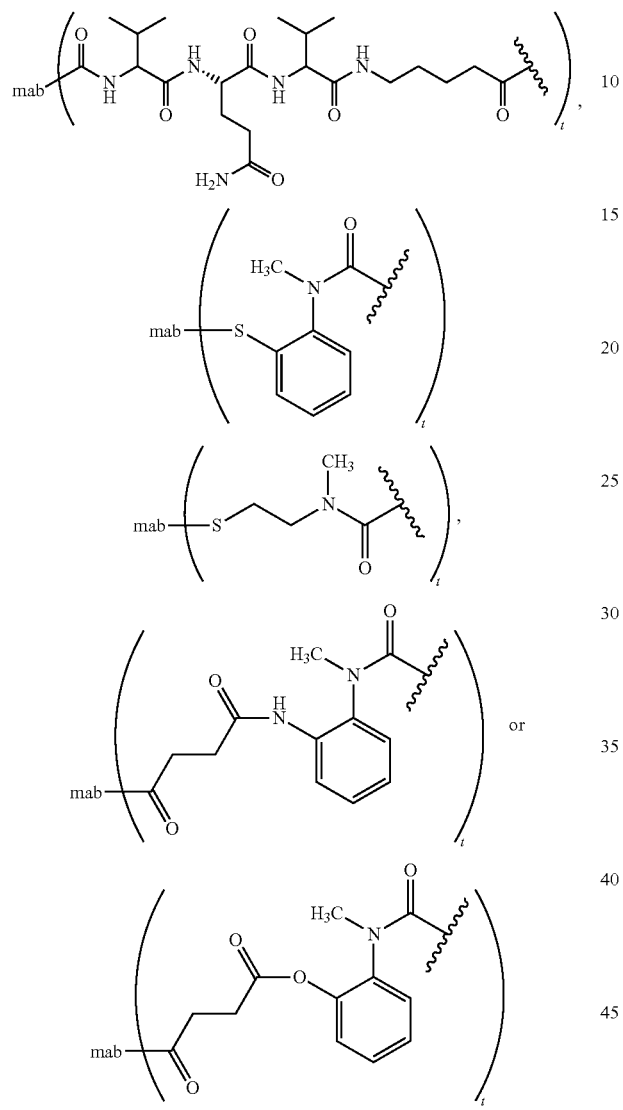

wherein mab is a monoclonal antibody, t is 1, 2, 3, 4, 5, 6, 7, 8, 9 or 10 and the wavy line is the point of attachment to the oxygen of formula I.

Another specific value for Y is:

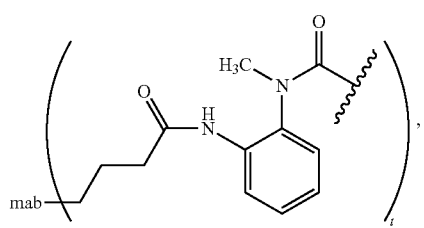

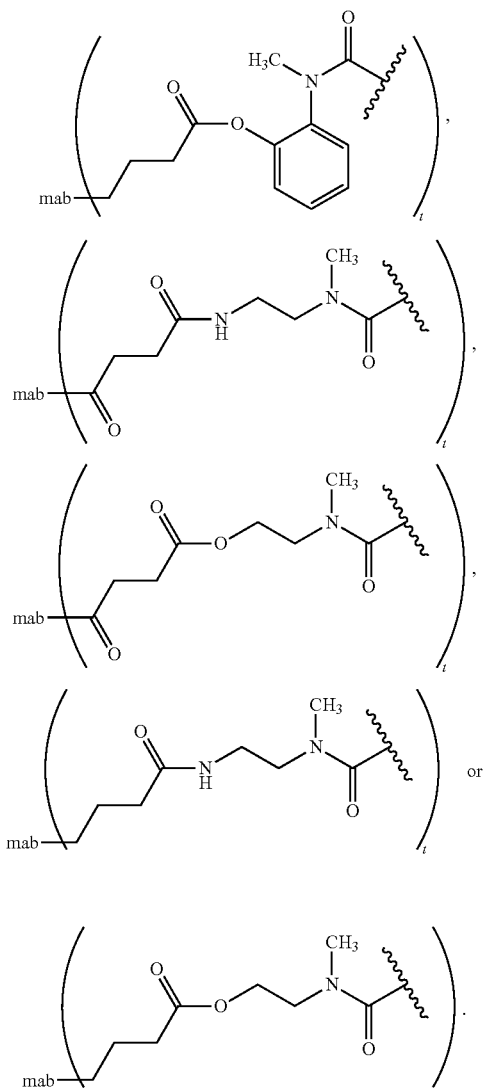

wherein mab is a monoclonal antibody, t is 1, 2, 3, 4, 5, 6, 7, 8, 9 or 10 and the wavy line is the point of attachment to the oxygen of formula I.

Another specific value for Y is:

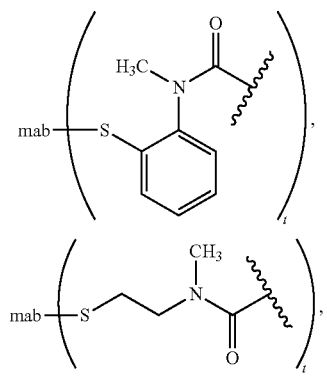

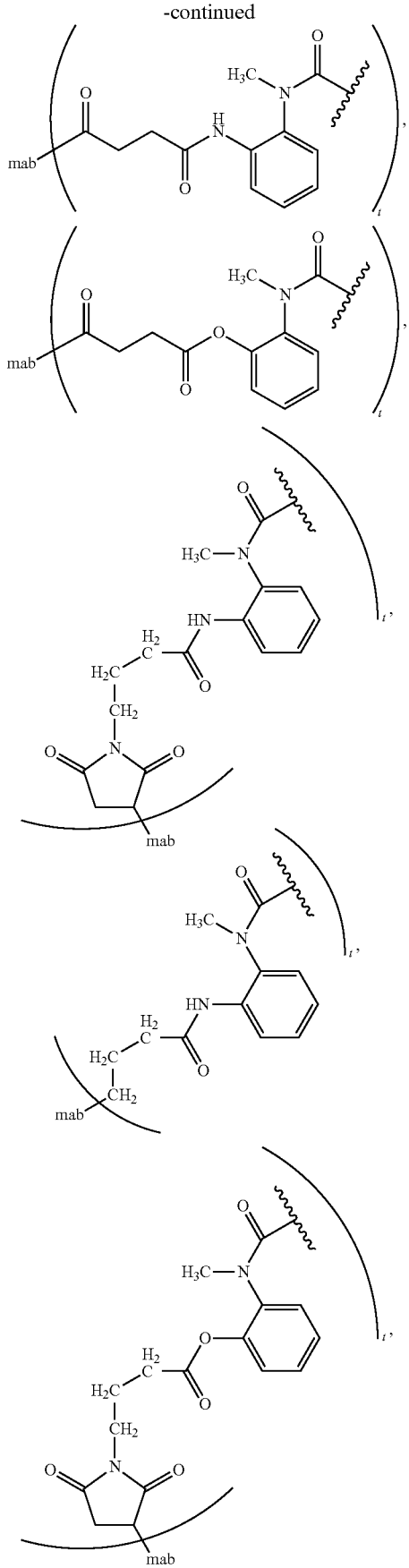
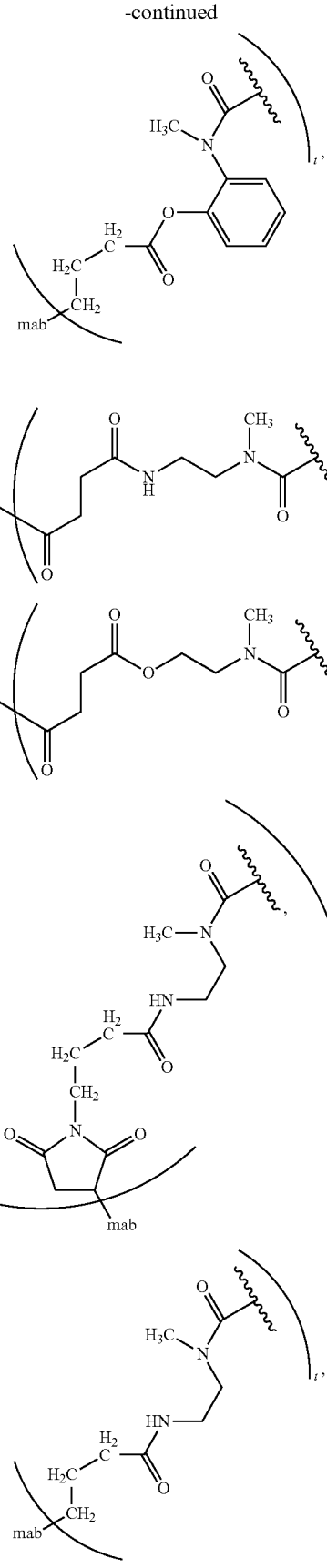

-continued
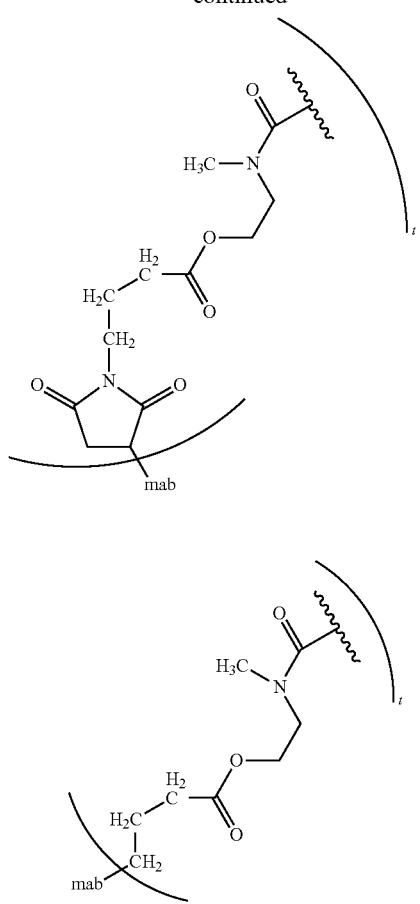
wherein mab is a monoclonal antibody, t is 1, 2, 3, 4, 5, 6, 7, 8, 9 or 10 and the wavy line is the point of attachment to the oxygen of formula I.
Another specific value for Z is:
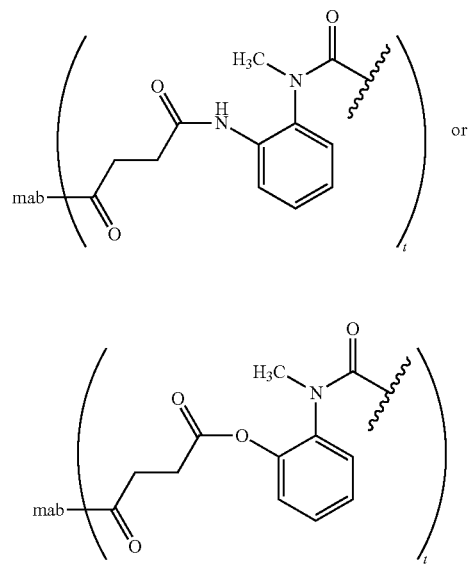
wherein mab is a monoclonal antibody, t is 1, 2, 3, 4, 5, 6, 7, 8, 9 or 10 and the wavy line is the point of attachment to the oxygen of formula I.
Another specific value for Z is:
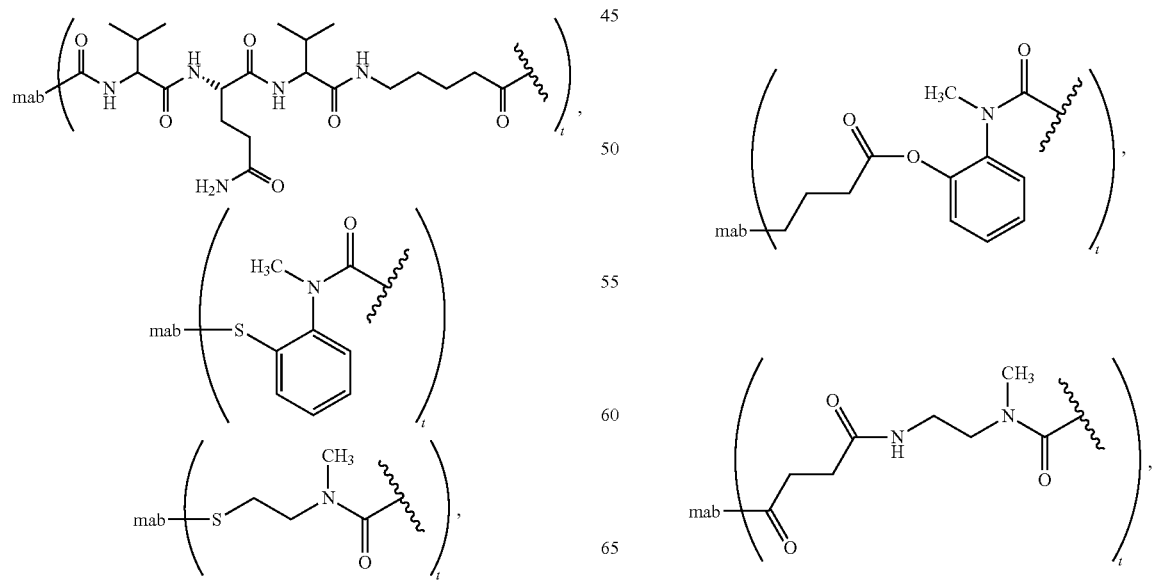

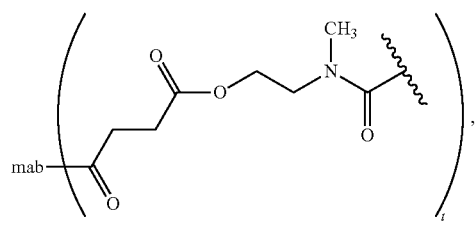
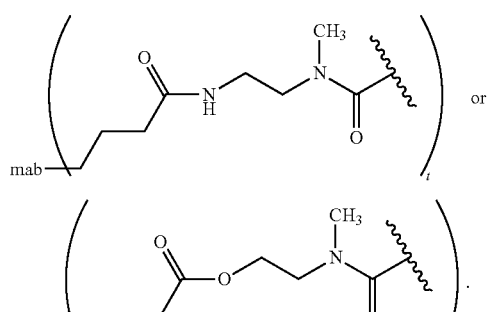
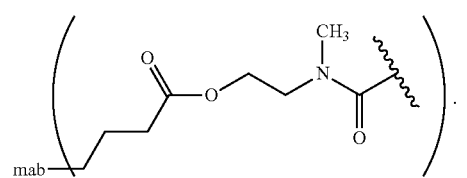
wherein mab is a monoclonal antibody, t is 1, 2, 3, 4, 5, 6, 7, 8, 9 or 10 and the wavy line is the point of attachment to the oxygen of formula I.
Another specific value for Z is:
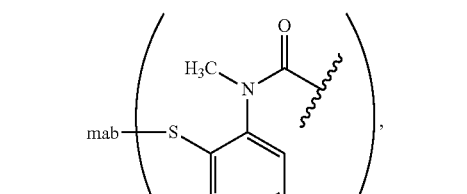
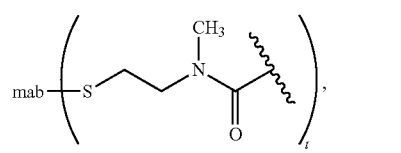
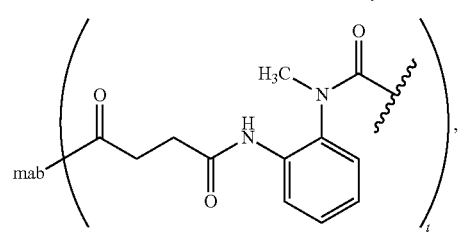
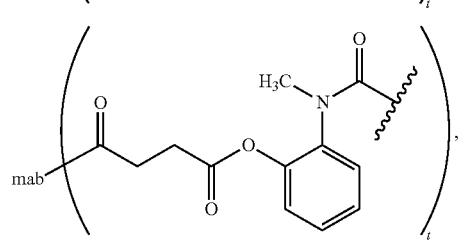
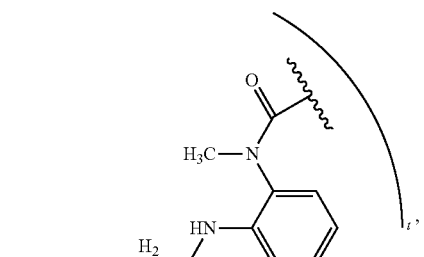
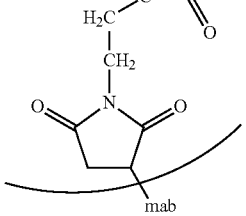
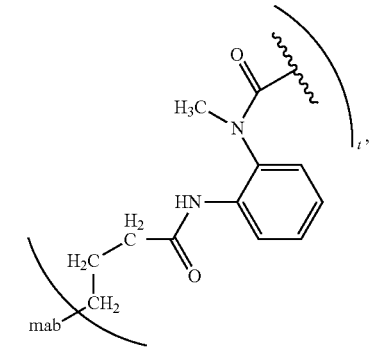
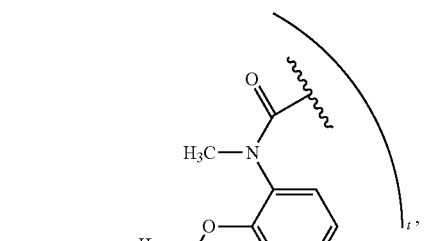
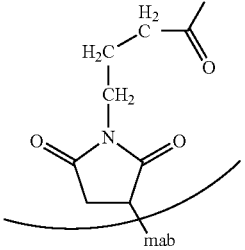
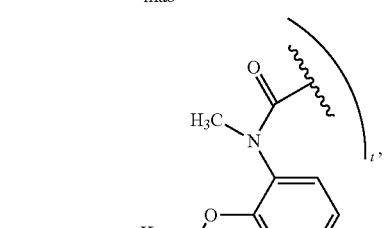

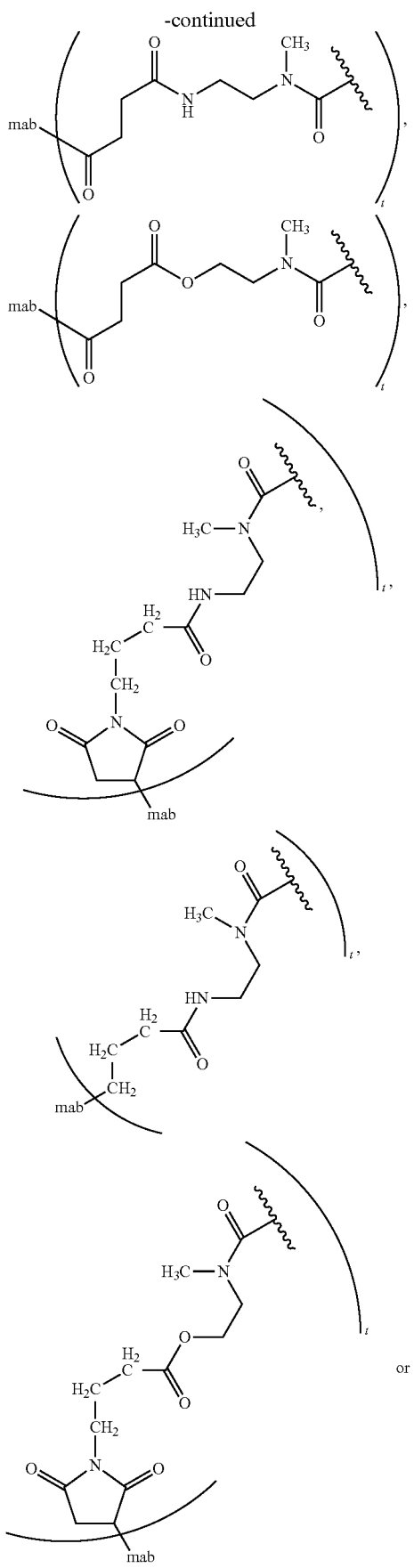

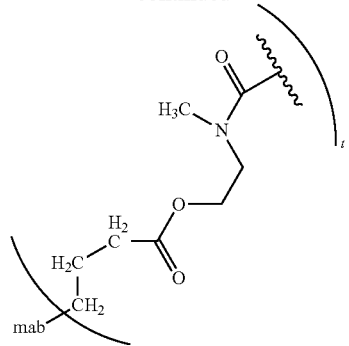

wherein mab is a monoclonal antibody, t is 1, 2, 3, 4, 5, 6, 7, 8, 9 or 10 and the wavy line is the point of attachment to the oxygen of formula I.

Another specific value for Y is a linker substituted with a targeting moiety:

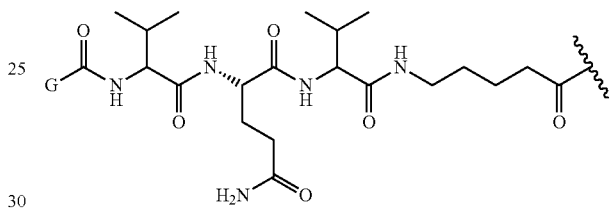

wherein G is a protein wherein the protein is capable of binding to tumor cell membranes, tumor cell receptors, and/or capable of being internalized into tumor cells.

Another specific value for Y is a linker substituted with a targeting moiety:

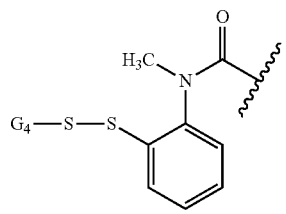

wherein $G_4$ is a protein comprising a cysteine amino acid wherein the protein comprising a cysteine amino acid is capable of binding to tumor cell membranes, tumor cell receptors, and/or capable of being internalized into tumor cells.

Another specific value for Y is a linker substituted with a targeting moiety:

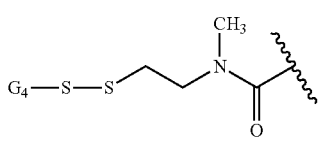

wherein $G_4$ is a protein comprising a cysteine amino acid wherein the protein comprising a cysteine amino acid is capable of binding to tumor cell membranes, tumor cell receptors, and/or capable of being internalized into tumor cells.

Another specific value for Y is a linker substituted with a targeting moiety:

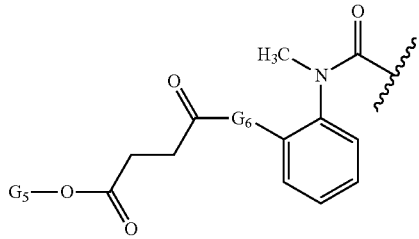

wherein $G_5$ is a monoclonal antibody and $G_6$ is NH or O.

Another specific value for Y is a linker substituted with a targeting moiety:

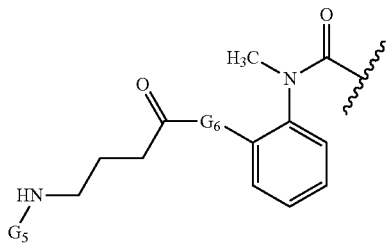

wherein $G_5$ is a monoclonal antibody and $G_6$ is NH or O.

Another specific value for Y is a linker substituted with a targeting moiety:

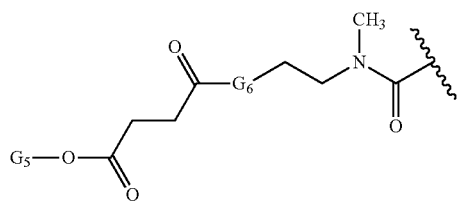

wherein $G_5$ is a monoclonal antibody and $G_6$ is NH or O.

Another specific value for Y is a linker substituted with a targeting moiety:

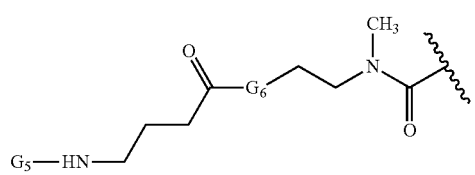

wherein $G_5$ is a monoclonal antibody and $G_6$ is NH or O.

Another specific value for Z is a linker substituted with one or more (e.g. 1, 2 or 3) targeting moieties.

Another specific value for Z is a linker substituted with a targeting moiety:

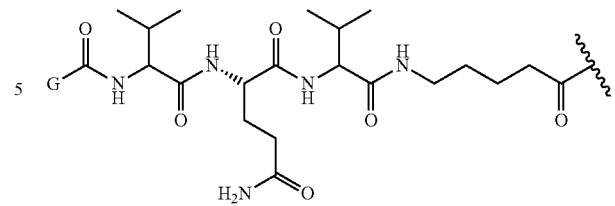

wherein G is a protein.

Another specific value for Z is a linker substituted with a targeting moiety:

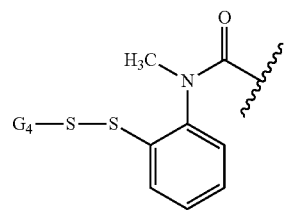

wherein $G_4$ is a protein comprising a cysteine amino acid wherein the protein comprising a cysteine amino acid is capable of binding to tumor cell membranes, tumor cell receptors, and/or capable of being internalized into tumor cells.

Another specific value for Z is a linker substituted with a targeting moiety:

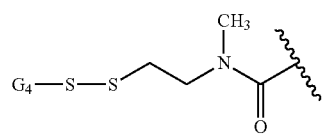

wherein $G_4$ is a protein comprising a cysteine amino acid wherein the protein comprising a cysteine amino acid is capable of binding to tumor cell membranes, tumor cell receptors, and/or capable of being internalized into tumor cells.

Another specific value for Z is a linker substituted with a targeting moiety:

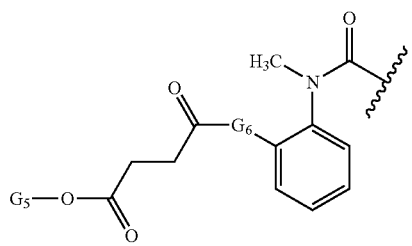

wherein $G_5$ is a monoclonal antibody and $G_6$ is NH or O.

Another specific value for Z is a linker substituted with a targeting moiety:

wherein G$_5$ is a monoclonal antibody and G$_6$ is NH or O.

Another specific value for Z is a linker substituted with a targeting moiety:

wherein G$_5$ is a monoclonal antibody and G$_6$ is NH or O.

Another specific value for Z is a linker substituted with a targeting moiety:

wherein G$_5$ is a monoclonal antibody and G$_6$ is NH or O.

A specific compound of formula I is a compound of formula II:

II

Another specific compound of formula I is a compound of formula III:

III

Another specific compound of formula I is a compound of formula IV:

IV

Another specific compound of formula I is a compound of formula V:

V

Another specific compound of formula I is a compound of formula VI:

VI

Another specific compound of formula I is a compound of formula VII:

VII

Another specific compound of formula I is a compound of formula VIII:

VIII

Another specific compound of formula I is a compound of formula IX:

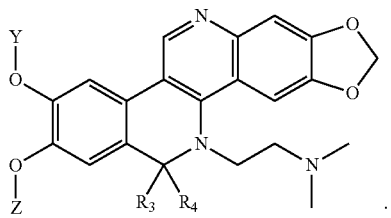

Another specific compound of formula I is any of the above compounds of formulas II-IX as their pharmaceutically acceptable salts.

Another specific compound of formula I is a compound of formula X:

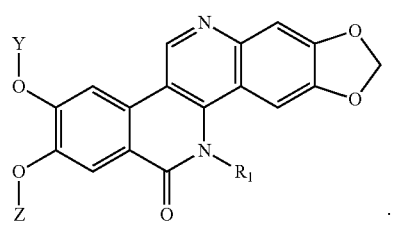

Another specific compound of formula I is a compound of formula X as a pharmaceutically acceptable salt.

A specific compound of the invention is the compound:
(2-(dimethylamino)ethyl)-9-methoxy-2,3-methylenedioxy-6-oxo-5,6-dihydrodibenzo[c,h][1,6]naphthyridin-8-yl benzoate,
5-(2-(dimethylamino)ethyl)-9-methoxy-2,3-methylenedioxy-6-oxo-5,6-dihydrodibenzo[c,h][1,6]naphthyridin-8-yl 2-methylbenzoate,
5-(2-(dimethylamino)ethyl)-9-methoxy-2,3-methylenedioxy-6-oxo-5,6-dihydrodibenzo[c,h][1,6]naphthyridin-8-yl acetate,
5-(2-(dimethylamino)ethyl)-9-methoxy-2,3-methylenedioxy-6-oxo-5,6-dihydrodibenzo[c,h][1,6]naphthyridin-8-yl pivalate,
5-(2-(dimethylamino)ethyl)-9-methoxy-2,3-methylenedioxy-6-oxo-5,6-dihydrodibenzo[c,h][1,6]naphthyridin-8-yl (3-cyclopentyl)propionate,
5-(2-(dimethylamino)ethyl)-9-methoxy-2,3-methylenedioxy-6-oxo-5,6-dihydrodibenzo[c,h][1,6]naphthyridin-8-yl ethyl carbonate,
tert-butyl 5-(2-(dimethylamino)ethyl)-9-methoxy-2,3-methylenedioxy-6-oxo-5,6-dihydrodibenzo[c,h][1,6]naphthyridin-8-yl carbonate,
5-(2-(dimethylamino)ethyl)-9-methoxy-2,3-methylenedioxy-6-oxo-5,6-dihydrodibenzo[c,h][1,6]naphthyridin-8-yl ethylcarbamate,
5-(2-(dimethylamino)ethyl)-9-methoxy-2,3-methylenedioxy-6-oxo-5,6-dihydrodibenzo[c,h][1,6]naphthyridin-8-yl dimethylcarbamate; or
5-(2-(dimethylamino)ethyl)-9-methoxy-2,3-methylenedioxy-6-oxo-5,6-dihydrodibenzo[c,h][1,6]naphthyridin-8-yl 1,4'-bipiperidine-1'-carboxylate;
or a salt thereof.

In one embodiment, a compound of the invention is a compound of formula I:

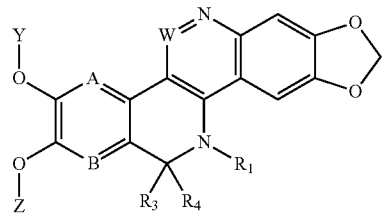

wherein:
A and B are independently N or CH;
W is N or CH;
$R_3$ and $R_4$ are each independently H, $(C_1-C_6)$alkyl, or substituted $(C_1-C_6)$alkyl, or $R_3$ and $R_4$ together are =O, =S, =NH or =N—$R_2$;
at least one of Y and Z is aryl($C_1-C_6$)alkanoyl, heteroaryl($C_1-C_6$)alkanoyl, a self-immolative moiety, a cascading prodrug moiety or a linker substituted with one or more (e.g. 1, 2 or 3) targeting moieties and the other is hydrogen, $(C_1-C_6)$alkyl, substituted $(C_1-C_6)$alkyl, $(C_1-C_6)$alkanoyl, substituted $(C_1-C_6)$alkanoyl, —C(=O)NR$_c$R$_d$, aryl($C_1-C_6$)alkanoyl or heteroaryl($C_1-C_6$)alkanoyl, wherein any aryl($C_1-C_6$)alkanoyl or heteroaryl($C_1-C_6$)alkanoyl may be optionally substituted with one or more (e.g. 1, 2, 3 or 4) groups independently selected from halo, cyano, $(C_1-C_6)$alkyl, carboxy, $NO_2$, hydroxy, $(C_1-C_6)$alkoxy and —NR$_e$R$_f$;
$R_1$ is a $(C_1-C_6)$alkyl substituted with one or more solubilizing groups;
$R_2$ is $(C_1-C_6)$alkyl or substituted $(C_1-C_6)$alkyl;
$R_c$ and $R_d$ are each independently H, $(C_1-C_6)$alkyl or substituted $(C_1-C_6)$alkyl; or $R_c$ and $R_d$ together with the nitrogen to which they are attached form a piperazino, pyrrolidino, or piperidino ring, which ring can optionally be substituted with one or more aryl, heteroaryl, or heterocycle; and
$R_e$ and $R_f$ are each independently H, $(C_1-C_6)$alkyl or substituted $(C_1-C_6)$alkyl; or $R_e$ and $R_f$ together with the nitrogen to which they are attached form a piperazino, pyrrolidino, or piperidino ring, which ring can optionally be substituted with one or more aryl, heteroaryl, or heterocycle;
or a pharmaceutically acceptable salt thereof.

In one specific embodiment of the invention, for a compound of formula I, Y is not H when Z is ($C_1$-$C_6$)alkyl; and Y is not ($C_1$-$C_6$)alkyl when Z is H.

In another specific embodiment of the invention, for a compound of formula I, Y and Z are not each independently selected from H, ($C_1$-$C_6$)alkyl, substituted ($C_1$-$C_6$)alkyl, ($C_1$-$C_6$)alkanoyl, substituted ($C_1$-$C_6$)alkanoyl, —P(=O)(OH)$_2$, and —C(=O)NR$_{ca}$R$_{da}$; wherein R$_{ca}$ and R$_{da}$ are each independently ($C_1$-$C_6$)alkyl or substituted ($C_1$-$C_6$)alkyl; or R$_{ea}$ and R$_{da}$ together with the nitrogen to which they are attached form a N'-{($C_1$-$C_6$)alkyl}piperazino, pyrrolidino, or piperidino ring, which ring can optionally be substituted with one or more aryl, heteroaryl, or heterocycle; wherein substituted alkyl is an alkyl group wherein one or more (e.g. 1 or 2) carbon atoms in the alkyl chain have been replaced with a heteroatom independently selected from —O—, —S— and NR— (where R is hydrogen or $C_1$-$C_6$alkyl) and/or wherein the alkyl group is substituted with from 1 to 5 substituents independently selected from cycloalkyl, substituted cycloalkyl, ($C_1$-$C_6$)alkoxycarbonyl (e.g. —CO$_2$Me), cyano, halo, hydroxy, oxo (=O), carboxy (COOH), aryloxy, heteroaryloxy, heterocyclooxy, nitro, and —NR$^{aa}$R$^{bb}$, wherein R$^{aa}$ and R$^{bb}$ may be the same or different and are chosen from hydrogen, alkyl, arylalkyl, heteroarylalkyl, heterocycloalkyl, cycloalkyl, substituted cycloalkyl, aryl, heteroaryl and heterocyclic; and wherein substituted alkanoyl is an alkanoyl group wherein one or more (e.g. 1 or 2) carbon atoms in the alkyl chain have been replaced with a heteroatom independently selected from —O—, —S— and NR— (where R is hydrogen or $C_1$-$C_6$alkyl) and/or wherein the alkyl group is substituted with from 1 to 5 substituents independently selected from cycloalkyl, substituted cycloalkyl, ($C_1$-$C_6$) alkoxycarbonyl (e.g. —CO$_2$Me), cyano, halo, hydroxy, oxo (=O), carboxy (COOH), aryloxy, heteroaryloxy, heterocyclooxy, nitro, and —NR$^{aa}$R$^{bb}$, wherein R$^{aa}$ and R$^{bb}$ may be the same or different and are chosen from hydrogen, alkyl, arylalkyl, heteroarylalkyl, heterocycloalkyl, cycloalkyl, substituted cycloalkyl, aryl, heteroaryl and heterocyclic.

When administered to a biological system certain compounds of the invention can function as prodrugs for corresponding compounds of the invention wherein Y and/or Z is H. The prodrugs can be converted to the corresponding compounds of the invention as a result of spontaneous chemical reaction(s), enzyme catalyzed chemical reaction(s), photolysis, and/or metabolic chemical reaction(s), or by some other process. For example, a compound of the invention such as a compound of formula I wherein Y and/or Z is aryl($C_1$-$C_6$)alkanoyl or heteroaryl($C_1$-$C_6$)alkanoyl can provide a corresponding compound of the invention wherein Y and/or Z is H following administration.

Cascading Prodrug Moiety.

As used herein the term "cascading prodrug moiety" is a moiety that is released from a compound of formula I when administered to a biological system to generate the drug substance, i.e. active ingredient, as a result of spontaneous chemical reaction(s), enzyme catalyzed chemical reaction(s), photolysis, and/or metabolic chemical reaction(s) or by some other process to provide a compound of formula I wherein at least one of X or Y is hydrogen.

In one embodiment the cascading prodrug moiety is:

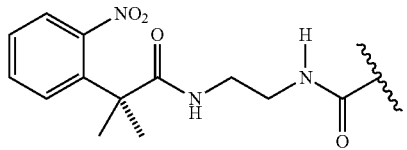

In another embodiment the cascading prodrug moiety is:

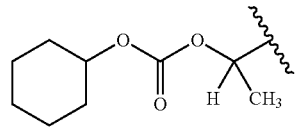

In another embodiment the cascading prodrug moiety is:

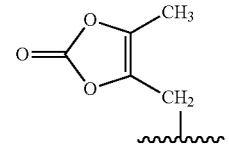

Self-Immolative Moiety.

As used herein the term "self-immolative moiety" is a moiety that is released from a compound of formula I when administered to a biological system to generate the drug substance, i.e. active ingredient, as a result of spontaneous chemical reaction(s), enzyme catalyzed chemical reaction(s), photolysis, and/or metabolic chemical reaction(s) or by some other process to provide a compound of formula I wherein at least one of X or Y is hydrogen. Several self-immolative moieties and methods for their synthesis are described in Tranoy-Opalinsky et al., Anti-Cancer Agents in Medicinal Chemistry, 2008, 8, 618-637, and in references therein.

In one embodiment the self-immolative moiety is:

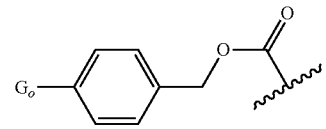

wherein G$_o$ is NH$_2$, NHOH or OH.

In another embodiment the self-immolative moiety is:

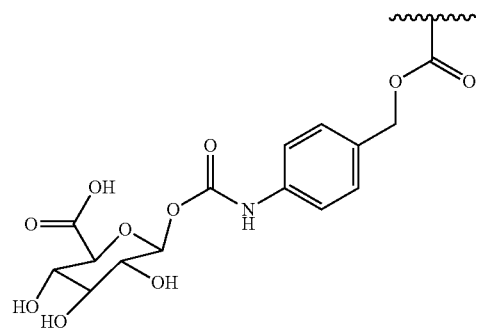

In another embodiment the self-immolative moiety is:

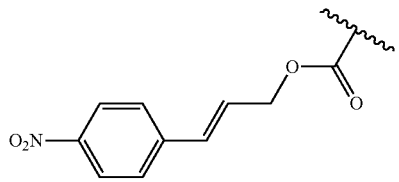

In another embodiment the self-immolative moiety is:

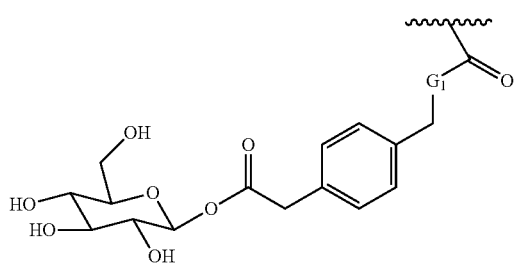

wherein $G_1$ is NH or O.

In another embodiment the self-immolative moiety is:

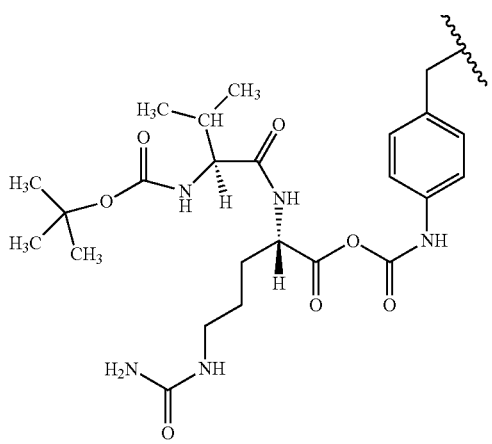

In another embodiment the self-immolative moiety is:

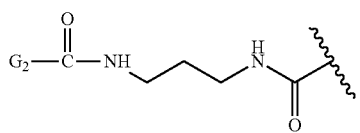

wherein $G_2$ is a peptide that is cleaved by prostate-specific antigen.

In another embodiment the self-immolative moiety is:

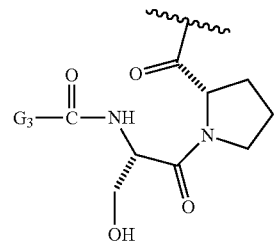

wherein $G_3$ is a peptide that is cleaved by prostate-specific antigen.

In another embodiment the self-immolative moiety is:

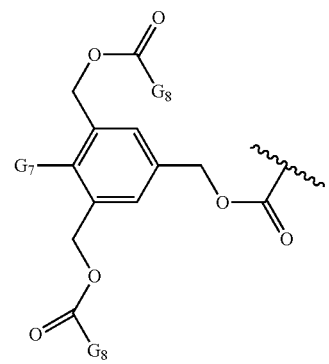

wherein $G_7$ is $NH_2$ or OH and each $G_8$ is independently a compound of the invention, such as a compound of formula 1, wherein the point of attachment is Y or Z.

In another embodiment the self-immolative moiety is:

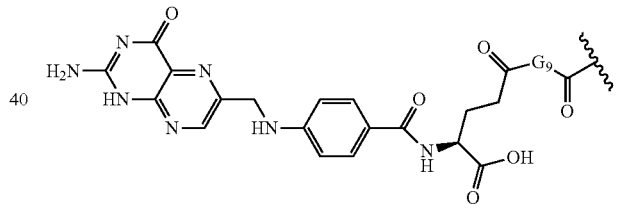

wherein $G_9$ is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—) or (—NH—) and wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, cyano, nitro, halo, hydroxy, oxo (=O), carboxy, aryl, aryloxy, heteroaryl, and heteroaryloxy.

In another embodiment the self-immolative moiety is:

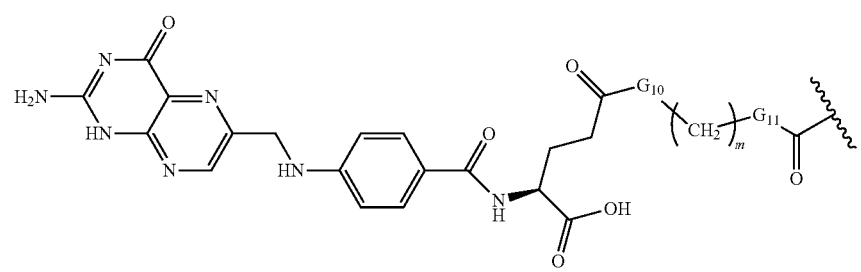

wherein $G_{10}$ and $G_{11}$ are each independently NH and O and m is 2 or 3.

Antibody-Drug Conjugates.

Antibody-drugs conjugates (ADCs) have been developed for several monoclonal antibodies (mab) that have proven selective for various human cancers. This methodology has proved to be an effective means for improving the targeting of cancer chemotherapeutic to neoplastic cells while reducing side effects. More than twenty-different monoclonal antibodies have been employed in the formation of ADCs. These monocolonal antibodies have been linked to various cytotoxic agents with the objective of improving therapeutic efficacy, while reducing systemic toxicity. Monoclonal antibodies to CD30, CD33, CD70, Her2 and CEA attached to one or more cytotoxic agents have been among the more extensively studied. The number of chemotypes of cytotoxic agents relative to the number of monoclonal antibodies that have been used to form these ADCs is less than half. Maytansinoid, taxoid, doxorubicin, auristatin, calcicheasmicin, geldamycin, streptonigrin, and camptothecin derivatives are among the more commonly selected cytotoxic agents. The number of molecules of cytotoxic agent attached to each monoclonal antibody can vary depending upon the conditions under which the linkage to the cytotoxic agent if formed. There may be as one molecule of cytotoxic agent attached per monoclonal antibody to as high as 7 or more.

Potency and metabolic stability are factors that can influence the selection of cytotoxic agent used to form the ADC. Potency is a factor as there are limits to the amount of drug that can be loaded onto a monoclonal antibody. Metabolic stability is a factor as inactivation of the cytotoxic agent by plasma enzymes would limit the amount of effective agent that would be delivered to the cancerous cell. In one embodiment the invention provides a compound of the invention which is a potent cytotoxic agent with sufficient metabolic stability and accessible functionality (e.g. phenol) for forming conjugates (via a linker) to monoclonal antibodies.

Linker:

As used herein the term "linker" includes groups that are covalently bonded to the compound of the invention. The nature of the linker is not critical provided it does not interfere with the ability of compound to inhibit topoisomerase I or II or to function as a prodrug.

In one embodiment of the invention the linker has a molecular weight of from about 20 daltons to about 400 daltons.

In another embodiment of the invention the linker has a length of about 5 angstroms to about 60 angstroms.

In another embodiment of the invention the linker separates the targeting moiety from the remainder of the compound of formula I by about 5 angstroms to about 40 angstroms, inclusive, in length.

In another embodiment of the invention the linker is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In another embodiment of the invention the linker is of the formula W-A wherein A is $(C_1-C_{24})$alkyl, $(C_2-C_{24})$alkenyl, $(C_2-C_{24})$alkynyl, $(C_3-C_8)$cycloalkyl, $(C_6-C_{10})$aryl or a combination thereof, wherein W is —N(R)C(=O)—, —C(=O)N(R)—, —OC(=O)—, —C(=O)O—, —O—, —S—, —S(O)—, —S(O)$_2$—, —N(R)—, —C(=O)—, or a direct bond; wherein each R is independently H or $(C_1-C_6)$alkyl.

In another embodiment of the invention the linker is of the formula $W^1$—$W^2$—$W^3$—$W^4$—$W^5$ wherein: $W^1$ is —C(=O)—, —C(=O)N(R)—, —C(=O)O—, —S(O)—, —S(O)$_2$— or a direct bond; $W^2$ is $(C_1-C_6)$alkyl, $(C_2-C_6)$alkenyl, $(C_2-C_6)$alkynyl, $(C_3-C_8)$cycloalkyl or $(C_6-C_{10})$aryl or a combination thereof; $W^3$ is —N(R)C(=O)—, —C(=O)N(R)—, —OC(=O)—, —C(=O)O—, —O—, —S—, —S(O)—, —S(O)$_2$—, —C(=O)—, —N(R)—, or is absent; $W^4$ is $(C_1-C_6)$alkyl, $(C_2-C_6)$alkenyl, $(C_2-C_6)$alkynyl, $(C_3-C_8)$cycloalkyl or $(C_6-C_{10})$aryl or a combination thereof or is absent; and $W^5$ is —N(R)C(=O)—, —C(=O)N(R)—, —OC(=O)—, —C(=O)O—, —O—, —S—, —S(O)—, —S(O)$_2$—, —C(=O)—, —N(R)—, succinimidyl or absent, provided that when $W^4$ is absent $W^5$ is absent; and wherein each R of $W^1$, $W^3$ or $W^5$ is independently H or $(C_1-C_6)$alkyl. It is understood that $W^1$ is the point of attachment of the linker to the compound of formula I and that any alkyl, alkenyl, alkynyl, cycloalkyl or aryl of $W^2$ or $W^4$ can be monovalent or divalent.

In another embodiment of the invention the linker is a divalent radical formed from a peptide.

In another embodiment of the invention the linker is a divalent radical formed from an amino acid.

In another embodiment of the invention the linker is a divalent radical formed from poly-L-glutamic acid, poly-L-aspartic acid, poly-L-histidine, poly-L-ornithine, poly-L-serine, poly-L-threonine, poly-L-tyrosine, poly-L-leucine, poly-L-lysine-L-phenylalanine, poly-L-lysine or poly-L-lysine-L-tyrosine.

In another embodiment of the invention the linker is of the formula W—$(CH_2)_n$ wherein, n is between about 1 and about 10; and W is —N(R)C(=O)—, —C(=O)N(R)—, —OC(=O)—, —C(=O)O—, —O—, —S—, —S(O)—, —S(O)$_2$—, —C(=O)—, —N(R)—, or a direct bond; wherein each R is independently H or $(C_1-C_6)$alkyl.

In another embodiment of the invention the linker is methylene, ethylene, or propylene.

In another embodiment of the invention the linker is:

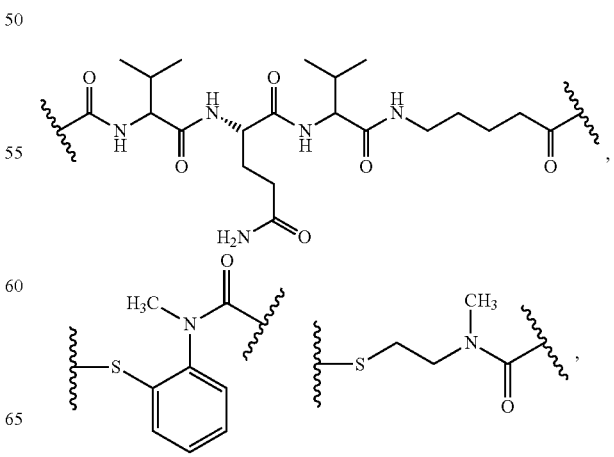

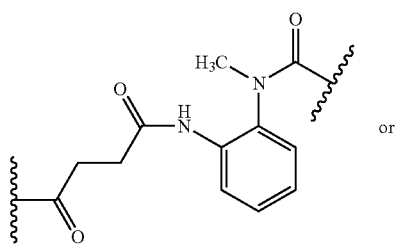
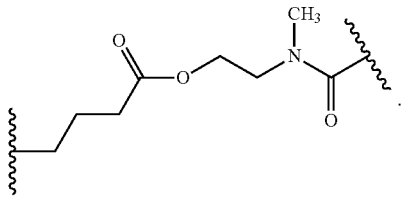
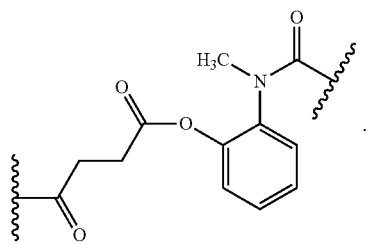
In another embodiment the linker is
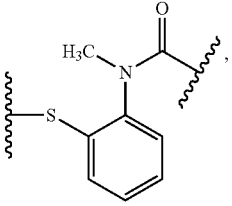 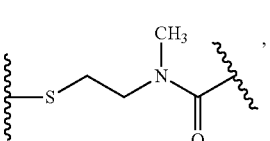
In another embodiment of the invention the linker is:
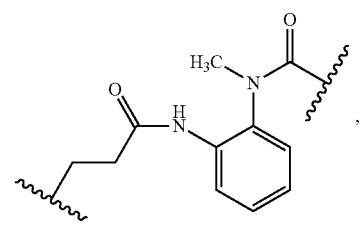
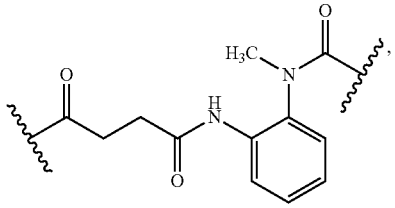
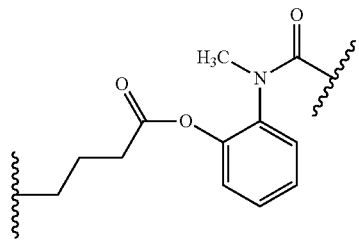
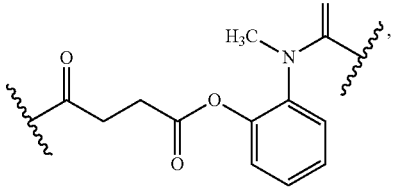
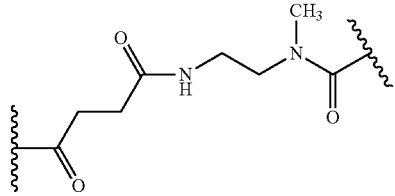
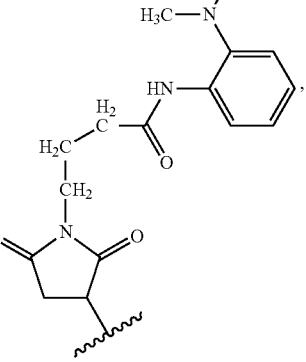
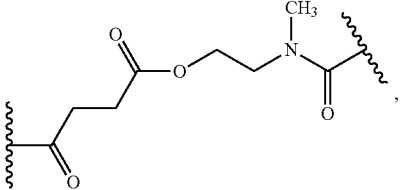
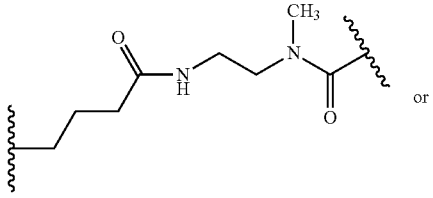 or
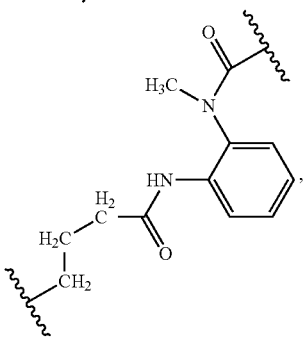

-continued

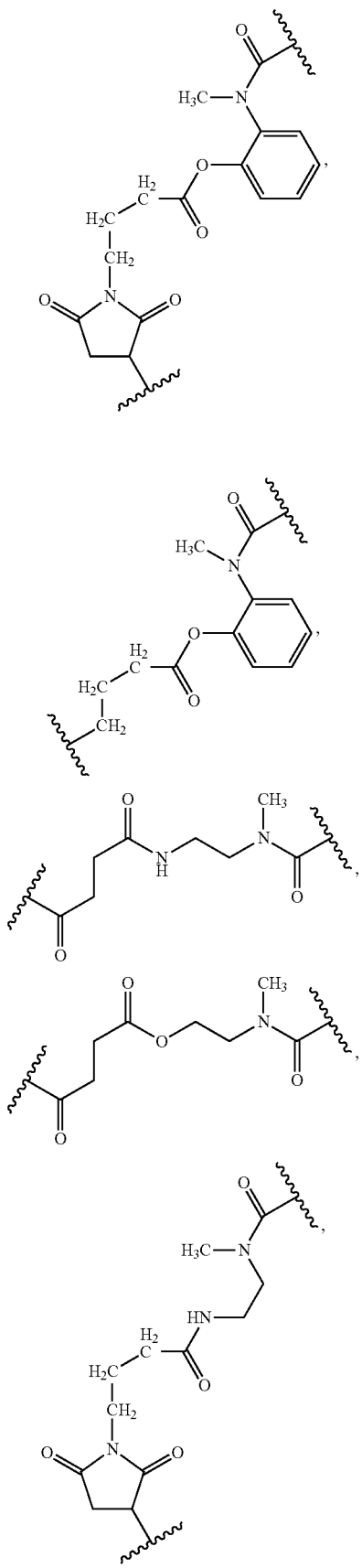

-continued

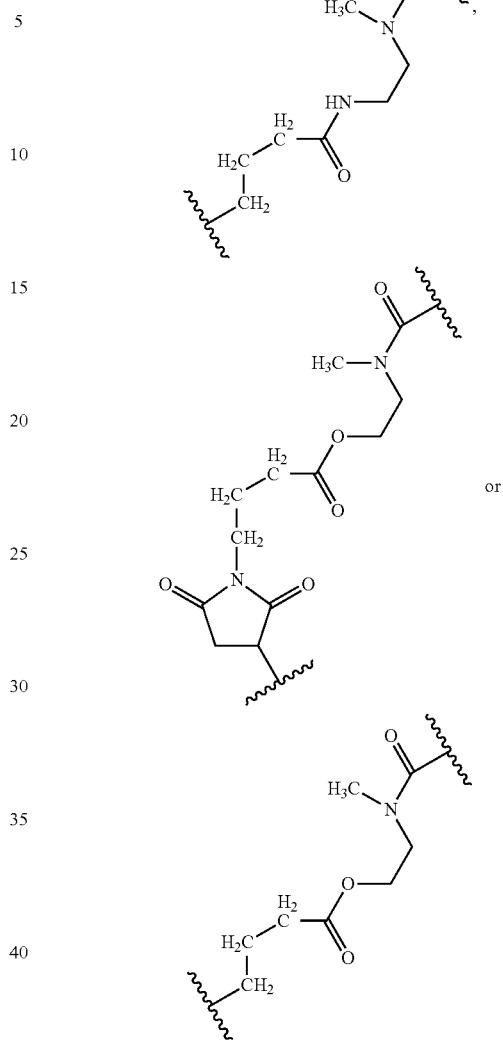

In another embodiment the linker is released from the compound of formula I when administered to a biological system to generate the drug substance, i.e. active ingredient, as a result of spontaneous chemical reaction(s), enzyme catalyzed chemical reaction(s), photolysis, and/or metabolic chemical reaction(s) or by some other process. In another embodiment the linker is not released from the compound of formula I when administered to a biological system. In one embodiment the compound of formula I that is released from the linker as a result of one of the above mentioned processes is the compound of formula I wherein Y is H. In one embodiment the compound of formula I that is released from the linker as a result of one of the above mentioned processes is the compound of formula I wherein Z is H.

Targeting Moiety:

As used herein the term "targeting moiety" includes but is not limited to any moiety that can selectively target a receptor, enzyme, protein, membrane, cell, cell type (e.g. cancer cell), tissue or that can cross a biological barrier (e.g. the gut wall or the blood-brain barrier) in an assisted or unassisted fashion. Targeting moieties include but are not limited to proteins, antibodies, monoclonal antibodies, sugars and glycosylated proteins or other molecules that are known to preferentially interact with biomolecules, membranes, proteins, cells and tissues. As used herein the term "protein" comprises 21 or more amino acids.

Several purified monoclonal antibodies useful in binding to different clusters of differentiation (cell surface molecules) that are associated with various cancers have been developed. With the broad array of purified mononclonal antibodies that have been developed, ADCs developed from monoclonal antibodies to CD30, CD33, CD70, EGFR, Her2 and CEA attached to one or more cytotoxic agents have been among the more extensively studied.

In one embodiment the targeting moiety is a protein capable of binding to tumor cell membranes, tumor cell receptors, and/or capable of being internalized into tumor cells.

In another embodiment the targeting moiety is a protein that comprises a cysteine residue and is capable of binding to tumor cell membranes, tumor cell receptors, and/or capable of being internalized into tumor cells.

In another embodiment the targeting moiety is a monoclonal antibody.

In another embodiment the monoclonal antibody is an antibody to CD30, CD33, CD70, EGFR, Her2 or CEA. The following documents relate to specific monoclonal antibodies, their purification and methods for the formation of their respective antibody-drugs conjugates (1. Anti-CD30/cAC10: Sun, M. M. C., et al., *Bioconjugate Chem.*, 2005, 16, 1282-1290; McDonagh, C. F., et al., *Protein Engineering, Design & Selection*, 19, 299-307; Doronina, S. O., et al., *Nature Biotechnology*, 2003, 21, 778-784. 2. Anti-CD79b: Doronina, S. O., et al., Bioconjugate Chem., 2006, 17, 114-124; Poison, A. G., et al., *Blood*, 2007, 110, 616623. 3. Anti-CD19, Anti-CD20, Anti-CD21, Anti-CD22, Anti-CD72, Anti-CD79b, and Anti-CD-180: Poison, A. G., et al., *Cancer Res.*, 2009, 69, 2358-2364. 4. huC242: Erickson, H. K., et al., *Cancer Res.*, 2006, 66, 4426-4433; Xie, H., et al., *J. Pharmacol Exp. Ther.*, 2004, 308, 1073-1082. 5. Anti-CD30 and Anti-CD70: Burke, P. J., et al., *Bioconjugate Chem.*, 009, 20, 1242-1250. 6. Anti-CD70: Alley, S. C., et al., Bioconjugate Chem., 2008, 19, 759-765. 7. Anti-Her-2 and Anti-CD19: Chari, R V, et al., *Cancer Res.*, 1991, 52, 127-131. Lewis Phillips, G. D., et al., *Cancer Res.*, 2008, 68, 9280-9290. 8. Anti-CEACAM5: Govindan, S. V., et al., *Clin. Cancer Res.*, 2009, 15, 6052-6061).

Processes for preparing compounds of the invention including compounds of formula I are provided as further embodiments of the invention and are illustrated by the following procedures in which the meanings of the generic radicals are as given above unless otherwise qualified.

The starting materials employed in the synthetic methods described herein are commercially available, have been reported in the scientific literature, or can be prepared from readily available starting materials using procedures known in the field. It may be desirable to optionally use a protecting group during all or portions of the above described synthetic procedures. Such protecting groups and methods for their introduction and removal are well known in the art. See Greene, T. W.; Wutz, P.G.M. "Protecting Groups In Organic Synthesis" second edition, 1991, New York, John Wiley & Sons, Inc.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine topoisomerase inhibition activity or cytotoxic activity using the standard tests described herein, or using other similar tests which are well known in the art. Compounds of the present invention can contain chiral centers, for example, the carbon atom in formula I when $R_3$ and $R_4$ are different. Compounds of the present invention can also contain chiral centers, for example, in any of the substituents $Y, Z, R_1, R_2$ when $R_3$ and $R_4$ together are =N—$R_2$, and $R_3$ or $R_4$.

In cases where compounds are sufficiently basic or acidic, a salt of a compound of the invention can be useful as an intermediate for isolating or purifying a compound of the invention. Additionally, administration of a compound of the invention as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Representative compounds of the invention can be prepared as illustrated below in Schemes 1-2

Scheme 1

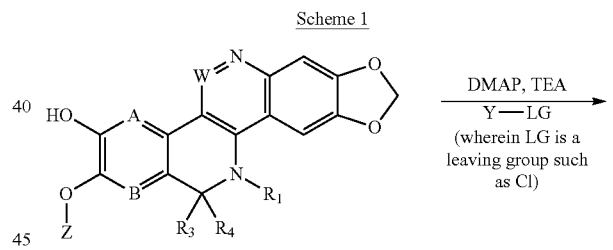

Scheme 2

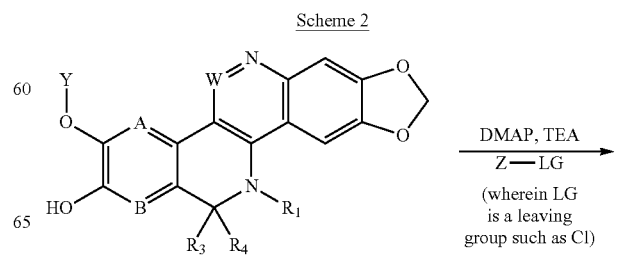

-continued

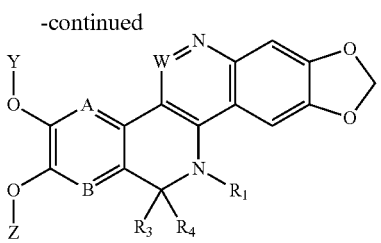

Representative compounds of the invention wherein a compound is linked to a targeting moiety can be prepared as described below and as illustrated in Schemes 3-12.

There are several standard methods for forming antibody drug conjugates (ADCs). These methods generally involve connecting a drug to an antibody through an appropriate linker. One method for accomplishing this involves attaching a "linker" to a drug. This drug-linker is then connected to an antibody. The schemes below outline several potent linker-drug fragments (i.e. fragments that comprise a compound of the invention and a "linker") bearing electrophilic or reactive (e.g. electrophilic) substituents. These substituents will interact with appropriate functional groups (e.g. thiols, alkyl amines and/or hydroxyl groups) of antibodies (e.g. monoclonal antibodies) to form ADCs. Thiol addition products that result in the formation of either thioethers or disulfides have been shown to particularly useful in forming effective ADCs. Various methods have generally allowed for linking between 1 to 8 drug molecules per monoclonal antibody. Accordingly, the invention provides for the linking of one or more (e.g. 1, 2, 3, 4, 5, 6, 7, 8, 9, 10 or more) compounds of the invention to an antibody (e.g. monoclonal antibody) through a "linker".

Controlled reduction of purified monoclonal antibody disulfides exposes free thiol groups which are capable of interacting with a reactive group of the "linker". In certain instances the amount to dithiothreitol is limited to allow for fewer thiol groups to be available for interaction with the linker. Using 3.25 and 2.75 molar equivalents of the strong reducing agents dithiothritol DTT and tris(2-carboxyethyl] phosphine TCEP have been used to reduce interchain disulfide bonds to provide free thiols. Partial reduction using the weaker reducing agent aminoethanethiol at pH 5 has been accomplished 500 molar equivalents. TCEP react poorly with maleimides and the excess of this reducing agent does not have to be removed before adding maleimide-containing dug linkers. In addition to partial reduction, a fully reduced monoclonal antibody can be partially re-oxidized with 5,5'-dithio-bis-(2-nitrobenzoic acid) DTNB. The extent of reduction can be determined by assaying a portion of the reduction mixture by initial purification through a PD-10 column and titrating the number of antibody-cysteine thiols with 5,5'-dithio-bis(2-nitrobenzoic acid).

The drug-linker can be added to an appropriate solvent (e.g. ethanol, dimethylacetamide) wherein the resulting solution or mixture can be added to the reduced antibody. For example, the reduced antibodies in a 0.1 M phosphate buffer, pH 7.0, containing 2 mM EDTA, and the drug-linker are typically allowed to react for 1-20 hours at 0-20° C. Excess and/or unreacted drug-linker can then be quenched with an appropriate reagent such as N-acetylcysteine. Gel filtration over a PD-10 column will remove the quenched drug linker. The resulting ADC can at this point be filter-sterilized.

The ADC reaction mixture can be loaded on a hydroxyapatite column equilibrated with 10 mM sodium phosphate pH 7.0, 10 mM NaCl. After washing with several column volumes of the same buffer, the ADC is typically eluted with 100 mM phosphate, pH 7.0 and 10 mM NaCl. The ADCs can be concentrated and buffer-exchanged into PBS using Amicon Ultrafree centrifugal filter units. The ADC thus formed can be subjected to hydrophobic interaction (RP-HPLC) chromatography in some instances to isolate conjugates with different ratios of drug/antibody.

The methods depicted in Schemes 3-12 start from known or commercially available compounds and the reaction steps utilize known reagents and known reaction conditions. The term "mab" represents a monoclonal antibody. The methods outlined in Schemes 3-12 show a specific compound of formula A (compound A1) being converted to an ADC, however, these methods can be also be used to convert a compound of formula A or a compound of formula B to an ADC.

Formula A

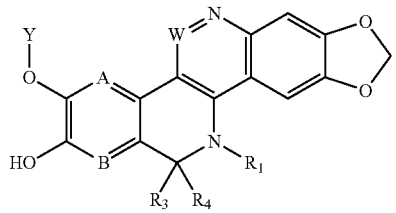

Formula B

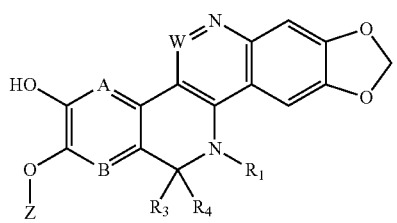

compound A1

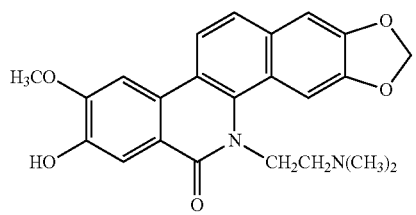

Scheme 3

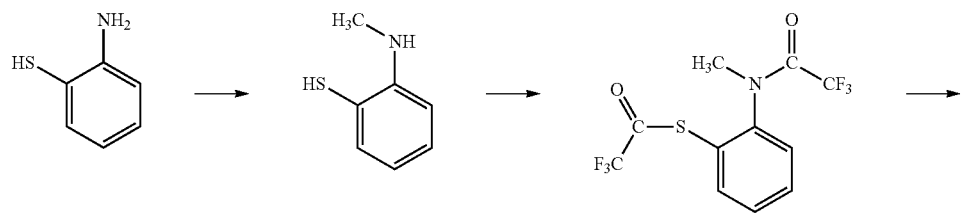

-continued
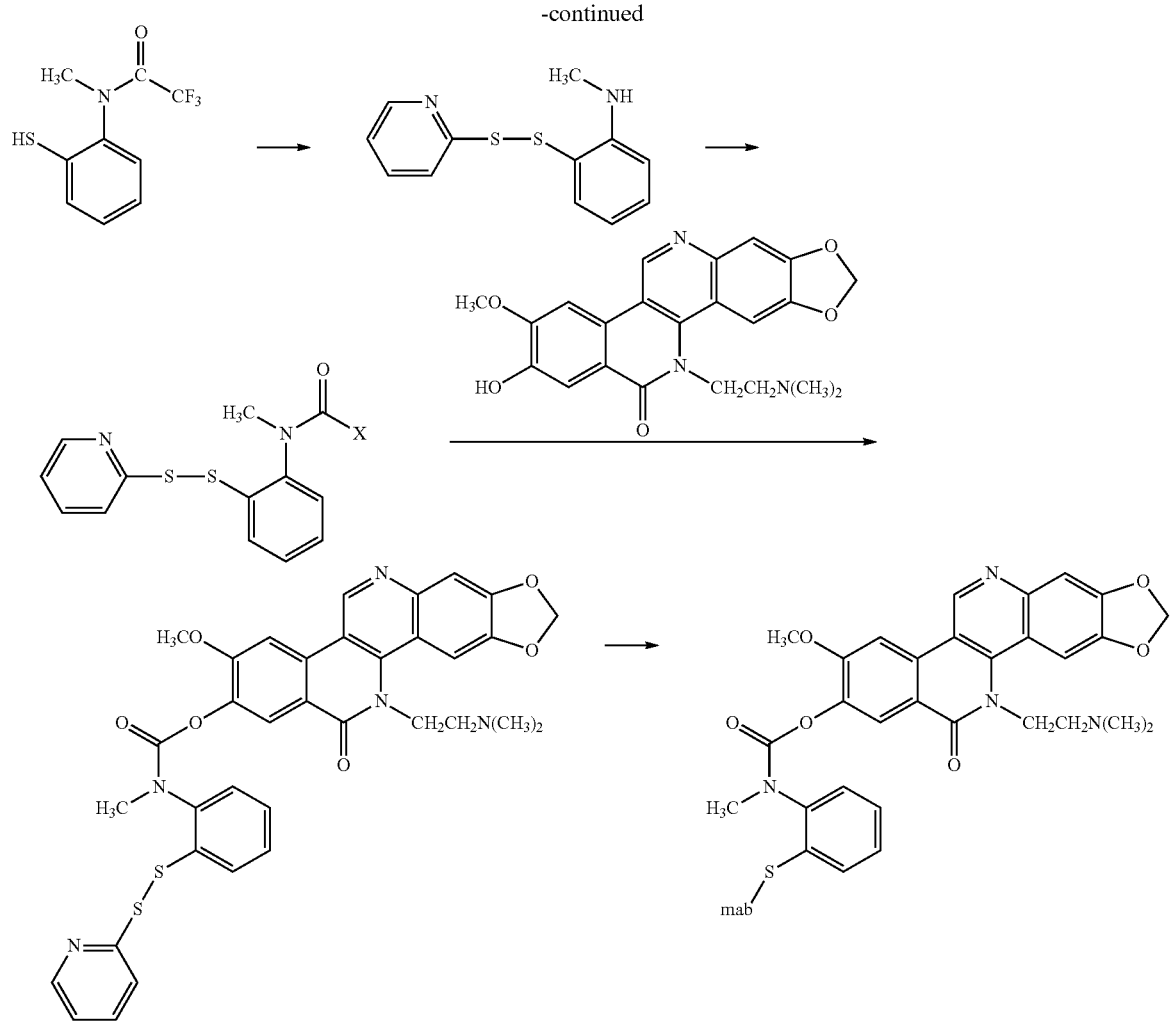
X = is a leaving group such as chloro or p-nitrophenoxy
Scheme 4
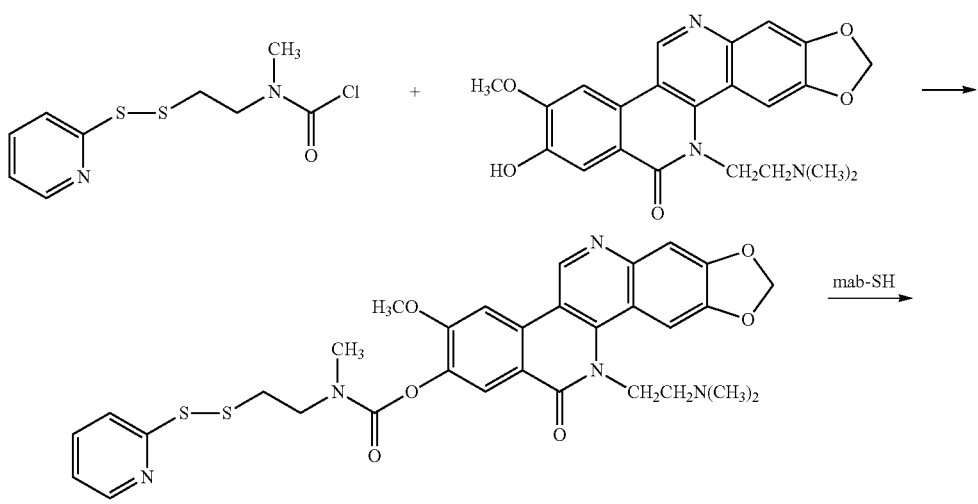

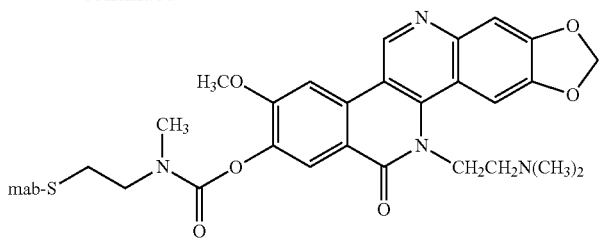
Scheme 5
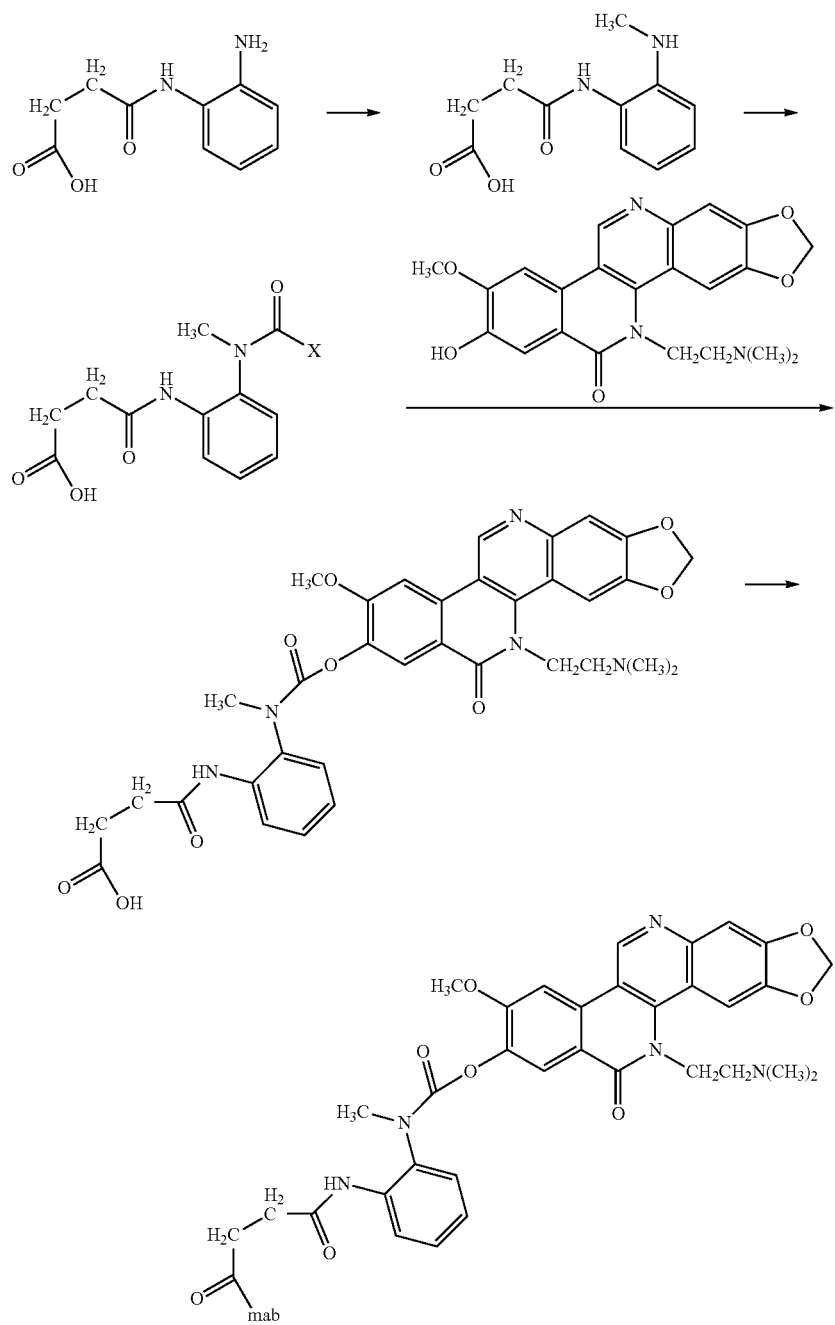
X = is a leaving group such as chloro or p-nitrophenoxy Scheme 6
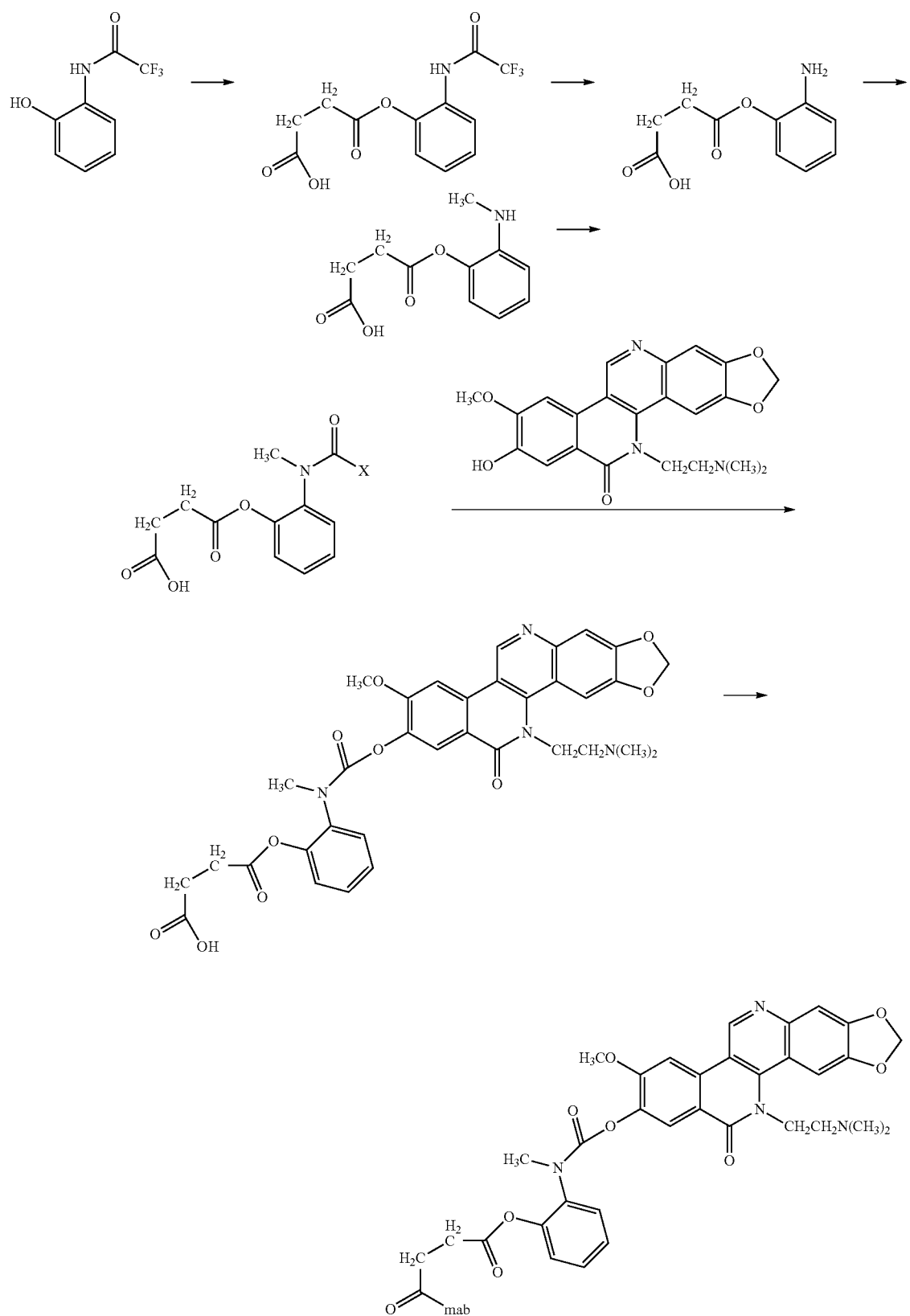
X = is a leaving group such as chloro or p-nitrophenoxy

71          72
Scheme 7
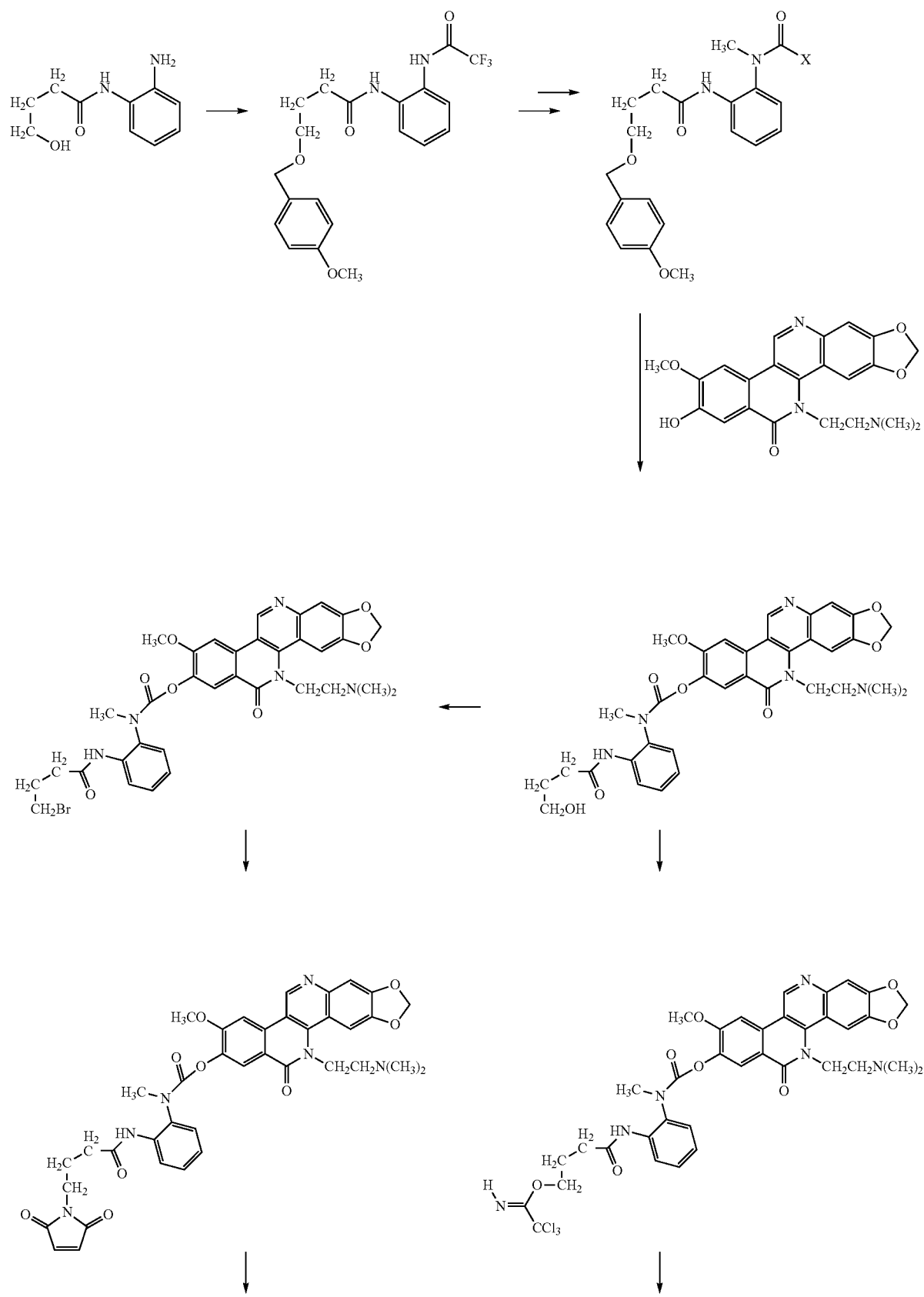

-continued
73
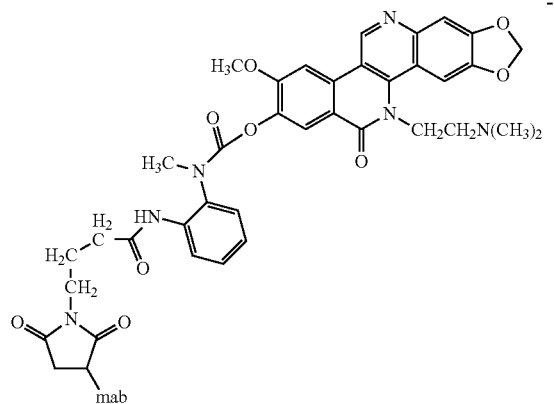
74
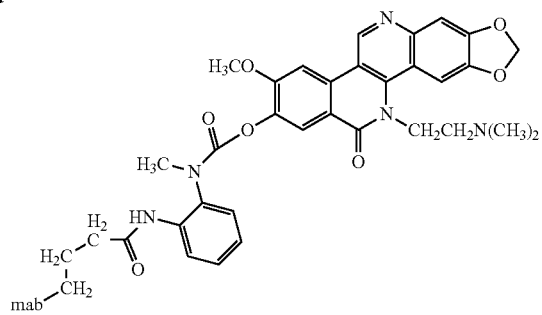
X = is a leaving group such as chloro or p-nitrophenoxy Scheme 8
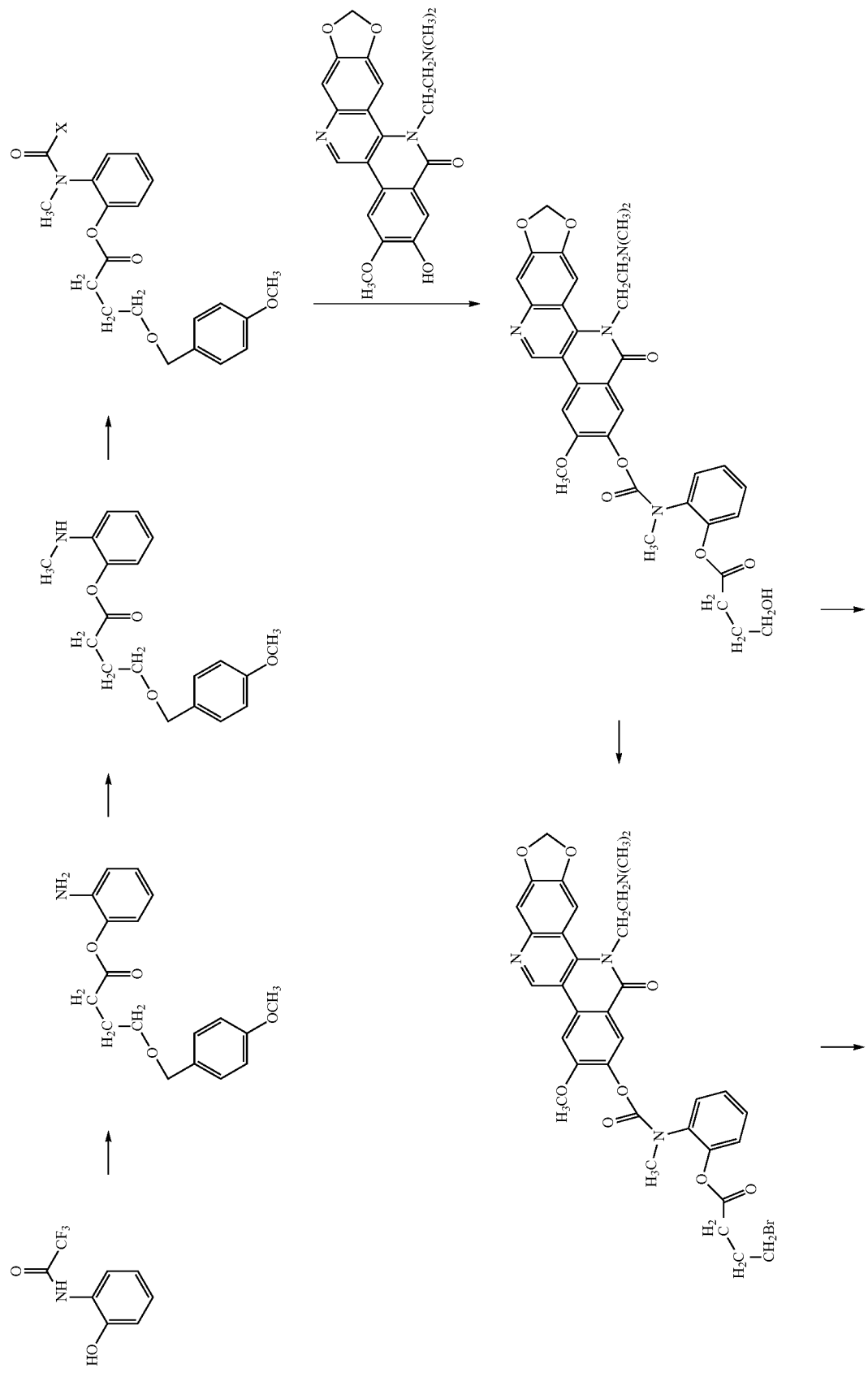

-continued
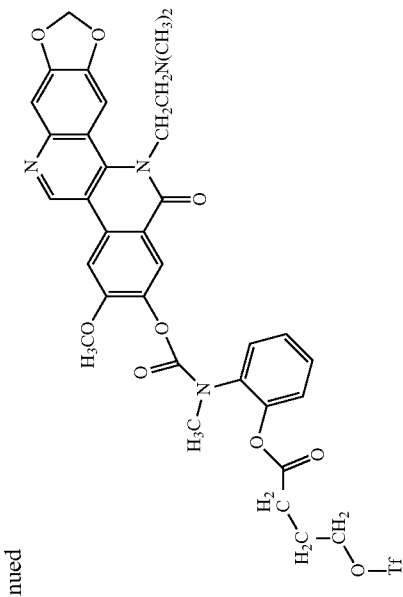  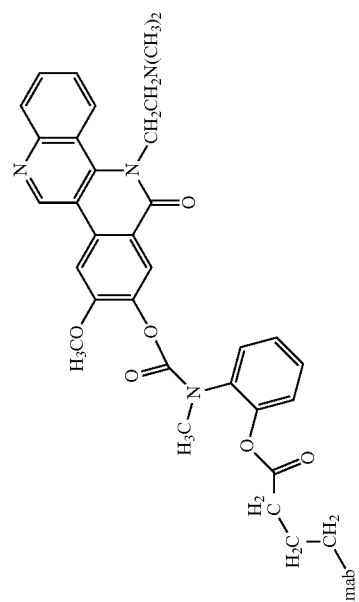
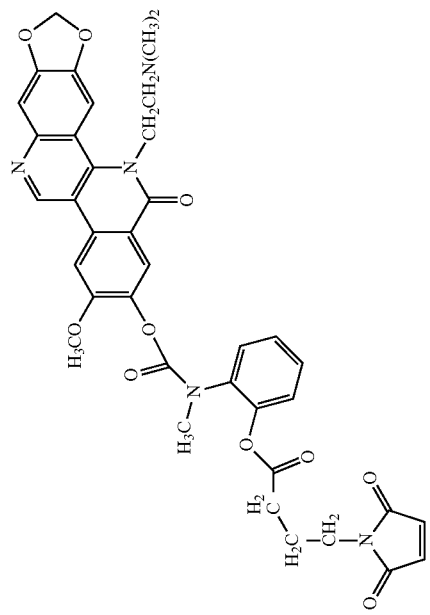  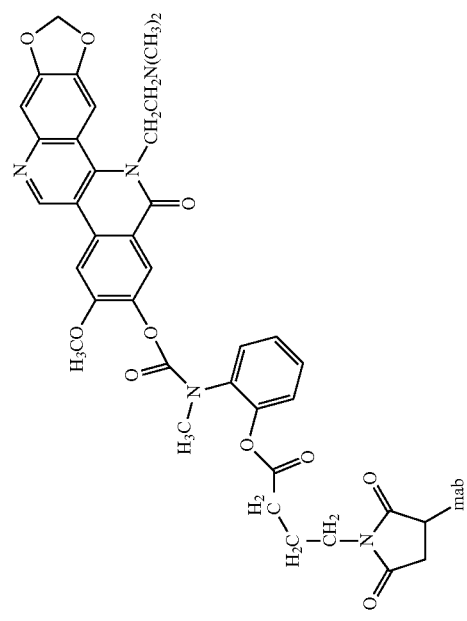
X = is a leaving group such as chloro or p-nitrophenoxy

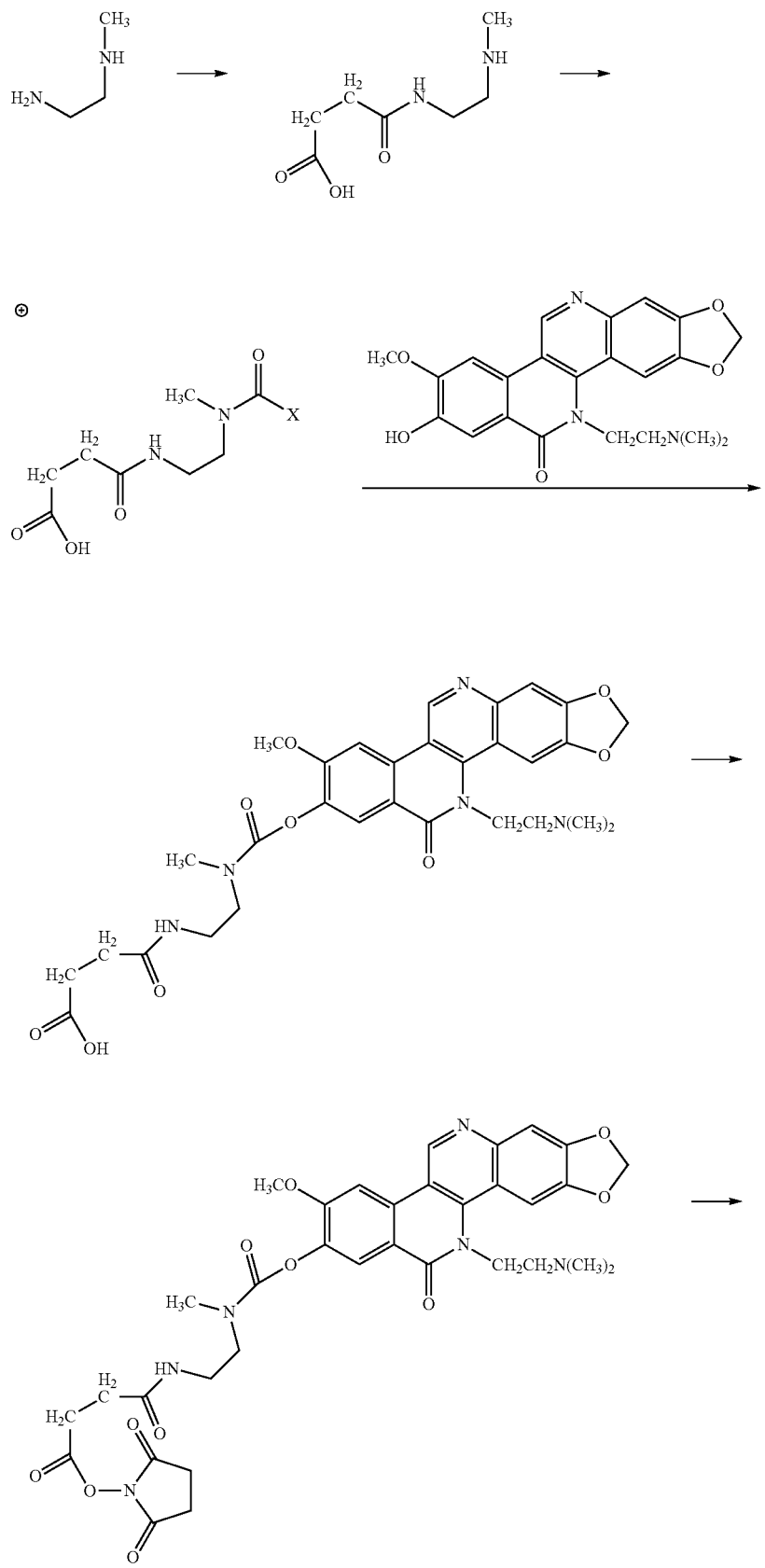

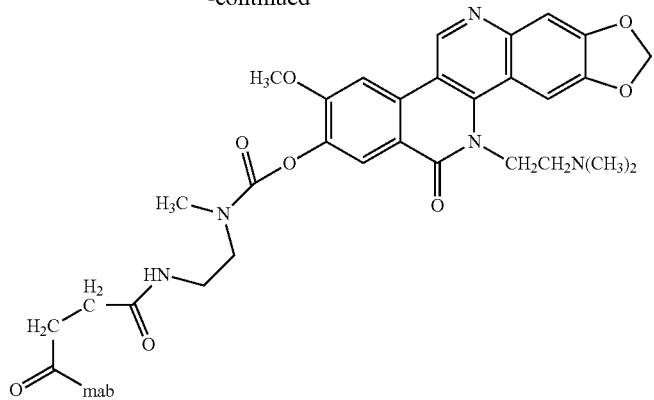
X = is a leaving group such as chloro or p-nitrophenoxy
Scheme 10
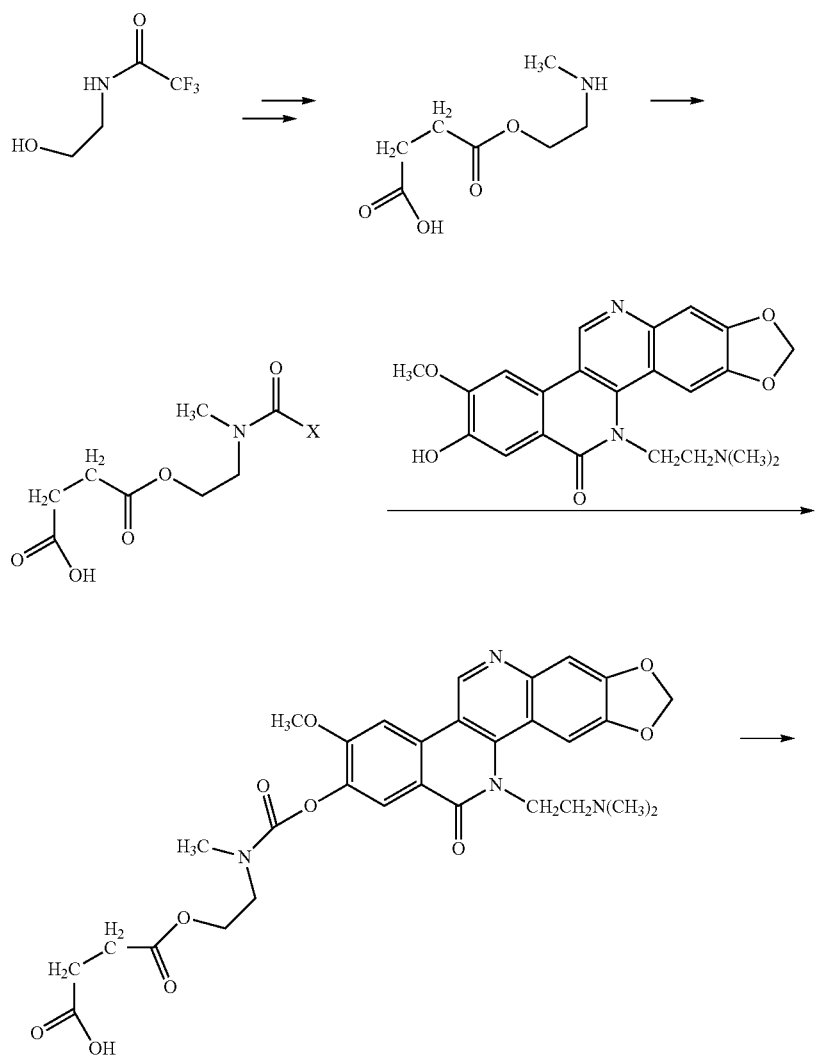

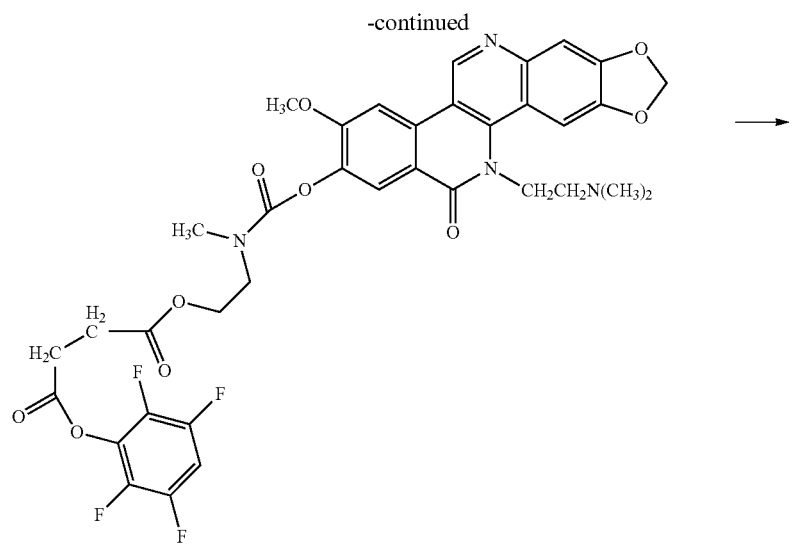
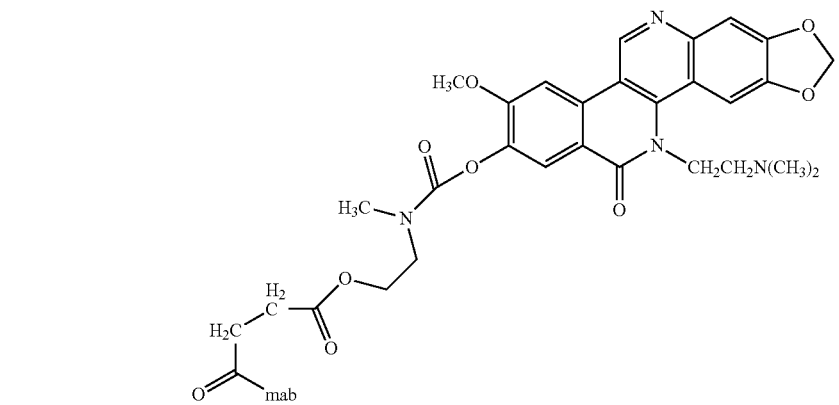
X = is a leaving group such as chloro or p-nitrophenoxy
Scheme 11
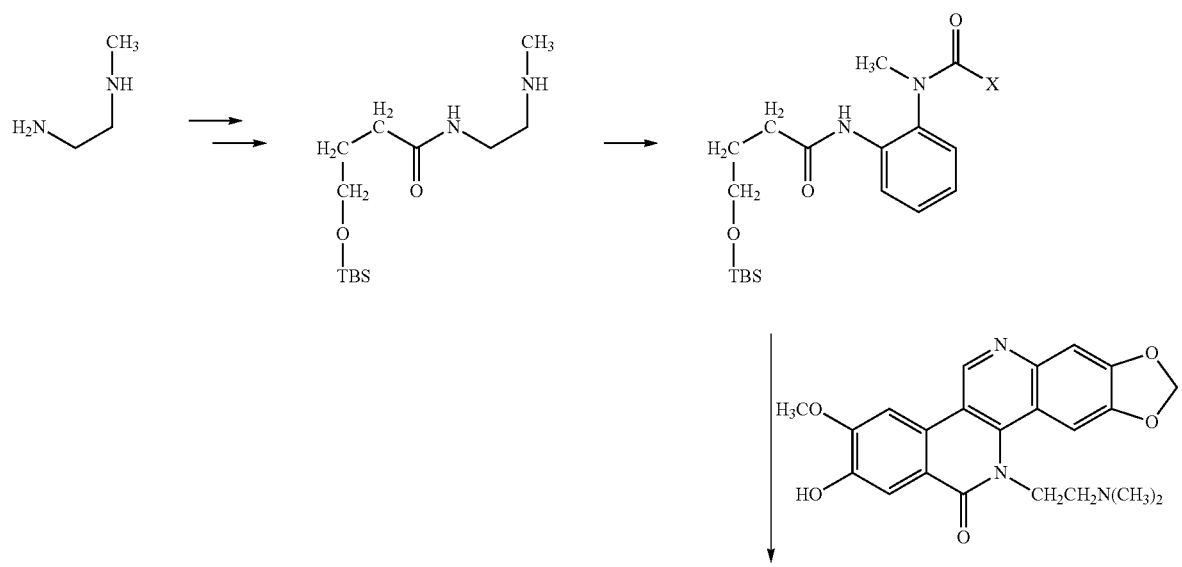

85
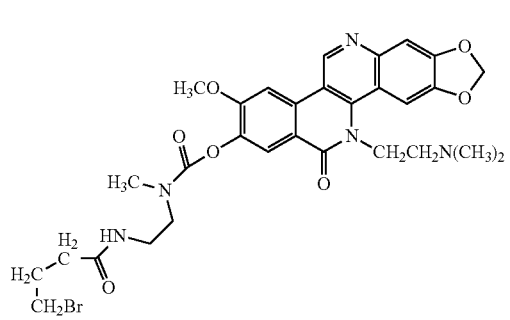
86
-continued
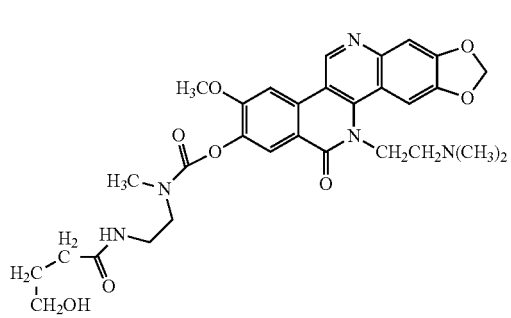
↓
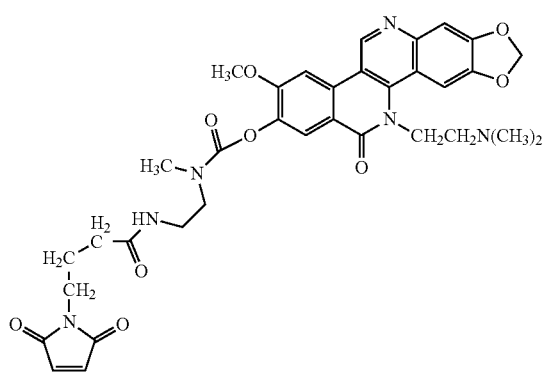
↓
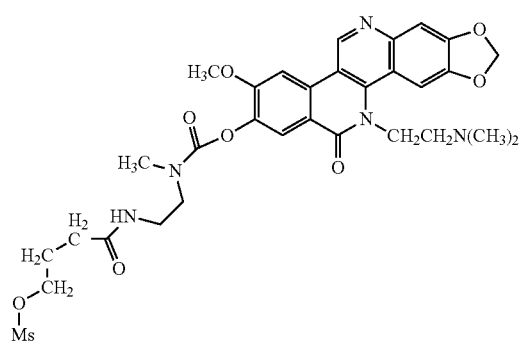
↓
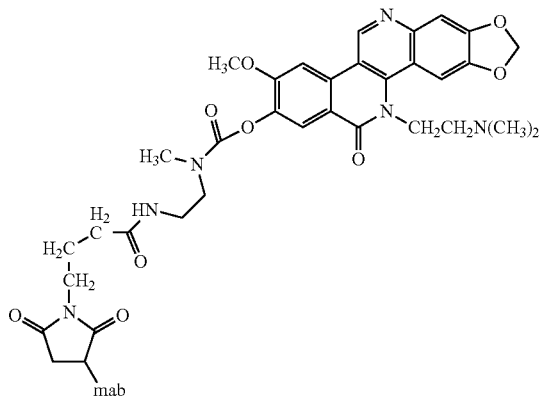
↓
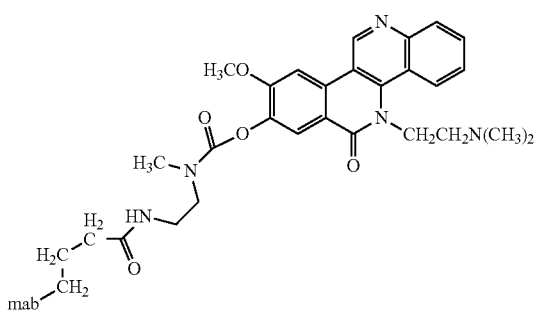
X = is a leaving group such as chloro or p-nitrophenoxy 87 88
Scheme 12
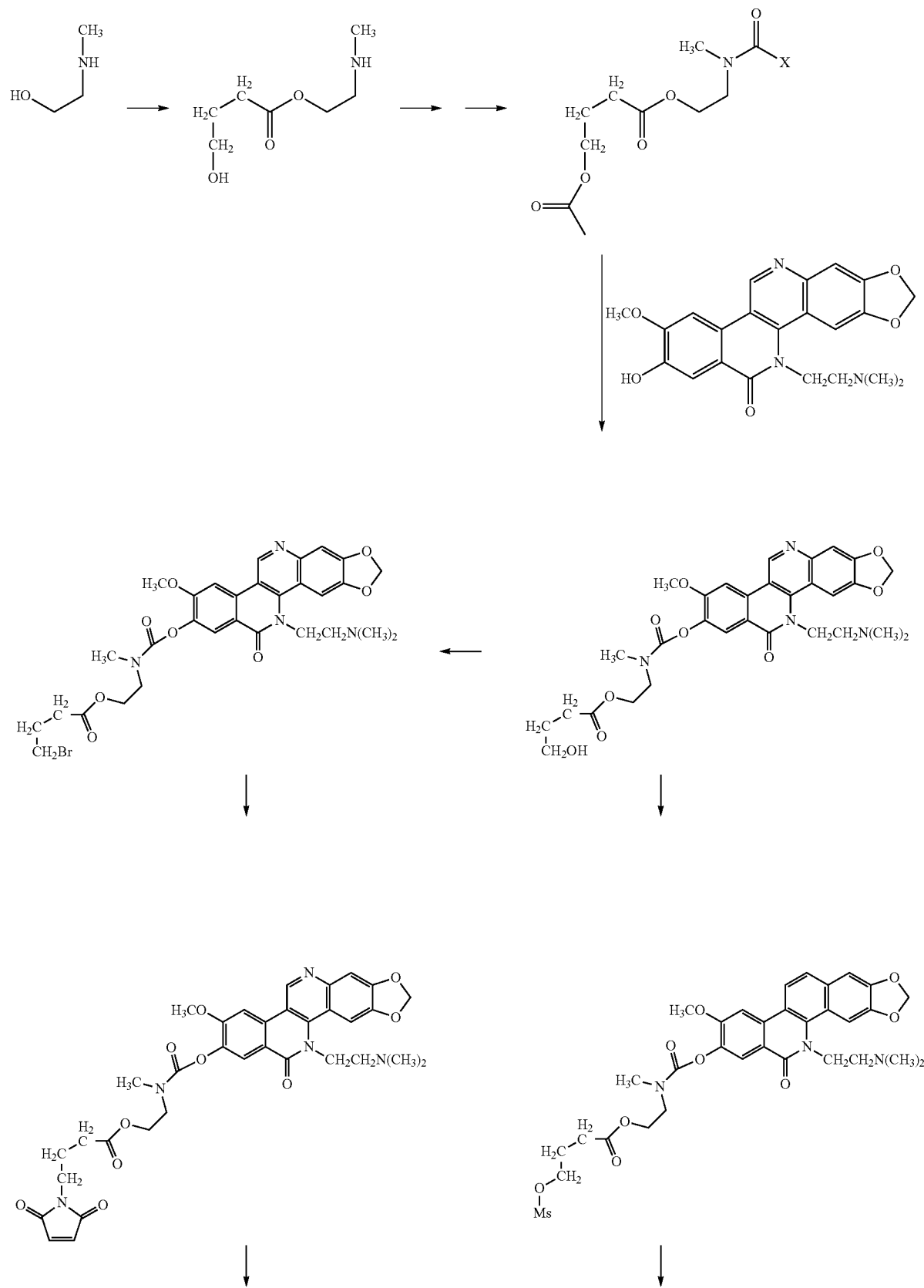

89

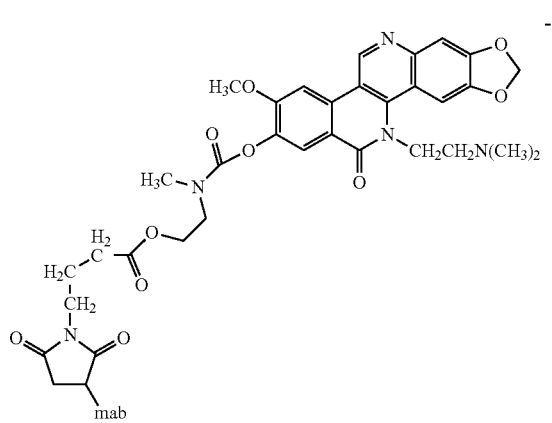

X = is a leaving group such as chloro or p-nitrophenoxy

The maleimide moiety is known to react with the thiol functional group, including the thiol functional groups present in many proteins, to form a succinimidyl-sulfur covalent bond. Schemes 7, 8, 11 and 12 depict intermediates incorporating the maleimide group. Accordingly, in one embodiment of the invention, a succinimidyl group attached to a compound of formula I (e.g. as depicted in Schemes 7, 8, 11 and 12), is linked to a mab through a sulfur atom of the mab The invention provides for novel intermediates which are useful for the preparation of ADCs (as depicted in Scheme 3-12), as well as the corresponding intermediates wherein compound A1 is replaced with a compound of formula A or formula B.

Accordingly, in one embodiment the invention provides a synthetic intermediate that is useful for preparing an ADC of the invention, which synthetic intermediate is:

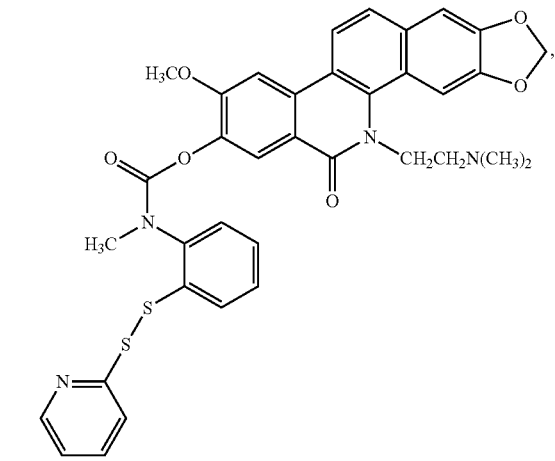

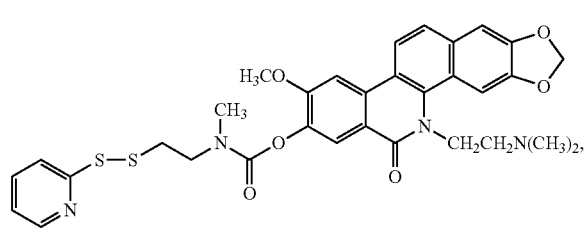

90

-continued

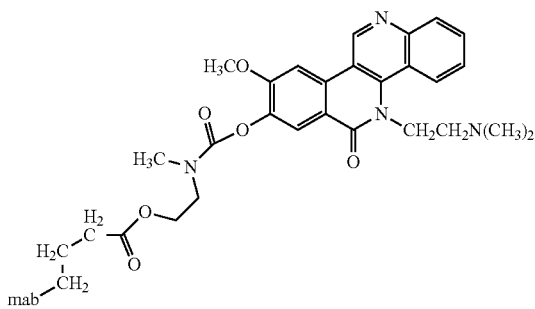

-continued

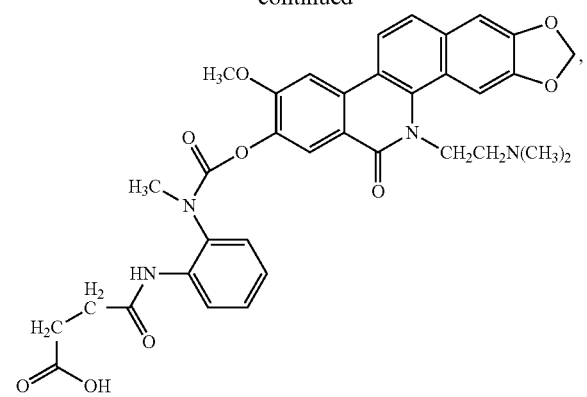

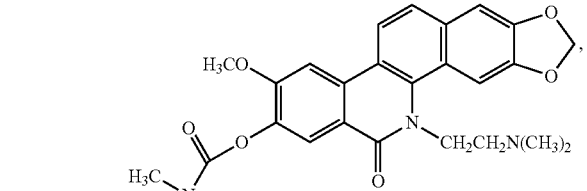

91
-continued
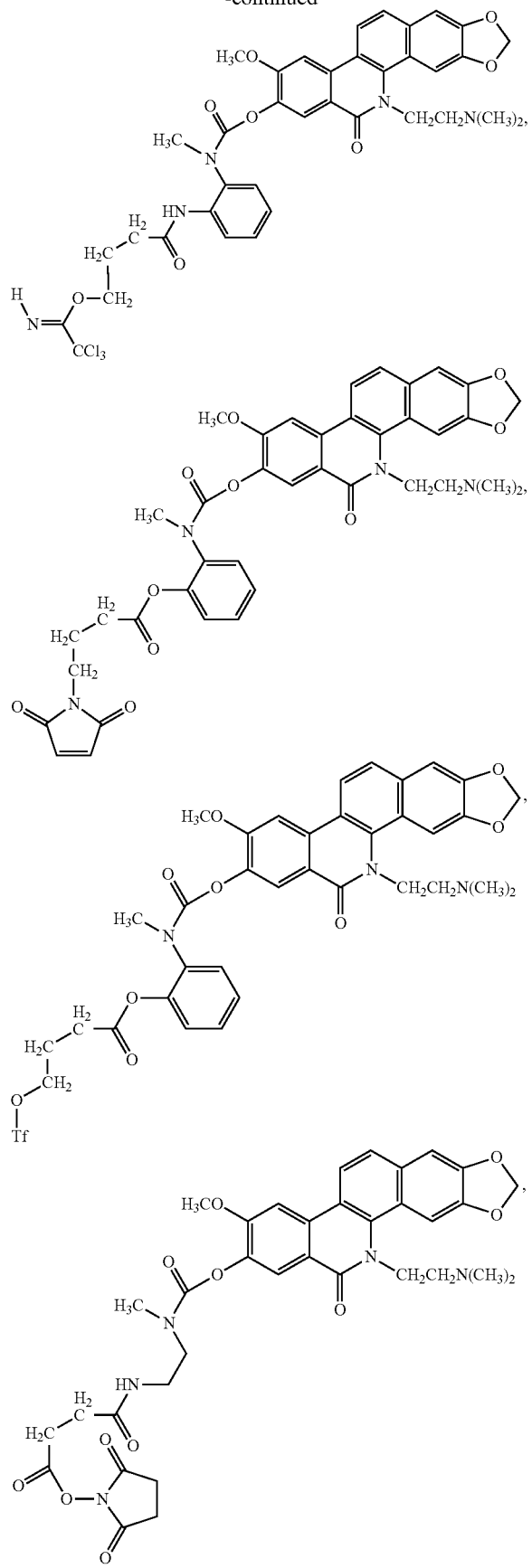
92
-continued
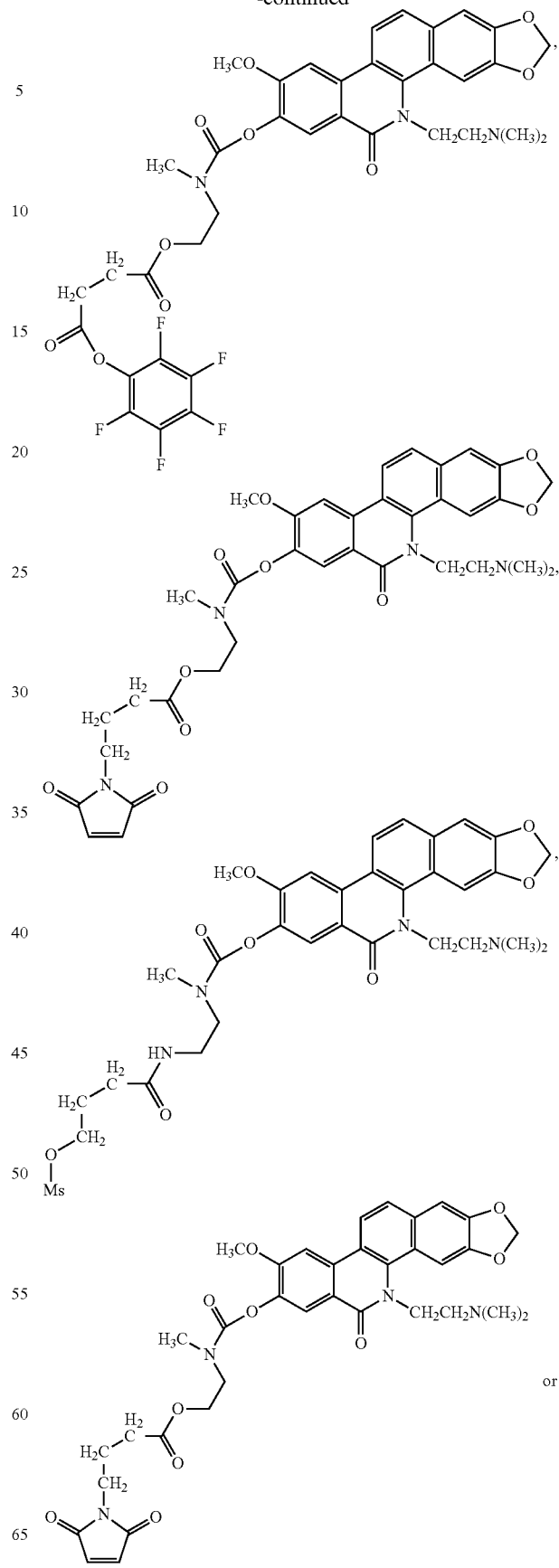
or

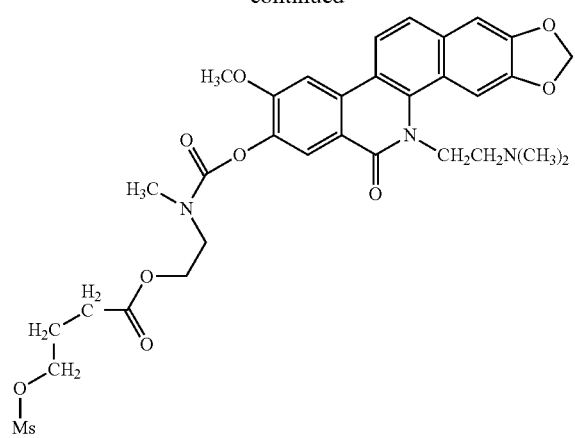
In another embodiment the invention provides a synthetic intermediate that is useful for preparing an ADC of the invention, which synthetic intermediate is:
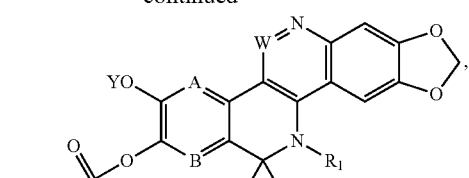
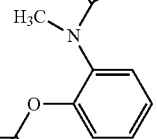
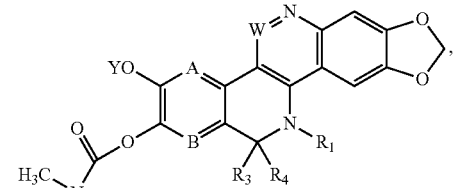
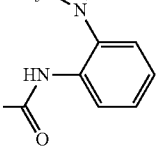
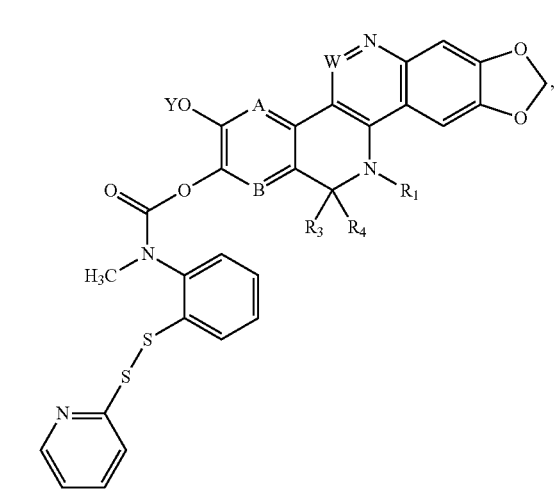
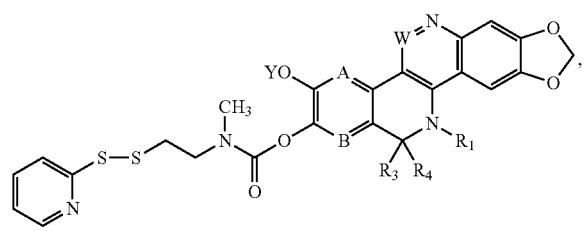
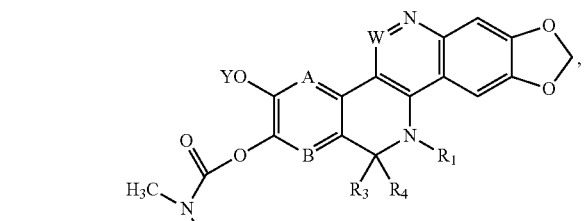
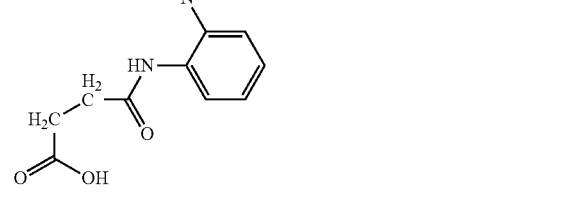

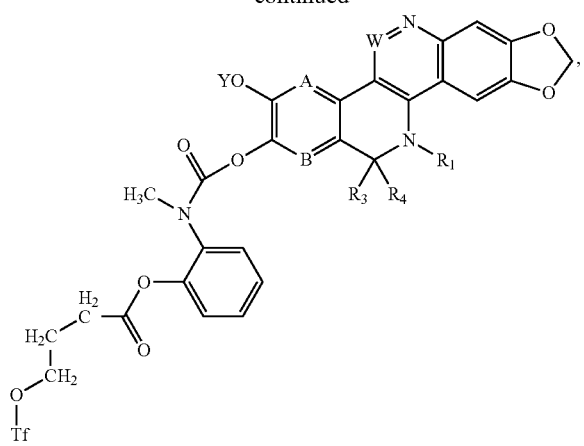
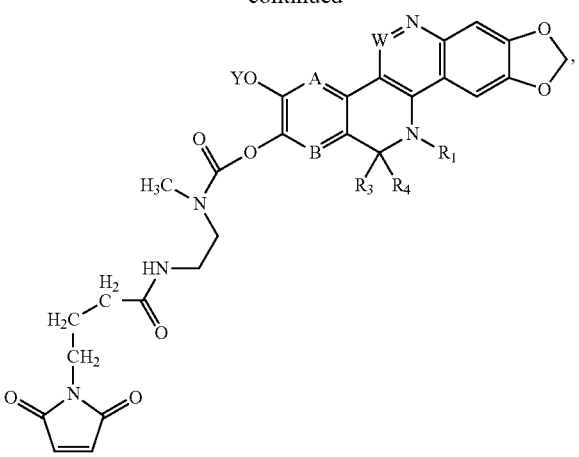

-continued

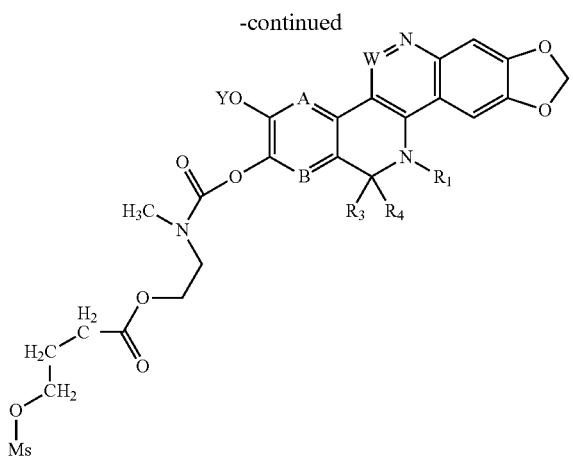

wherein the values for A, B, W, Y, $R_1$, $R_3$ and $R_4$ are as provided hereinabove.

Pharmaceutically acceptable salts may be obtained using standard procedures well known in the art, for example by reacting a sufficiently basic compound such as an amine with a suitable acid affording a physiologically acceptable anion. Alkali metal, for example, sodium, potassium or lithium, or alkaline earth metal, for example calcium, salts of carboxylic acids can also be made.

The compounds of the invention can be formulated as pharmaceutical compositions and administered to a mammalian host, such as a human patient in a variety of forms adapted to the chosen route of administration, that is, orally or parenterally, by intravenous, intramuscular, topical or subcutaneous routes. Typically the compounds will be administered by infusion.

Thus, the present compounds may be systemically administered, for example, orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compound may also be administered intravenously or intraperitoneally by infusion or injection. Solutions of the compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to effect topoisomerase I mediated DNA cleavage can be determined using pharmacological models that are well known to the art, for example, using a model like Test A described below.

Test A. Topoisomerase I-Mediated DNA Cleavage Assay

Human topoisomerase I was expressed in *E. Coli* and isolated as a recombinant fusion protein using a T7 expression system as described previously, see Makhey, D. et al., *Bioorg. Med. Chem.*, 2000, 8, 1-11. DNA topoisomerase I was purified from calf thymus gland as reported previously, see Maniatis, T., et al., J. Molecular Cloning, a Laboratory Manual, Cold Spring Harbor Laboratory, Cold Spring Harbor, N.Y., 149-185). Plasmid YepG was also purified by the alkali lysis method followed by phenol deproteination and CsCl/ethidium isopycnic centrifugation method as described, see Maniatis, T.; Fritsch, E. F.; Sambrook, J. *Molecular Cloning, a Laboratory Manual*; Cold Spring Harbor Laboratory: Cold Spring Harbor, N.Y. 1982; pp 149-185. The end-labeling of the plasmid was accomplished by digestion with a restriction enzyme followed by end-filling with Klenow polymerase as previously described, see Liu, L. F.; Rowe, T. C.; Yang, L.; Tewey, K. M.; Chen, G. L., *J. Biol. Chem.* 1983, 258, 15365. Cleavage assays were performed as previously reported, see B. Gatto et al. *Cancer Res.*, 1996, 56, 2795-2800. The drug and the DNA in presence of topoisomerase I was incubated for 30 minutes at 37° C. After development of the gels, typically 24-hour exposure was used to obtain autoradiograms outlining the extent of DNA fragmentation.

The cytotoxic effects of a compound of the invention can be determined using pharmacological models that are well known in the art, for example, using a model like Test B described below.

Test B. Cytotoxic assays (cancer cell lines and efflux transporter cell lines)

The cytotoxicity was determined using the MTT-microtiter plate tetrazolinium cytotoxicity assay (MTA). The human lymphoblast RPMI 8402 and its camptothecin-resistant variant cell line, CPT-K5 was provided by Dr. Toshiwo Andoh (Aichi Cancer Center Research Institute, Nagoya, Japan). The P388 mouse leukemia cell line and its CPT-resistant TOP1-deficient variant P388/CPT45 were obtained from Michael R. Mattern and Randal K. Johnson (GlaxoSmith-Kline, King of Prussia, Pa.). The KB3-1 cell line and its multidrug-resistant variant KBV-1 were obtained from K.V. Chin (The Cancer Institute of New Jersey, New Brunswick, N.J.). The KBH5.0 cell line as noted previously was derived from KB3-1 by stepwise selection against Hoechst 33342. The cytotoxicity assay was performed using 96-well microtiter plates. Cells were grown in suspension at 37° C. in 5% $CO_2$ and maintained by regular passage in RPMI medium supplemented with 10% heat inactivated fetal bovine serum, L-glutamine (2 mM), penicillin (100 U/mL), and Streptomycin (0.1 mg/mL). For determination of $IC_{50}$, cells were exposed continuously for four days to varying concentrations of drug, and MTT assays were performed at the end of the fourth day. Each assay was performed with a control that did not contain any drug. All assays were performed at least twice in six replicate wells.

Experimental results from Test B for representative compounds of the invention are shown in the Table 1 below. These results demonstrate that compounds of the invention can function as cytotoxic agents against tumor cell lines. Accordingly compounds of the invention of may be useful as therapeutic agents for the treatment of cancer (e.g. leukemia, non-small lung cancer, colon cancer, CNS cancer, melanoma, ovarian cancer, renal cancer, prostate cancer or breast cancer).

TABLE 1

Cytotoxicity Data (Single Assay)

| Compound | Cytotoxicity ($IC_{50}$ values (μM)) | | | |
| --- | --- | --- | --- | --- |
|  | RPMI8402 | CPT-K5 | P388 | P388/CPT45 |
| Compound of Example 1 | 0.006 | 0.50 | 0.002 | 0.12 |
|  | 0.009 | 0.55 | 0.002 |  |
| Compound of Example 2 | 0.05 | 2.0 | 0.03 | 0.4 |
|  | 0.07 | 2.0 | 0.03 |  |
| Compound of Example 3 | 0.009 | 0.70 | 0.004 | 0.30 |
| Compound of Example 4 | 0.0007 | 0.30 | 0.003 | 0.25 |
| Compound of Example 5 | 0.003 | 0.33 | 0.002 | 0.07 |
| Compound of Example 6 | 0.0006 | 0.25 | 0.0002 | 0.06 |
| Compound of Example 7 | 0.0005 | 0.31 | 0.001 | 0.08 |
| Compound of Example 8 | 0.003 | 0.50 | 0.003 | 0.09 |
| Compound of Example 9 | 1.7 | >10 | 1.3 | 3.8 |
| Compound of Example 10 | 0.55 | 1.5 | 0.50 | 0.50 |

The ability of a compound of the invention to be actively transported can be determined using pharmacological models that are well known in the art, for example, using a model like the test described below.

The cytotoxicity of the representative compounds of the invention were also tested against cell line KB3-1 (parent cell line), KBV-1 (a variant that overexpresses efflux transporter MDR1) and KBH5.0 (a variant that overexpresses BCRP). The data is tabulated in Table 3. Differences in the relative cytotoxicity between the parent and variant cell lines may be indicative of a compound that is a substrate for an efflux transporter. These data suggest that the compounds tested may be substrates to varying degrees for MDR1 and BCRP and that the compound of Example 2 is not a substrate for BCRP. Accordingly, compounds of the invention may be useful to treat tumors that are resistant to other anticancer agents, including anticancer agents that are susceptible to efflux by BCRP (e.g. anthracyclines, mitoxantrone, topotecan, irinotecan, bisanthrone, doxorubicin, daunorubicin, and epirubin.

TABLE 2

| Compound | Cytotoxicity ($IC_{50}$ values (µM)) | | |
|---|---|---|---|
| | KB3-1 | KBV-1 | KBH5.0 |
| Compound of Example 1 | 0.002 | 0.06 | 0.025 |
| Compound of Example 2 | 0.04 | 0.2 | 0.04 |
| Compound of Example 3 | 0.007 | 0.06 | 0.025 |
| Compound of Example 4 | 0.002 | 0.024 | 0.017 |
| Compound of Example 5 | 0.003 | 0.058 | 0.013 |
| Compound of Example 6 | 0.001 | 0.003 | 0.008 |
| Compound of Example 7 | 0.002 | 0.004 | 0.009 |
| Compound of Example 8 | 0.004 | 0.04 | 0.015 |
| Compound of Example 9 | 0.40 | 3.0 | 2.0 |
| Compound of Example 10 | 0.75 | 1.6 | 1.1 |

The in vivo antitumor activity of a compound of the invention can be determined using pharmacological models that are well known in the art, for example, using a model like Test C described below.

Test C. Human Tumor Xenograft Assay

Bioassays are performed using female NCR/NU NU mice of approximately 9 weeks of age as obtained from Taconic Farms, Inc. (Germantown, N.Y., USA). Mice are housed 4 per cage in laminar flow HEPA filtered microisolator caging (Allentown Caging Equipment Co., Allentown, N.J., USA). Mice are fed Purina autoclavable breeder chow #5021 and given drinking water, purified by reverse-osmosis, ad libitum. Five days after arrival within the animal facility, the mice are inoculated on the right flank with $1.5 \times 10^6$ MDA-MB-435 tumor cells in 0.1 mL of RPMI 1640 Media by sc injection (25 gauge needle×⅝"). The MDA-MB-435 cells are grown in 75 cm² flasks using RPMI 1640 Media and 10% fetal bovine serum. Tumors are of sufficient size at 19-20 days after inoculation. Tumor-bearing mice are evenly matched in each experimental group based on tumor volume. Tumor volume is calculated by measuring the tumor with a microcaliper. The length (l) is the maximum two dimensional distance of the tumor and the width (w) is the maximum distance perpendicular to this length measured in mm. Tumor volume is calculated using the formula $(l \cdot w^2)/2$. Every mouse is weighed individually on a daily basis. Dose adjustments for each experimental group can be made throughout the study based upon the effect or lack of an effect of treatment on average body weights. Tumor volume is determined for each individual mouse every other day.

Topoisomerase inhibitors are also known to possess antifungal, antipsoritic (psoriasis), antiprotozoal, antihelmetic, and antiviral activity. Accordingly, the topoisomerase inhibitors of the invention may also be useful as, antifungal, antipsoritic (psoriasis), antiprotozoal, antihelmetic, or antiviral agents. In particular, compounds of the invention that demonstrate little or no activity as mammalian topoisomerase I poisons, because of the possibility of similar molecular mechanism of action, could be highly active and selective antifungal, antipsoritic (psoriasis), antiprotozoal, antihelmetic, or antiviral agents. Thus, certain compounds of the invention may be particularly useful as systemic antifungal, antipsoritic (psoriasis), antiprotozoal, antihelmetic, or antiviral agents in mammals. The invention also provides the use of a compound of the invention for the manufacture of a medicament useful for producing an antifungal, antipsoritic (psoriasis), antiprotozoal, antihelmetic, or antiviral effect in a mammal.

As used herein, the term "solid mammalian tumors" include cancers of the head and neck, lung, mesothelioma, mediastinum, esophagus, stomach, pancreas, hepatobiliary system, small intestine, colon, rectum, anus, kidney, ureter, bladder, prostate, urethra, penis, testis, gynecological organs, ovarian, breast, endocrine system, skin central nervous system; sarcomas of the soft tissue and bone; and melanoma of cutaneous and intraocular origin. The term "hematological malignancies" includes childhood leukemia and lymphomas, Hodgkin's disease, lymphomas of lymphocytic and cutaneous origin, acute and chronic leukemia, plasma cell neoplasm and cancers associated with AIDS. The preferred mammalian species for treatment are humans and domesticated animals.

The invention will now be illustrated by the following non-limiting Examples.

Certain compounds of the present invention were prepared in accordance with the Scheme A using, for example, the reactions and reagents illustrated.

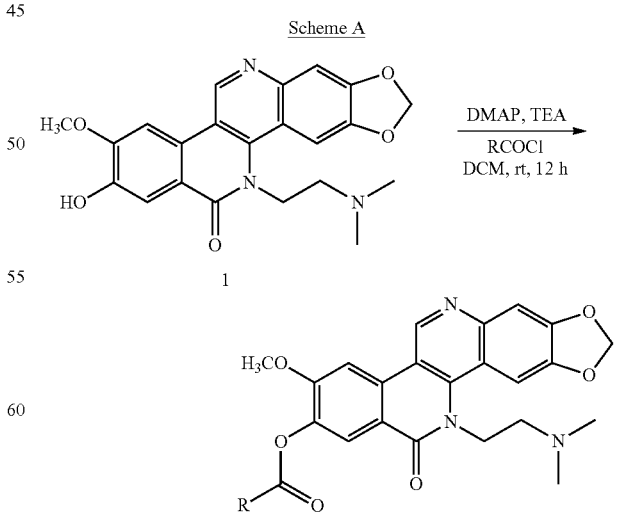

Scheme A

To a solution of starting material (0.102 mmol) in dichloromethane (10 ML) was added DMAP (0.205 mmol) and triethylamine (0.5 mL), and the mixture was stirred at room temperature for 30 minutes. To this reaction mixture was added appropriate acid chloride (0.102 mmol) and the solution was left to stir at room temperature overnight. The reaction mixture was diluted with dichloromethane and washed with saturated sodium bicarbonate, brine, dried over $Na_2SO_4$, filtered and concentrated under vacuum to get a brown solid. Column chromatography using chloroform: methanol mixture gave the pure product. (Yield ranging from 80%-85%).

EXAMPLE 1

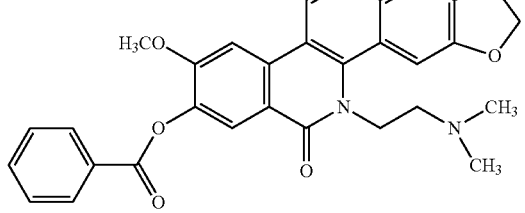

The compound of Example 1 (5-(2-(dimethylamino) ethyl)-9-methoxy-2,3-methylenedioxy-6-oxo-5,6-dihydrodibenzo[c,h][1,6]naphthyridin-8-yl benzoate) was prepared following the method of Scheme A outlined above. $^1$H NMR (CDCl$_3$) δ 2.26 (s, 6H), 2.90 (m, 2H), 4.03 (s, 3H), 4.60 (m, 2H), 6.16 (s, 2H), 7.44 (s, 1H), 7.50-7.67 (m, 3H), 7.76 (s, 1H), 7.85 (s, 1H), 8.25 (m, 3H), 9.36 (s, 1H); $^{13}$C NMR (CDCl$_3$) δ 45.8, 49.2, 56.4, 57.8, 101.4, 102.3, 103.1, 107.1, 111.4, 114.8, 119.3, 123.0, 128.8, 129.1, 130.5, 132.7, 133.9, 141.2, 142.1, 143.7, 147.8, 147.9, 150.3, 156.2, 163.7, 164.6.

EXAMPLE 2

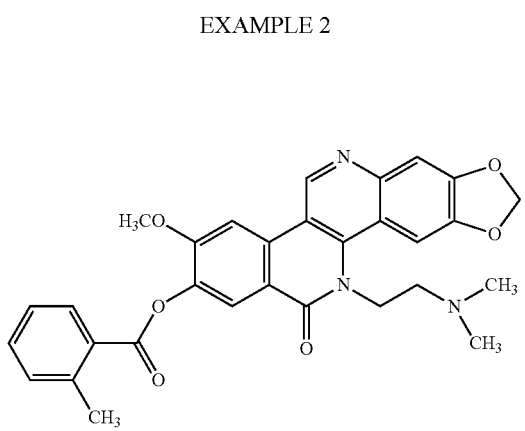

The compound of Example 2 (5-(2-(dimethylamino) ethyl)-9-methoxy-2,3-methylenedioxy-6-oxo-5,6-dihydrodibenzo[c,h][1,6]naphthyridin-8-yl 2-methylbenzoate) was prepared following the method of Scheme A outlined above. $^1$H NMR (CDCl$_3$) δ 2.26 (s, 6H), 2.69 (s, 3H), 2.91 (t, J=7.0 Hz, 2H), 4.06 (s, 3H), 4.62 (t, J=7.0 Hz, 2H), 6.17 (s, 2H), 7.31 (m, 2H), 7.51-7.46 (m, 2H), 7.78 (s, 1H), 7.87 (s, 1H), 8.22 (m, 1H), 8.25 (s, 1H), 9.39 (s, 1H); $^{13}$C NMR (CDCl$_3$) δ 20.9, 44.9, 48.2, 55.4, 56.8, 100.4, 101.3, 102.1, 106.1, 110.5, 113.9, 118.3, 122.1, 125.1, 127.4, 130.5, 131.0, 131.6, 131.9, 140.2, 140.4, 141.2, 142.7, 146.8, 146.9, 149.3, 155.2, 162.8, 164.3.

EXAMPLE 3

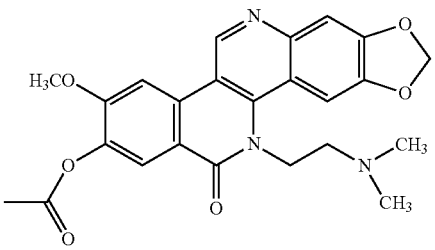 [SMILES: COc1cc2c(cc1OC(C)=O)c(=O)n(CCN(C)C)c1c3cc4c(cc3ncc21)OCO4]

The compound of Example 3 (5-(2-(dimethylamino) ethyl)-9-methoxy-2,3-methylenedioxy-6-oxo-5,6-dihydrodibenzo[c,h][1,6]naphthyridin-8-yl acetate) was prepared following the method of Scheme A outlined above. $^1$H NMR (CDCl$_3$) δ 2.30 (s, 6H), 2.38 (s, 3H), 2.94 (m, 2H), 4.06 (s, 3H), 4.64 (m, 2H), 6.17 (s, 2H), 7.46 (s, 1H), 7.74 (s, 1H), 7.84 (s, 1H), 8.13 (s, 1H), 9.37 (s, 1H); $^{13}$C NMR (CDCl$_3$) δ 28.8, 44.7, 48.2, 55.4, 56.8, 100.3, 101.4, 102.0, 106.1, 118.2, 121.9, 131.7, 142.6, 146.9, 149.4, 154.9, 163.1, 168.0; HRMS (ESI, M+H) calcd for $C_{24}H_{23}N_3O_6$ 449.1587. found 450.1661 [M+H].

EXAMPLE 4

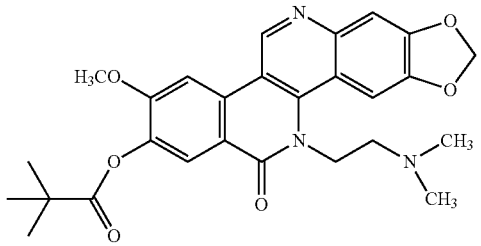 [SMILES: COc1cc2c(cc1OC(=O)C(C)(C)C)c(=O)n(CCN(C)C)c1c3cc4c(cc3ncc21)OCO4]

The compound of Example 4 (5-(2-(dimethylamino) ethyl)-9-methoxy-2,3-methylenedioxy-6-oxo-5,6-dihydrodibenzo[c,h][1,6]naphthyridin-8-yl pivalate) was prepared following the method of Scheme A outlined above. $^1$H NMR (CDCl$_3$) δ 1.39 (s, 9H), 2.29 (s, 6H), 2.90 (m, 2H), 4.03 (s, 3H), 4.62 (m, 2H), 6.15 (s, 2H), 7.45 (s, 1H), 7.69 (s, 1H), 7.73 (s, 1H), 8.08 (s, 1H), 9.34 (s, 1H) $^{13}$C NMR (CDCl$_3$) δ 27.3, 27.4, 39.3, 45.5, 48.7, 56.4, 57.4, 101.2, 102.4, 103.0, 106.8, 111.6, 114.9, 119.2, 122.8, 132.4, 141.5, 142.1, 143.5, 147.5, 147.8, 150.4, 156.2, 163.8, 176.5; HRMS (ESI, M+H) calcd for $C_{27}H_{29}N_3O_6$ 491.2056. found 492.2132 [M+H].

EXAMPLE 5

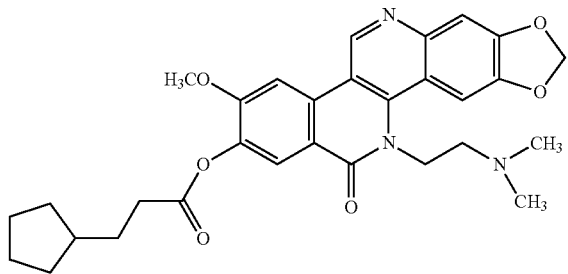 [SMILES: COc1cc2c(cc1OC(=O)CCC1CCCC1)c(=O)n(CCN(C)C)c1c3cc4c(cc3ncc21)OCO4]

The compound of Example 5 (5-(2-(dimethylamino)ethyl)-9-methoxy-2,3-methylenedioxy-6-oxo-5,6-dihydrodibenzo[c,h][1,6]naphthyridin-8-yl (3-cyclopentyl)propionate) was prepared following the method of Scheme A outlined above. $^1$H NMR (CDCl$_3$) δ 1.57-1.86 (m, 11H), 2.27 (s, 6H), 2.65 (t, J=7.6 Hz, 2H), 2.90 (t, J=7.6 Hz, 2H), 4.04 (s, 3H), 4.60 (m, 2H), 6.16 (s, 2H), 7.45 (s, 1H), 7.72 (s, 1H), 7.85 (s, 1H), 8.11 (s, 1H), 9.36 (s, 1H); $^{13}$C NMR (CDCl$_3$) δ 24.3, 30.3, 31.6, 32.4, 38.8, 44.8, 48.1, 55.4, 56.8, 100.4, 101.3, 102.0, 106.1, 110.4, 113.8, 118.2, 121.9, 131.5, 140.1, 141.1, 142.6, 146.9, 149.3, 155.0, 162.7, 170.8; HRMS (ESI, M+H) calcd for $C_{30}H_{33}N_3O_6$ 531.2369. found 532.2444 [M+H].

EXAMPLE 6

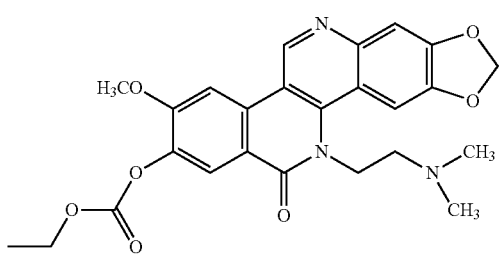 [SMILES: CCOC(=O)Oc1cc2c(=O)n(CCN(C)C)c3c4cc5c(cc4ncc3c2cc1OC)OCO5]

The compound of Example 6 (5-(2-(dimethylamino)ethyl)-9-methoxy-2,3-methylenedioxy-6-oxo-5,6-dihydrodibenzo[c,h][1,6]naphthyridin-8-yl ethyl carbonate) was prepared by adding ethyl chloroformate drop-wise to a suspension of compound 1 (Scheme A) in dichloromethane and pyridine which was cooled in ice bath. After the temperature was allowed to increase to room temperature, the reaction mixture was stirred overnight. The reaction mixture was diluted with dichloromethane and was washed with water, 1N HCl and brine. The organic layer was dried, concentrated and purification of the crude product by silica gel chromatography gave the pure product in 78% yield. $^1$H NMR (CDCl$_3$) δ 1.41 (t, 3H), 2.61 (s, 6H), 2.89 (m, 2H), 4.07 (s, 3H), 4.35 (qt, 2H), 4.57 (m, 2H), 6.16 (s, 2H), 7.43 (s, 1H), 7.72 (s, 1H), 7.84 (s, 1H), 8.21 (s, 1H), 9.33 (s, 1H). $^{13}$C NMR (CDCl$_3$) δ 13.3, 44.8, 48.2, 55.5, 56.8, 64.4, 100.9, 101.3, 102.2, 106.1, 110.3, 113.8, 118.2, 121.5, 131.7, 140.1, 141.2, 142.6, 146.8, 147.0, 149.4, 151.9, 154.9, 162.6.

EXAMPLE 7

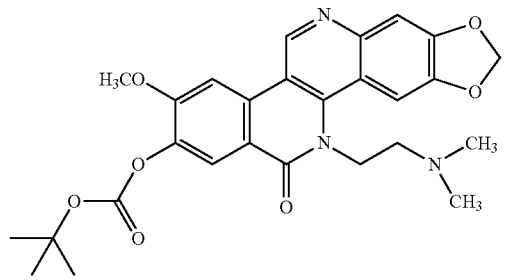 [SMILES: COc1cc2c(cc1OC(=O)OC(C)(C)C)c(=O)n(CCN(C)C)c1c3cc4c(cc3ncc21)OCO4]

The compound of Example 7 (tert-butyl 5-(2-(dimethylamino)ethyl)-9-methoxy-2,3-methylenedioxy-6-oxo-5,6-dihydrodibenzo[c,h][1,6]naphthyridin-8-yl carbonate) was prepared by mixing compound 1 (Scheme A) (1.0 mmol), dimethylaminopyridine (0.1 mmol), di-tert butyl dicarbonate (1.0 mmol) in dichloromethane. This mixture was stirred at room temperature overnight. Evaporation of the solvent and purification of the crude product by silica gel chromatography furnished the pure product in 84% yield. $^1$H NMR (CDCl$_3$) δ 1.57 (s, 9H), 2.61 (s, 6H), 2.90 (m, 2H), 4.08 (s, 3H), 4.59 (m, 2H), 6.16 (s, 2H), 7.45 (s, 1H), 7.73 (s, 1H), 7.86 (s, 1H), 8.21 (s, 1H), 9.35 (s, 1H). $^{13}$C NMR (CDCl$_3$) δ 27.7, 45.8, 49.1, 56.4, 57.8, 84.2, 101.4, 102.4, 103.1, 107.1, 111.4, 114.8, 119.1, 122.5, 132.5, 141.2, 142.1, 143.6, 147.9, 150.3, 156.0, 163.7.

EXAMPLE 8

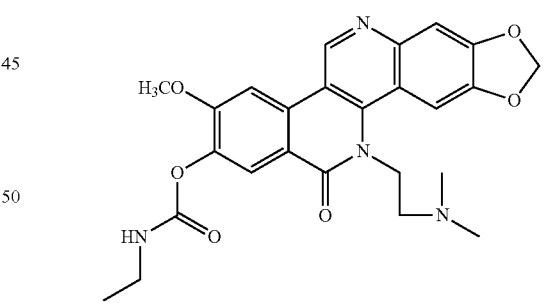

The compound of Example 8 (5-(2-(dimethylamino)ethyl)-9-methoxy-2,3-methylenedioxy-6-oxo-5,6-dihydrodibenzo[c,h][1,6]naphthyridin-8-yl ethylcarbamate) was prepared by treating a solution of compound 1 (Scheme 2) and triethylamine (2 equiv.) in dichloromethane with ethyl isocyanate at room temperature. The reaction mixture was stirred at room temperature overnight, quenched with water and extracted with ethyl acetate. The extracts were washed with brine and dried over sodium sulfate. Purification of the crude product by silica gel chromatography afforded the pure product in 76% yield. $^1$H NMR (CDCl$_3$) δ 1.2 (t, 3H), 2.61 (s, 6H), 2.89 (m, 2H), 4.06 (s, 3H), 4.41 (m, 2H), 4.59 (m, 2H), 6.15 (s, 2H), 7.44 (s, 1H), 7.71 (s, 1H), 7.84 (s, 1H), 8.16 (s, 1H), 9.34 (s, 1H).

EXAMPLE 9

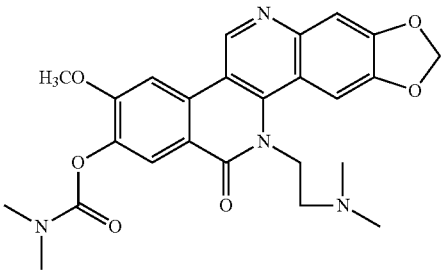 [SMILES: COc1cc2c(cc1OC(=O)N(C)C)c(=O)n(CCN(C)C)c1c3cc4c(cc3ncc21)OCO4]

The compound of Example 9 (5-(2-(dimethylamino)ethyl)-9-methoxy-2,3-methylenedioxy-6-oxo-5,6-dihydrodibenzo[c,h][1,6]naphthyridin-8-yl dimethylcarbamate) was prepared by adding $Me_2NCOCl$ (1.2 equiv.) to a solution of 1 and $K_2CO_3$ (1.2 equiv.) in DMF (1.2 equiv.) at room temperature. The reaction mixture was stirred at room temperature overnight. After dilution with water, the reaction mixture was extracted with ethyl acetate and the combined organic layer was washed with brine and was dried over $Na_2SO_4$. Purification of the crude product by silica gel chromatography produced the pure product in 85% yield. $^1H$ NMR ($CDCl_3$) δ 2.61 (s, 6H), 2.86 (m, 2H), 3.04 (s, 3H), 3.17 (s, 3H), 4.06 (s, 3H), 4.59 (m, 2H), 6.16 (s, 2H), 7.45 (s, 1H), 7.71 (s, 1H), 7.85 (s, 1H), 8.15 (s, 1H), 9.36 (s, 1H).

EXAMPLE 10

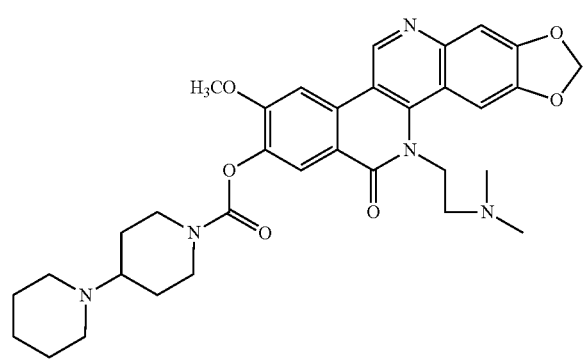 [SMILES: COc1cc2c(cc1OC(=O)N1CCC(N3CCCCC3)CC1)c(=O)n(CCN(C)C)c1c3cc4c(cc3ncc21)OCO4]

The compound of Example 10 (5-(2-(dimethylamino)ethyl)-9-methoxy-2,3-methylenedioxy-6-oxo-5,6-dihydrodibenzo[c,h][1,6]naphthyridin-8-yl 1,4'-bipiperidine-1'-carboxylate) was prepared following the method of Scheme A outlined above. $^1H$ NMR ($CDCl_3$) δ 1.42-1.89 (m, 11H), 2.24 (s, 6H), 2.48 (m, 6H), 2.86 (m, 2H), 4.04 (s, 3H), 4.2-4.5 (m, 2H), 4.58 (m, 2H), 6.15 (s, 2H), 7.44 (s, 1H), 7.70 (s, 1H), 7.83 (s, 1H), 8.14 (s, 1H), 9.34 (s, 1H); $^{13}C$ NMR ($CDCl_3$) δ 24.9, 26.6, 28.0, 44.6, 45.9, 46.2, 49.1, 50.4, 56.5, 57.8, 62.6, 101.4, 102.3, 103.0, 107.1, 111.6, 114.9, 119.3, 123.1, 132.2, 141.8, 142.0, 143.7, 147.8, 147.8, 150.2, 153.1, 156.6, 163.8; HRMS (ESI, M+H) calcd for $C_{33}H_{39}N_5O_6$ 601.29. found 602.2970 [M+H].

EXAMPLE 11

The following illustrate representative pharmaceutical dosage forms, containing a compound of the invention ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Injection 3 (1 mg/ml) | mg/ml |
| --- | --- |
| 'Compound X' (free base form) | 1.0 |
| Citric Acid | 0.1% |
| D5W | q.s. ad 1 mL |

| (vii) Aerosol | mg/can |
| --- | --- |
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

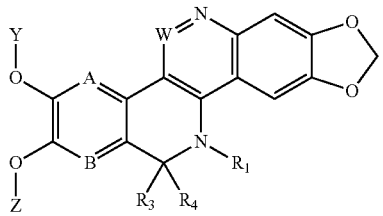

wherein:
A and B are independently N or CH;
W is N or CH;
$R_3$ and $R_4$ are each independently H, $(C_1-C_6)$alkyl, or substituted $(C_1-C_6)$alkyl, or $R_3$ and $R_4$ together are =O, =S, =NH or =N-$R_2$;
at least one of Y and Z is aryl$(C_1-C_6)$alkanoyl, heteroaryl$(C_1-C_6)$alkanoyl, $(C_1-C_6)$alkoxycarbonyl, a self-immolative moiety, cascading prodrug moiety or a linker substituted with one or more targeting moieties and the other is hydrogen, $(C_1-C_6)$alkyl, substituted $(C_1-C_6)$alkyl, $(C_1-C_6)$alkanoyl, substituted$(C_1-C_6)$alkanoyl, -C(=O)N$R_cR_d$, aryl$(C_1-C_6)$alkanoyl or heteroaryl$(C_1-C_6)$alkanoyl wherein any aryl$(C_1-C_6)$alkanoyl or heteroaryl$(C_1-C_6)$alkanoyl may be optionally substituted with one or more groups independently selected from halo, cyano, $(C_1-C_6)$alkyl, carboxy, $NO_2$, hydroxy, $(C_1-C_6)$alkoxy and $NR_eR_f$;
$R_1$ is a —$(C_1-C_6)$alkyl optionally substituted with one or more solubilizing groups;
$R_2$ is $(C_1-C_6)$alkyl, substituted $(C_1-C_6)$alkyl, aryl or heteroaryl;
$R_c$ and $R_d$ are each independently H, $(C_1-C_6)$ alkyl or substituted $(C_1-C_6)$ alkyl; or $R_c$ and $R_d$ together with the nitrogen to which they are attached form a piperazino, pyrrolidino, or piperidino ring, which ring can optionally be substituted with one or more aryl, heteroaryl, or heterocycle; and $R_e$ and $R_f$ are each independently H, $(C_1-C_6)$ alkyl or substituted $(C_1-C_6)$ alkyl; or $R_e$ and $R_f$ together with the nitrogen to which they are attached form a piperazino, pyrrolidino, or piperidino ring, which ring can optionally be substituted with one or more aryl, heteroaryl, or heterocycle;
or a salt thereof; wherein Y is not H when Z is $(C_1-C_6)$ alkyl; and Y is not $(C_1-C_6)$ alkyl when Z is H.

2. The compound of claim 1 wherein Y is a cascading prodrug moiety; or the compound 5-(2-(dimethylamino)ethyl)-9-methoxy-2,3-methylenedioxy-6-oxo-5,6-dihydrodibenzo-[c,h][1,6]naphthyridin-8-yl ethylcarbamate or a salt thereof.

3. The compound of claim 1 wherein Y is a self-immolative moiety; or the compound 5-(2-(dimethylamino)ethyl)-9-methoxy-2,3-methylenedioxy-6-oxo-5,6-dihydrodibenzo[c,h][1,6]naphthyridin-8-yl ethylcarbamate or a salt thereof.

4. The compound of claim 1 wherein Z is a cascading prodrug moiety; or the compound 5-(2-(dimethylamino)ethyl)-9-methoxy-2,3-methylenedioxy-6-oxo-5,6-dihydrodibenzo-[c,h][1,6]naphthyridin-8-yl ethylcarbamate or a salt thereof.

5. The compound of claim 1 wherein Z is a self-immolative moiety;
or the compound 5-(2-(dimethylamino)ethyl)-9-methoxy-2,3-methylenedioxy-6-oxo-5,6-dihydrodibenzo[c,h][1,6]naphthyridin-8-yl ethylcarbamate or a salt thereof.

6. The compound of claim 1 which is a compound of the formula X:

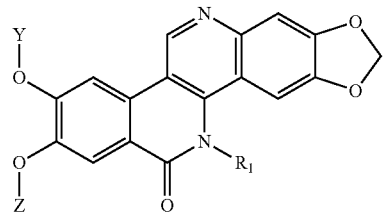

or a pharmaceutically acceptable salt thereof.

7. The compound of claim 6 wherein $R_1$ is a $(C_1-C_6)$alkyl substituted with one $NR_aR_b$ group, wherein $R_a$ and $R_b$ may be the same or different and are chosen from hydrogen, alkyl, arylalkyl, heteroarylalkyl, heterocycloalkyl, cycloalkyl, substituted cycloalkyl, aryl, heteroaryl and heterocyclic.

8. The compound 5-(2-(dimethylamino)ethyl)-9-methoxy-2,3-methylenedioxy-6-oxo-5,6-dihydrodibenzo[c,h][1,6] naphthyridin-8-yl benzoate, 5-(2-(dimethylamino)ethyl)-9-methoxy-2,3-methylenedioxy-6-oxo-5,6-dihydrodibenzo[c,h][1,6]naphthyridin-8-yl 2-methylbenzoate, 5-(2-(dimethylamino)ethyl)-9-methoxy-2,3-methylenedioxy-6-oxo-5,6-dihydrodibenzo[c,h][1,6]naphthyridin-8-yl acetate, 5-(2-(dimethylamino)ethyl)-9-methoxy-2,3-methylenedioxy-6-oxo-5,6-dihydrodibenzo[c,h][1,6]naphthyridin-8-yl pivalate, 5 -(2-(dimethylamino)ethyl)-9-methoxy-2,3-methylenedioxy-6-oxo-5,6-dihydrodibenzo[c,h][1,6]naphthyridin-8-yl (3-cyclopentyl)propionate, 5-(2-(dimethylamino)ethyl)-9-methoxy-2,3-methylenedioxy-6-oxo-5,6-dihydrodibenzo[c,h][1,6]naphthyridin-8-yl ethyl carbonate, tert-butyl 5-(2-(dimethylamino)ethyl)-9-methoxy-2,3-methylenedioxy-6-oxo-5,6-dihydrodibenzo[c,h][1,6]naphthyridin-8-yl carbonate, 5 -(2-(dimethylamino)ethyl)-9-methoxy-2,3 -methylenedioxy-6-oxo-5,6-dihydrodibenzo[c,h][1,6]naphthyridin-8-yl ethylcarbamate, 5 -(2-(dimethylamino)

ethyl)-9-methoxy-2,3 -methylenedioxy-6-oxo-5,6-dihydrodibenzo[c,h][1,6]naphthyridin-8-yl dimethylcarbamate; or 5 -(2-(dimethylamino)ethyl)-9-methoxy-2,3 -methylenedioxy-6-oxo- 5 ,6-dihydrodibenzo [c,h][1,6]naphthyridin- 8 -yl 1 ,4'-bipiperidine- 1 '-carboxylate ; or a salt thereof.

9. The compound of claim 1 wherein Y is:

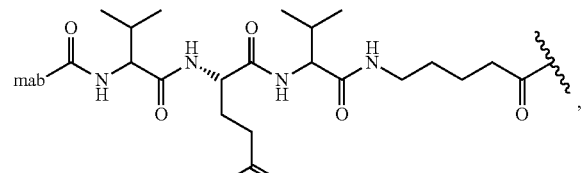

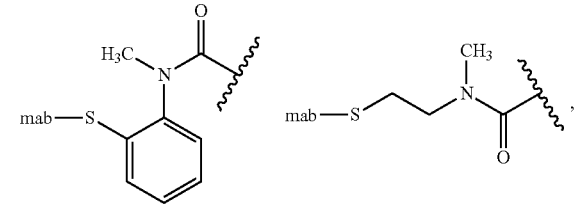

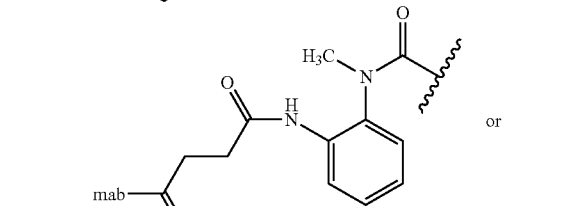

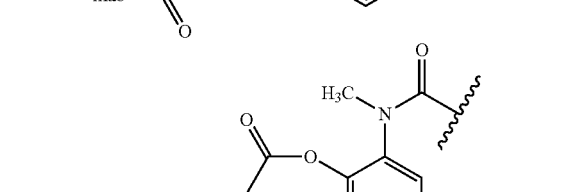

wherein mab is a monoclonal antibody; or the compound 5-(2-(dimethylamino)ethyl)-9-methoxy-2,3-methylenedioxy-6-oxo-5,6-dihydrodibenzo[c,h][1,6]naphthyridin-8-yl ethylcarbamate or a salt thereof.

10. The compound of claim 1 wherein Y is:

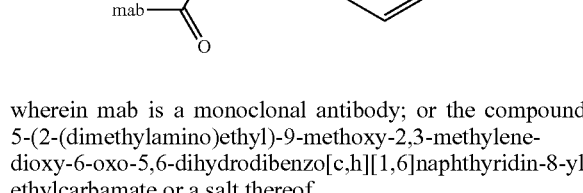

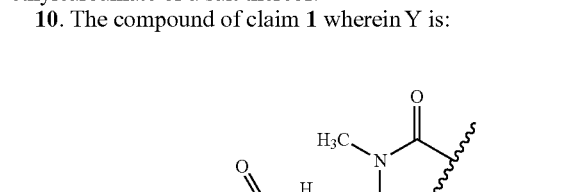

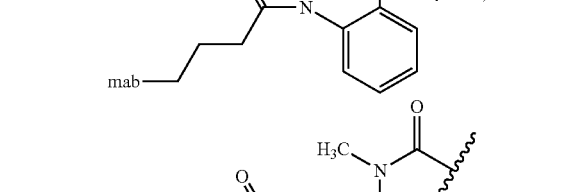

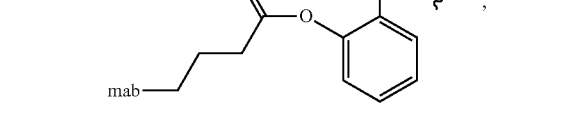

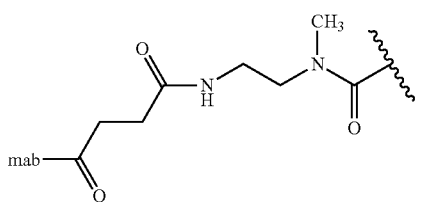

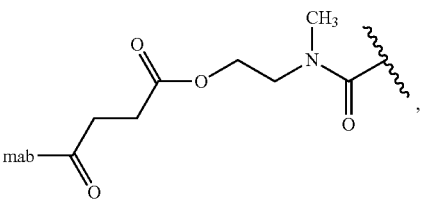

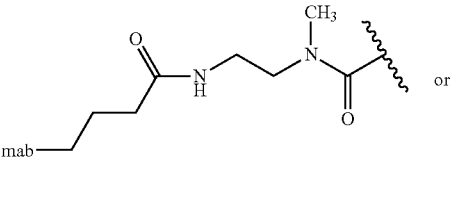

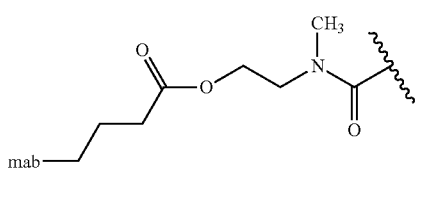

wherein mab is a monoclonal antibody; or the compound 5-(2-(dimethylamino)ethyl)-9-methoxy-2,3-methylenedioxy-6-oxo-5,6-dihydrodibenzo-[c,h][1,6]naphthyridin-8-yl ethylcarbamate or a salt thereof.

11. The compound of claim 1 wherein Y is:

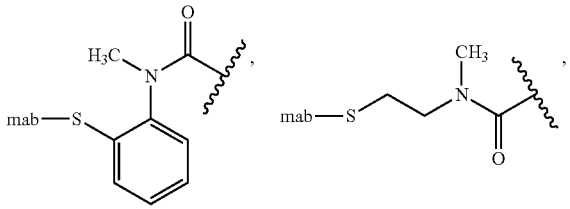

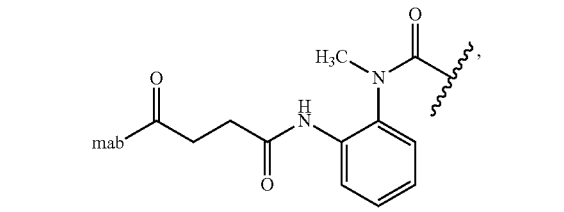

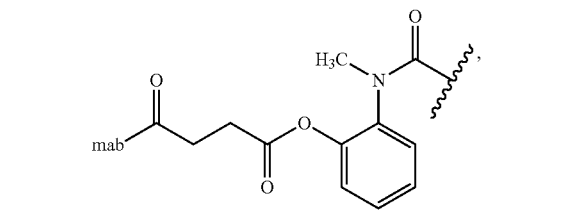

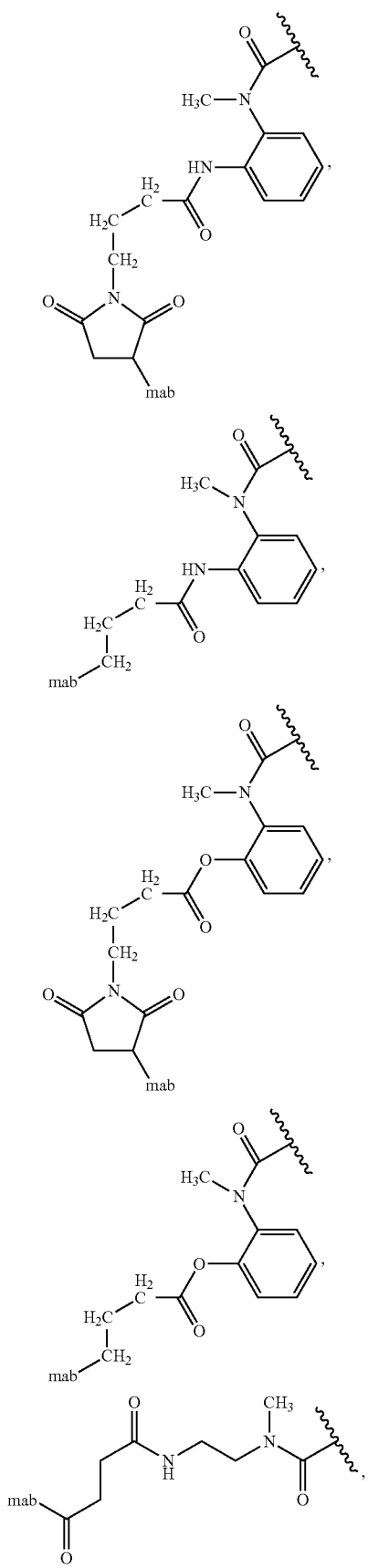
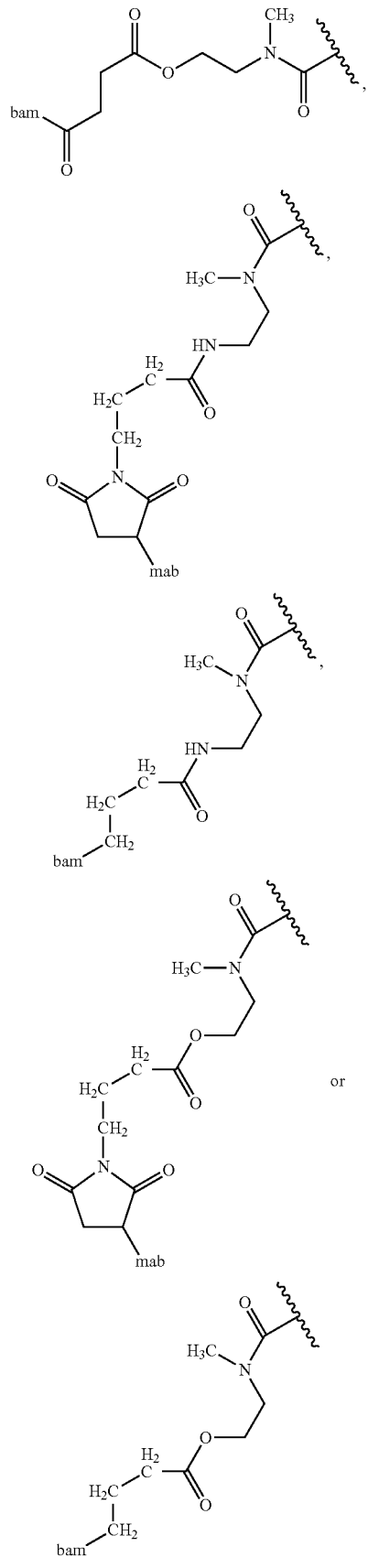

wherein mab is a monoclonal antibody; or the compound 5-(2-(dimethylamino)ethyl)-9-methoxy-2,3-methylenedioxy-6-oxo-5,6-dihydrodibenzo-[c,h][1,6]naphthyridin-8-yl ethylcarbamate or a salt thereof.

12. The compound of claim 1 wherein Z is:

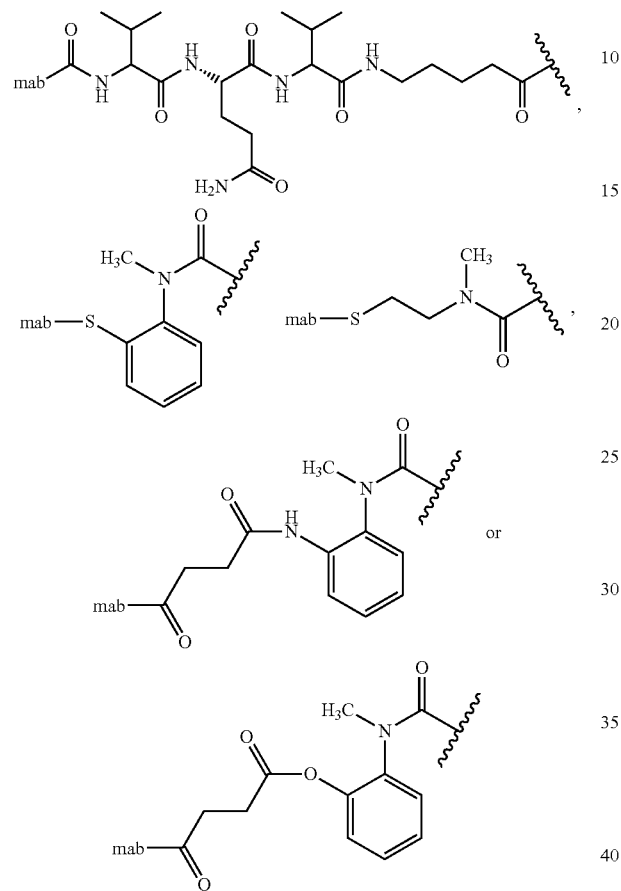

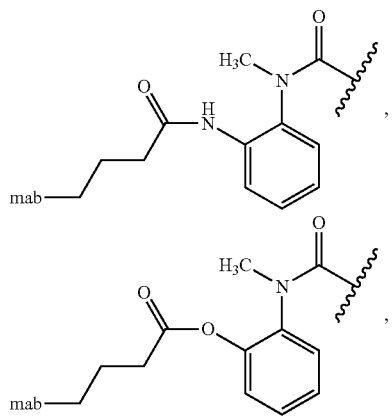

wherein mab is a monoclonal antibody; or the compound 5-(2-(dimethylamino)ethyl)-9-methoxy-2,3-methylenedioxy-6-oxo-5,6-dihydrodibenzo-[c,h][1,6]naphthyridin-8-yl ethylcarbamate or a salt thereof.

13. The compound of claim 1 wherein Z is:

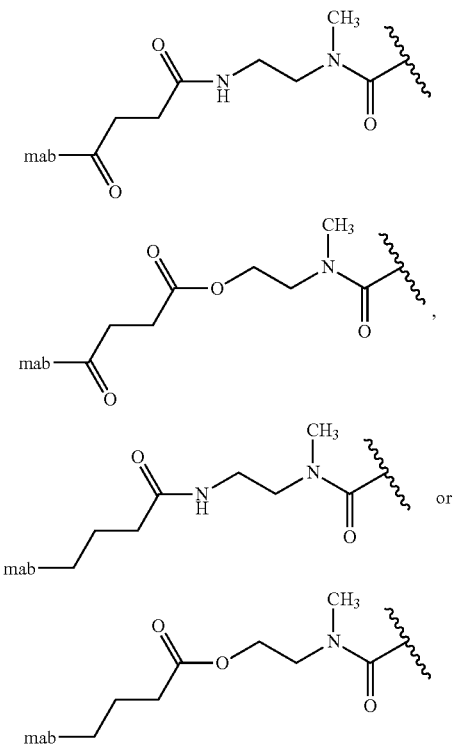

wherein mab is a monoclonal antibody; or the compound 5-(2-(dimethylamino)ethyl)-9-methoxy-2,3-methylenedioxy-6-oxo-5,6-dihydrodibenzo-[c,h][1,6]naphthyridin-8-yl ethylcarbamate or a salt thereof.

14. The compound of claim 1 wherein Z is:

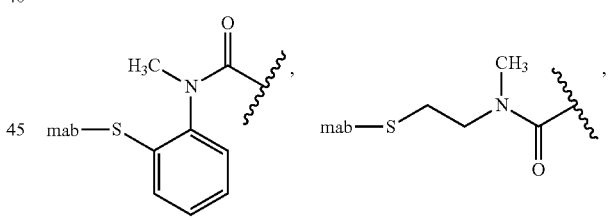

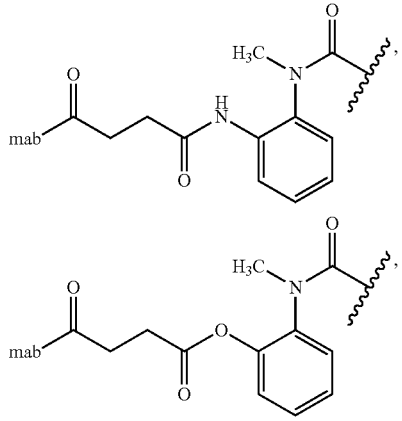

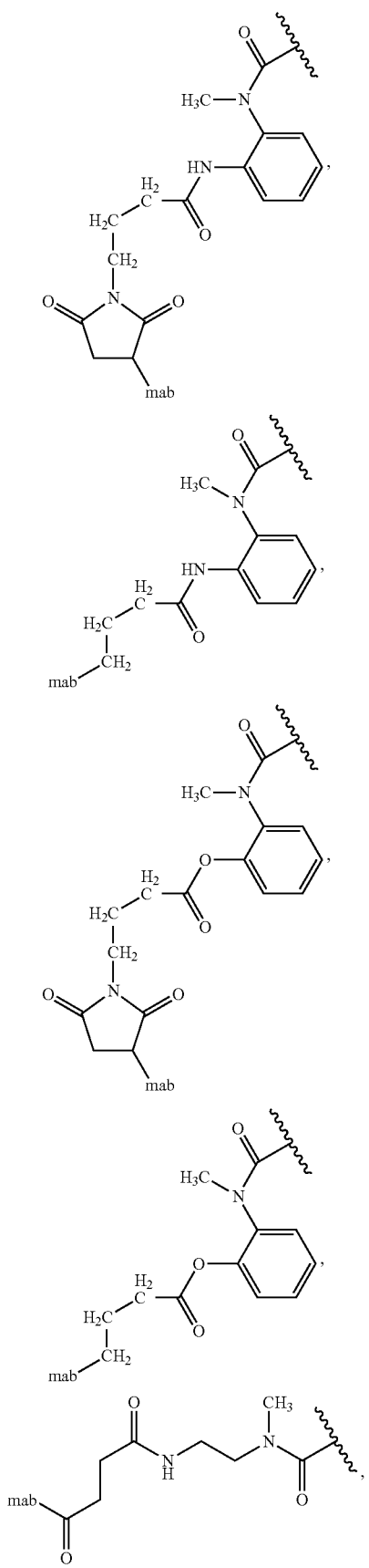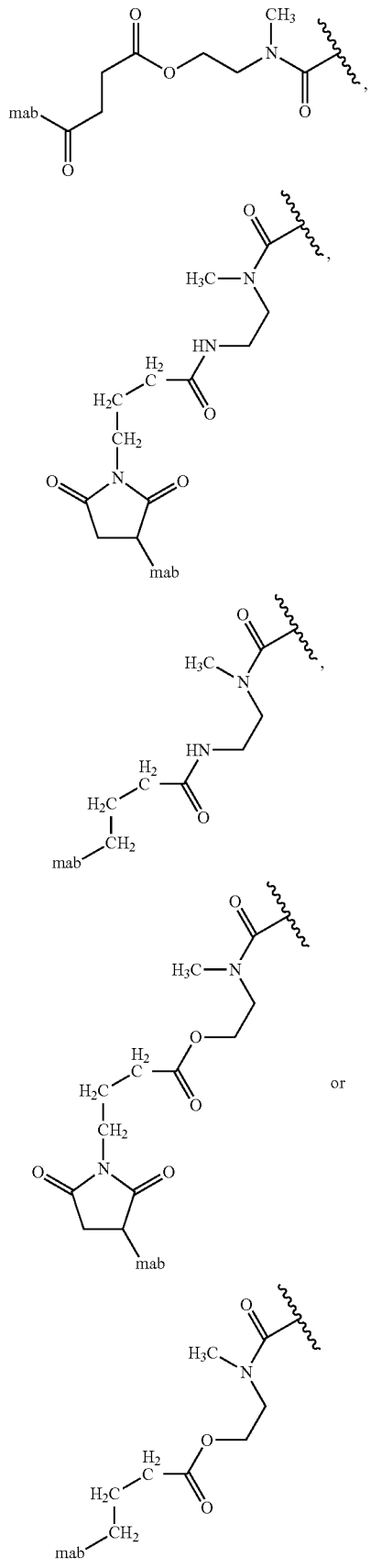

wherein mab is a monoclonal antibody; or the compound 5-(2-(dimethylamino)ethyl)-9-methoxy-2,3-methylenedioxy-6-oxo-5,6-dihydrodibenzo-[c,h][1,6]naphthyridin-8-yl ethylcarbamate or a salt thereof.

15. The compound of claim 9 wherein the mab is a monoclonal antibody to CD30, CD33, CD70, Her2 or CEA.

16. A pharmaceutical composition comprising a compound or a pharmaceutically acceptable salt thereof as described in claim 1; and a pharmaceutically acceptable diluent or carrier.

17. A method of inhibiting cancer cell growth, comprising administering to a mammal afflicted with cancer, an amount of a compound or a pharmaceutically acceptable salt thereof as described in claim 1, effective to inhibit the growth of said cancer cells.

18. A method of producing an antifungal effect in a mammal comprising administering to the mammal, an amount of a compound or a pharmaceutically acceptable salt thereof as described in claim 1, effective to provide an antifungal effect.

* * * * *